United States Patent
Fiedler et al.

(10) Patent No.: US 11,414,466 B2
(45) Date of Patent: Aug. 16, 2022

(54) FUSION PROTEINS WITH SPECIFICITY FOR ED-B AND LONG SERUM HALF-LIFE FOR DIAGNOSIS OR TREATMENT OF CANCER

(71) Applicant: Navigo Proteins GmbH, Halle/Saale (DE)

(72) Inventors: Erik Fiedler, Halle/Saale (DE); Ulrich Haupts, Halle/Saale (DE); Anja Katzschmann, Halle/Saale (DE); Eva Bosse-Doenecke, Halle/Saale (DE); Manja Gloser, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 0 days.

(21) Appl. No.: 16/761,677

(22) PCT Filed: Nov. 5, 2018

(86) PCT No.: PCT/EP2018/080174
§ 371 (c)(1),
(2) Date: May 5, 2020

(87) PCT Pub. No.: WO2019/091918
PCT Pub. Date: May 16, 2019

(65) Prior Publication Data
US 2021/0179678 A1    Jun. 17, 2021

(30) Foreign Application Priority Data
Nov. 7, 2017 (EP) ..................... 17200425

(51) Int. Cl.
*C07K 14/47* (2006.01)
(52) U.S. Cl.
CPC .......... *C07K 14/47* (2013.01); *C07K 2319/31* (2013.01)
(58) Field of Classification Search
None
See application file for complete search history.

(56) References Cited

U.S. PATENT DOCUMENTS

| | | | |
|---|---|---|---|
| 4,873,192 A | 10/1989 | Kunkel | |
| 5,789,166 A | 8/1998 | Bauer et al. | |
| 5,958,684 A | 9/1999 | Van Leeuwen et al. | |
| 6,217,863 B1 | 4/2001 | Godavarti et al. | |
| 6,569,677 B1 | 5/2003 | Legrand et al. | |
| 6,620,587 B1 | 9/2003 | Taussig et al. | |
| 6,673,901 B2 | 1/2004 | Koide | |
| 6,799,121 B2 | 9/2004 | Chu et al. | |
| 7,250,297 B1 | 7/2007 | Beste et al. | |
| 7,273,924 B1 | 9/2007 | Neri et al. | |
| 7,393,918 B2 | 7/2008 | Golemi-Kotra et al. | |
| 7,601,803 B1 | 10/2009 | Fiedler et al. | |
| 7,838,629 B2 | 11/2010 | Fiedler | |
| 7,851,599 B2 | 12/2010 | Menrad et al. | |
| 8,097,254 B2 | 1/2012 | Neri et al. | |
| 8,404,814 B2 | 3/2013 | Neri et al. | |
| 8,426,357 B2 | 4/2013 | Kraehmer et al. | |
| 8,455,625 B2 | 6/2013 | Neri et al. | |
| 8,592,144 B2 | 11/2013 | Fiedler et al. | |
| 8,592,179 B2 | 11/2013 | Schraeml et al. | |
| 8,623,373 B2 | 1/2014 | Zardi et al. | |
| 8,748,351 B2 | 6/2014 | Kunert et al. | |
| 8,790,895 B2 | 7/2014 | Fiedler et al. | |
| 8,791,238 B2 | 7/2014 | Fiedler et al. | |
| 8,921,304 B2 | 12/2014 | Steuernagel et al. | |
| 9,492,572 B2 | 11/2016 | Nerkamp et al. | |
| 9,920,098 B2 | 3/2018 | Yoshida et al. | |
| 10,858,405 B2 | 12/2020 | Bosse-Doenecke et al. | |
| 11,230,576 B2 | 1/2022 | Knick et al. | |
| 2003/0045681 A1 | 3/2003 | Neri et al. | |
| 2003/0073623 A1 | 4/2003 | Drmanac et al. | |
| 2004/0043386 A1 | 3/2004 | Pray et al. | |
| 2006/0005851 A1 | 3/2006 | Skerra et al. | |
| 2006/0099686 A1 | 5/2006 | Fiedler et al. | |
| 2007/0015248 A1 | 1/2007 | Anton et al. | |
| 2007/0111287 A1 | 5/2007 | Fiedler et al. | |
| 2007/0189963 A1 | 8/2007 | Neri et al. | |
| 2007/0248536 A1 | 10/2007 | Fiedler et al. | |

(Continued)

FOREIGN PATENT DOCUMENTS

EP    1 591 527 A1    11/2005
EP    2 532 672 A2    12/2012
(Continued)

OTHER PUBLICATIONS

Abedi et al. (1998) Green fluorescent protein as a scaffold for intracellular presentation of peptides. Nucleic Acids Research 26(2):623-630.
Advisory Action corresponding to U.S. Appl. No. 10/030,605 dated Oct. 13, 2006.
Advisory Action corresponding to U.S. Appl. No. 11/732,632 dated Jun. 30, 2010.
Advisory Action corresponding to U.S. Appl. No. 12/072,959 dated May 18, 2010.
Baker et al. (1994) Protein Expression Using Cotranslational Fusion and Cleavage of Ubiquitin. The Journal of Biological Chemistry 269(41):25381-25386.
Beal et al. (1996) Surface hydrophobic residues of multiubiquitin chains essential for proteolytic targeting. PNAS 93:861-866.

(Continued)

*Primary Examiner* — Anand U Desai
(74) *Attorney, Agent, or Firm* — Jenkins, Wilson, Taylor & Hunt, P.A.

(57) ABSTRACT

The invention relates to fusion proteins comprising at least one extradomain B of fibronectin (ED-B) specific binding domain with high stability in serum and at least one APS domain essentially consisting of or consisting of up to about 80 amino acids selected from alanine, proline, serine, and optionally aspartic acid. The fusion protein further comprises at least one coupling site consisting of at least one cysteine. The invention relates to the use of the fusion proteins or of compositions comprising the fusion proteins for medical applications, such as diagnosis or treatment of cancer or cardiovascular diseases.

10 Claims, 14 Drawing Sheets

Specification includes a Sequence Listing.

(56) References Cited

U.S. PATENT DOCUMENTS

| | | |
|---|---|---|
| 2007/0286843 A1 | 12/2007 | Plizenmaier et al. |
| 2008/0171851 A1 | 7/2008 | Fiedler et al. |
| 2010/0119446 A1 | 5/2010 | Grabulovski et al. |
| 2010/0130720 A1 | 5/2010 | Schraeml et al. |
| 2011/0162095 A1 | 6/2011 | Hill et al. |
| 2012/0244596 A1 | 9/2012 | Skerra et al. |
| 2012/0301393 A1 | 11/2012 | Steuernagel et al. |
| 2013/0011334 A1 | 1/2013 | Steuernagel et al. |
| 2013/0096276 A1 | 4/2013 | Yoshida et al. |
| 2013/0097737 A1 | 4/2013 | Kovalic et al. |
| 2013/0157878 A1 | 6/2013 | Kunert et al. |
| 2014/0135476 A1 | 5/2014 | Hall et al. |
| 2014/0219959 A1 | 8/2014 | Nerkamp et al. |
| 2015/0183846 A1 | 7/2015 | Lange et al. |
| 2018/0030098 A1 | 2/2018 | Bosse-Doenecke et al. |
| 2018/0030140 A1 | 2/2018 | Bosse-Doenecke et al. |
| 2018/0194819 A1 | 7/2018 | Fiedler et al. |
| 2018/0273636 A1 | 9/2018 | Settele et al. |
| 2018/0305463 A1 | 10/2018 | Haupts |
| 2019/0117791 A1 | 4/2019 | Haupts et al. |
| 2019/0177376 A1 | 6/2019 | Knick et al. |

FOREIGN PATENT DOCUMENTS

| | | |
|---|---|---|
| EP | 2 727 942 A1 | 5/2014 |
| EP | 2738180 | 6/2014 |
| EP | 2829552 A1 | 1/2015 |
| RU | 2134696 C1 | 8/1999 |
| WO | WO 2005/044845 A2 | 5/2005 |
| WO | WO 2007/054129 A1 | 5/2007 |
| WO | WO 2012/171541 A1 | 12/2012 |
| WO | WO 2013/186329 A1 | 12/2013 |
| WO | WO 2014/094799 | 6/2014 |
| WO | WO 2016/079033 | 5/2016 |
| WO | WO 2016/124670 A1 | 8/2016 |
| WO | WO 2016/124702 A1 | 8/2016 |
| WO | WO 2017/009421 | 1/2017 |
| WO | WO 2017/013129 | 1/2017 |
| WO | WO 2017/013136 | 1/2017 |
| WO | WO 2018/029157 A1 | 2/2018 |
| WO | WO 2019/030156 A1 | 2/2019 |
| WO | WO 2019/152318 A1 | 8/2019 |

OTHER PUBLICATIONS

Beste et al. (1999) Small antibody-like proteins with prescribed ligand specificities derived from the lipocalin fold. PNAS 96:1898-1903.
Birchler et al. (1999) Selective targeting and photocoagulation of ocular angiogenesis mediated by a phage-derived human antibody fragment. Nature Biotechnology 17:984-988.
Bird et al. (1988) Single-Chain Antigen-Binding Proteins. Science. 242:423-426.
Bofill et al. (2005) Engineering Stabilising beta-Sheet Interactions into a Conformationally Flexible Reqion of the Folding Transition State of Ubiquitin. Journal of Molecular Bioloqy 353(2):373-384.
Bolton et al. (2001) Structure and Properties of a Dimeric N-terminal Fragment of Human Ubiquitin. Journal of Molecular Biology 314(4):773-787.
Buchberger et al. (2001) The UBX Domain: A Widespread Ubiquitin-Like Module. Journal of Molecular Biology 307(1):17-24.
Burch & Haas (1994) Site-directed mutagenesis of ubiquitin. Differential roles for arginine in the interaction with ubiquitin-activating enzyme. Biochemistry 33(23):7300-7308.
Corrected Notice of Allowability corresponding to U.S. Appl. No. 11/656,646 dated Sep. 26, 2013.
Dikic et al. (2009) Ubiquitin-binding domains—from structures to functions. Nature Reviews 10:659-671.
Ecker et al. (1987) Gene Synthesis, Expression, Structures, and Functional Activities of Site-specific Mutants of Ubiquitin. The Journal of Biological Chemistry 262(29):14213-14221.

European Search Report corresponding to European Patent Application No. 06 118 519.5—2401 dated Apr. 2, 2007.
European Search Report corresponding to European Patent Application No. 09 176 574.3—2401 dated Jan. 18, 2010. (with Translation).
European Search Report corresponding to European Patent Application No. 10 181 802.9—2401 dated Feb. 10, 2011. (with Translation).
Extended European Search Report corresponding to European Patent Application No. 18213661.4—1111 dated May 31, 2019.
Hanes et al. (2000) Picomolar affinity antibodies from a fully synthetic naive library selected and evolved by ribosome display. Nature Biotechnology 18:1287-1292.
He & Taussig (1997) Antibody-ribosome-mRNA (ARM) complexes as efficient selection particles for in vitro display and evoluation of antibody combining sites. Nucleic Acids Research 25(24):5132-5134.
Hershko & Ciechanover (1998) The Ubiquitin System. Annu Rev Biochem 67:425-479.
Hey et al. (2005) Artificial, non-antibody binding proteins for pharmaceutical and industrial applications. TRENDS in Biotechnologv 23(10):514-522.
Intent to Grant corresponding to European Patent Application No. EP 10 787 815.9—1410 dated Aug. 13, 2013.
International Preliminary Report on Patentability (Chapter I of the Patent Cooperation Treaty) corresponding to International Patent Application No. PCT/EP2007/062375 dated May 19, 2009.
International Preliminary Report on Patentability (Chapter I of the Patent Cooperation Treaty) corresponding to International Patent Application No. PCT/EP2010/069665 dated Jun. 19, 2012.
International Preliminary Report on Patentability (Chapter I of the Patent Cooperation Treaty) corresponding to International Patent Application No. PCT/EP2016/052345 dated Aug. 8, 2017.
International Preliminary Report on Patentability corresponding to International Patent Application No. PCT/EP2004/005730 dated Mav 13, 2005. (with Translation).
International Preliminary Report on Patentability corresponding to International Patent Application No. PCT/EP2016/067216 dated Jan. 23, 2018.
International Search Report and Written Opinion corresponding to International Application No. PCT/EP2016/066774 dated Sep. 14, 2016.
International Search Report and Written Opinion corresponding to International Application No. PCT/EP2016/067216 dated Oct. 12, 2016.
International Search Report and Written Opinion corresponding to International Patent Application No. PCT/EP2016/052408 dated May 2, 2016.
International Search Report corresponding to International Application No. PCT/EP2016/067207 dated Sep. 29, 2016.
International Search Report corresponding to International Patent Application No. PCT/EP2000/006698 dated Feb. 2, 2001.
International Search Report corresponding to International Patent Application No. PCT/EP2004/005730 dated Oct. 5, 2004.
International Search Report corresponding to International Patent Application No. PCT/EP2005/010932 dated Apr. 11, 2006.
International Search Report corresponding to International Patent Application No. PCT/EP2007/062375 dated Apr. 25, 2008.
International Search Report corresponding to International Patent Application No. PCT/EP2010/069665 dated Apr. 13, 2011.
International Search Report corresponding to International Patent Application No. PCT/EP2010/069674 dated Jun. 17, 2011.
International Search Report corresponding to International Patent Application No. PCT/EP2011/002962 dated Mar. 19, 2012.
International Search Report corresponding to International Patent Application No. PCT/EP2012/061455 dated Oct. 25, 2012.
International Search Report corresponding to International Patent Application No. PCT/EP2012/061459 dated Sep. 24, 2012.
International Search Report corresponding to International Patent Application No. PCT/EP2013/062310 dated Aug. 2, 2013.
International Search Report corresponding to International Patent Application No. PCT/EP2019/085596 dated Feb. 6, 2020.

(56) References Cited

OTHER PUBLICATIONS

International Search Report corresponding to International Patent Application No. PCT/EP2020/052438 dated Mar. 19, 2020.
Jackson (2006) Ubiquitin: a small protein folding paradigm. Org Biomol Chem 4(10):1845-1853.
Khorasanizadeh et al. (1993) Folding and stability of a tryptophan-containing mutant of ubiquitin. Biochemistry 32(27):7054-7063.
Kiel & Serrano (2006) The Ubiquitin Domain Superfold: Structure-based Sequence Alignments and Characterization of Binding Epitopes. Journal of Molecular Biology 355(4):821-844.
Knappik et al. (2000) Fully Synthetic Human Combinatorial Antibody Libraries (HuCAL) Based on Modular Consensus Frameworks and CDRs Randomized with Trinucleotides. Journal of Molecular Biology 296:57-86.
Koide et al. (1998)The Fibronectin Type III Domain as a Scaffold for Novel Binding Proteins. Journal of Molecular Biology 284:1141-1151.
Kolchanov & Shindyalov (1988) Single amino acid substitutions producing instability of globular proteins. Calculation of their frequencies in the entire mutational spectra of the alpha- and beta-subunits of human hemoglobin. Journal of Molecular Evolution 27:154-162.
Ku & Schultz (1995) Alternate protein frameworks for molecular recognition. PNAS 92:6552-6556.
Larsen & Wang. (2002) The Ubiquitin Superfamily: Members, Features, and Phylogenies. Journal of Proteome Research 1:411-419.
Laub et al. (1995) Localized solution structure refinement of an F45W variant of ubiquitin using stochastic boundary molecular dynamics and NMR distance restraints. Protein Science 4:973-982.
Lazar et al. (1997) De novo design of the hydrophobic core of ubiquitin. Protein Science 6:1167-1178.
Lipovsek & Plückthun (2004) In-vitro protein evolution by ribosome display and mRNA display. Journal of Immunological Methods 290:51-67.
Lo et al. (2009) Structural Basis for Recognition of Diubiquitins by NEMO. Molecular Cell 33:602-615.
Loladze et al. (2005) Both helical propensity and side-chain hydrophobicity at a partially exposed site in alpha-helix contribute to the thermodynamic stability of ubiquitin. Proteins 58(1):1-6.
Lorey et al. (2014) Novel ubiquitin-derived high affinity binding proteins with tumor targeting properties. Journal of Biological Chemistry. 289(12):8493-8507.
McConnell & Hoess (1995) Tendamistat as a Scaffold for Conformationally Constrained Phage Peptide Libraries. The Journal of Molecular Biology 250:460-470.
Nord et al. (1997) Binding proteins selected from combinatorial libraries of an (-helical bacterial receptor domain. Nature Biotechnology 15:772-777.
Notice of Allowance corresponding to U.S. Appl. No. 10/030,605 dated Apr. 14, 2009.
Notice of Allowance corresponding to U.S. Appl. No. 11/283,332 dated Jun. 6, 2014.
Notice of Allowance corresponding to U.S. Appl. No. 11/656,646 dated Aug. 27, 2013.
Notice of Allowance corresponding to U.S. Appl. No. 11/732,632 dated Aug. 23, 2010.
Notice of Allowance corresponding to U.S. Appl. No. 12/072,959 dated Jun. 3, 2014.
Notice of Allowance corresponding to U.S. Appl. No. 12/514,550 dated Sep. 10, 2013.
Notice of Allowance corresponding to U.S. Appl. No. 13/142,195 dated Aug. 4, 2014.
Notice of Allowance corresponding to U.S. Appl. No. 13/144,809 dated Mar. 3, 2014.
Notice of Allowance corresponding to U.S. Appl. No. 14/126,358 dated Sep. 9, 2016.
Notice of Allowance corresponding to U.S. Appl. No. 15/548,976 dated Jul. 22, 2020.
Notice of Allowance corresponding to U.S. Appl. No. 15/744,054 dated Jan. 9, 2020.
Notice of Allowance corresponding to U.S. Appl. No. 15/744,147 dated Aug. 17, 2020.
Notice of Allowance corresponding to U.S. Appl. No. 16/324,651 dated Oct. 26, 2021.
Nygren & Uhlen (1997) Scaffolds for engineering novel binding sites in proteins. Current Opinion in Structural Biology 7:463-469.
Office Action (Restriction Requirement) corresponding to U.S. Appl. No. 16/324,651 dated Feb. 4, 2021.
Office Action corresponding to Australian Patent Application No. 2012268970 dated Aug. 27, 2015.
Office Action corresponding to Canadian Patent Application No. 2,778,871 dated Jan. 30, 2014.
Office Action corresponding to Canadian Patent Application No. 2,837,804 dated May 1, 2015.
Office Action corresponding to Chinese Patent Application No. 201080056911.6 dated Jul. 31, 2013. Translation.
Office Action corresponding to European Patent Application No. 00 944 034.8—2401 dated Oct. 7, 2004. (with Translation).
Office Action corresponding to Japanese Patent Application No. 2012-504036 dated Aug. 26, 2013.
Office Action corresponding to Japanese Patent Application No. 2012-542583 dated Apr. 22, 2014.
Office Action corresponding to Korean Patent Application No. 10-2011-7018847 dated Jan. 30, 2013. Translation.
Office Action corresponding to Russian Patent Application No. 2012114662/10(022146) dated Dec. 18, 2013.
Office Action corresponding to Russian Patent Application No. 2012114662/10(022146) dated Sep. 8, 2014. (with Translation).
Office Action corresponding to Russian Patent Application No. 2012115491 dated Dec. 24, 2013.
Office Action corresponding to U.S. Appl. No. 10/030,605 dated Apr. 12, 2006.
Office Action corresponding to U.S. Appl. No. 10/030,605 dated Aug. 10, 2005.
Office Action corresponding to U.S. Appl. No. 10/030,605 dated Feb. 15, 2005.
Office Action corresponding to U.S. Appl. No. 10/030,605 dated Feb. 28, 2007.
Office Action corresponding to U.S. Appl. No. 10/030,605 dated Jul. 1, 2008.
Office Action corresponding to U.S. Appl. No. 10/030,605 dated Nov. 16, 2007.
Office Action corresponding to U.S. Appl. No. 10/030,605 dated Sep. 21, 2004.
Office Action corresponding to U.S. Appl. No. 11/283,332 dated Jan. 9, 2008.
Office Action corresponding to U.S. Appl. No. 11/283,332 dated Mar. 3, 2010.
Office Action corresponding to U.S. Appl. No. 11/283,332 dated May 30, 2008.
Office Action corresponding to U.S. Appl. No. 11/283,332 dated Nov. 28, 2008.
Office Action corresponding to U.S. Appl. No. 11/283,332 dated Sep. 3, 2013.
Office Action corresponding to U.S. Appl. No. 11/283,332 dated Sep. 4, 2009.
Office Action corresponding to U.S. Appl. No. 11/656,646 dated May 25, 2010.
Office Action corresponding to U.S. Appl. No. 11/656,646 dated Nov. 13, 2009.
Office Action corresponding to U.S. Appl. No. 11/656,646 dated Sep. 1, 2009.
Office Action corresponding to U.S. Appl. No. 11/732,632 dated Aug. 21, 2009.
Office Action corresponding to U.S. Appl. No. 11/732,632 dated Jun. 3, 2009.
Office Action corresponding to U.S. Appl. No. 11/732,632 dated Mar. 19, 2010.
Office Action corresponding to U.S. Appl. No. 12/072,959 dated Aug. 30, 2013.

(56) References Cited

OTHER PUBLICATIONS

Office Action corresponding to U.S. Appl. No. 12/072,959 dated Jan. 27, 2009.
Office Action corresponding to U.S. Appl. No. 12/072,959 dated Jan. 5, 2010.
Office Action corresponding to U.S. Appl. No. 12/072,959 dated Jul. 24, 2008.
Office Action corresponding to U.S. Appl. No. 12/514,550 dated Aug. 3, 2011.
Office Action corresponding to U.S. Appl. No. 12/514,550 dated Mar. 12. 2012.
Office Action corresponding to U.S. Appl. No. 12/514,550 dated Sep. 15, 2011.
Office Action corresponding to U.S. Appl. No. 13/142,195 dated Feb. 11, 2013.
Office Action corresponding to U.S. Appl. No. 13/142,195 dated Feb. 4, 2014.
Office Action corresponding to U.S. Appl. No. 13/142,195 dated May 29, 2013.
Office Action corresponding to U.S. Appl. No. 13/144,809 dated Oct. 18, 2013.
Office Action corresponding to U.S. Appl. No. 13/516,002 dated Apr. 6, 2015.
Office Action corresponding to U.S. Appl. No. 13/516,002 dated Jan. 26, 2015.
Office Action corresponding to U.S. Appl. No. 14/126,341 dated May 1, 2015.
Office Action corresponding to U.S. Appl. No. 14/126,341 dated Sep. 29, 2015.
Office Action corresponding to U.S. Appl. No. 14/126,358 dated Apr. 6, 2016.
Office Action corresponding to U.S. Appl. No. 14/407,213 dated May 25, 2016.
Office Action corresponding to U.S. Appl. No. 15/549,022 dated Nov. 8, 2018.
Office Action corresponding to U.S. Appl. No. 15/744,054 dated Jul. 30, 2019.
Office Action corresponding to U.S. Appl. No. 15/744,054 dated Mar. 14, 2019.
Office Action corresponding to U.S. Appl. No. 15/744,147 dated Apr. 1, 2020.
Office Action corresponding to U.S. Appl. No. 16/324,651 dated Jun. 4, 2021.
Office Action corresponding to U.S. Appl. No. 16/376,847 dated Feb. 24, 2021.
Office Action corresponding to U.S. Appl. No. 15/548,976 dated Mar. 17, 2020.
Search Report corresponding to Chinese Patent Application No. 201080056911.6 dated Jun. 14, 2013. Translation.
Skerra (2000) Engineered protein scaffolds for molecular recognition. Journal of Molecular Recognition 13(4):167-187.
Skerra et al. (2007) Alternative non-antibody scaffolds for molecular recognition. Current Opinion in Biotechnology 18(4):295-304.
Smith et al. (1998) Small Binding Proteins Selected from a Conbinatorial Repertoire of Knottins Displayed on Phage. Journal of Molecular Biology 277(2):317-332.
Weidle et al. (2013) The Emerging Role of New Protein Scaffold-based Agents for Treament of Cancer. Caner Genomics & Proteomics 10(4):155-168.
Written Opinion corresponding to International Application No. PCT/EP2019/085596 dated Jun. 25. 2020.
Written Opinion corresponding to International Application No. PCT/EP2020/052438 dated Aug. 6, 2020.

FIG. 1. Schematic drawing of fusion proteins
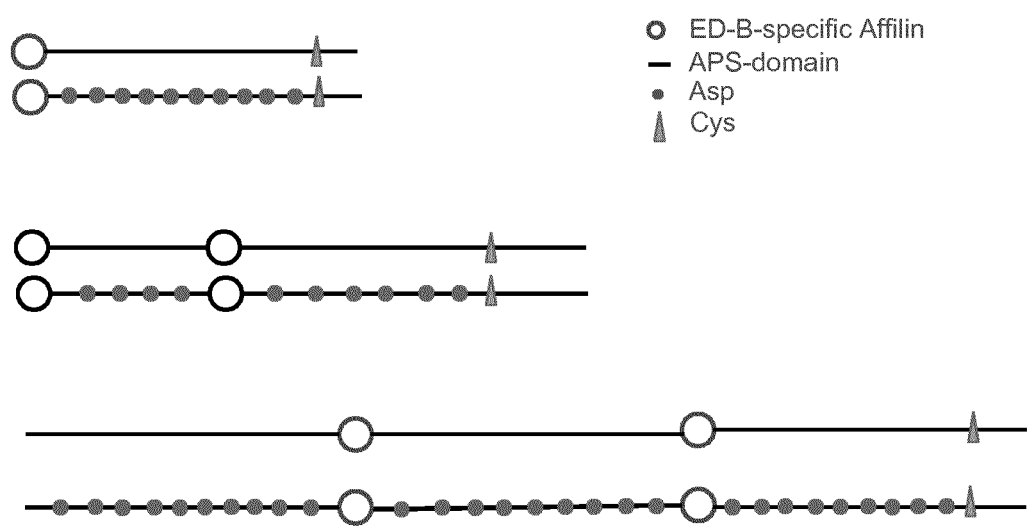

FIG. 2A. Crystal structure of an ED-B specific Affilin (SEQ ID NO: 2) in complex with ED-B fragment (surface presentation)
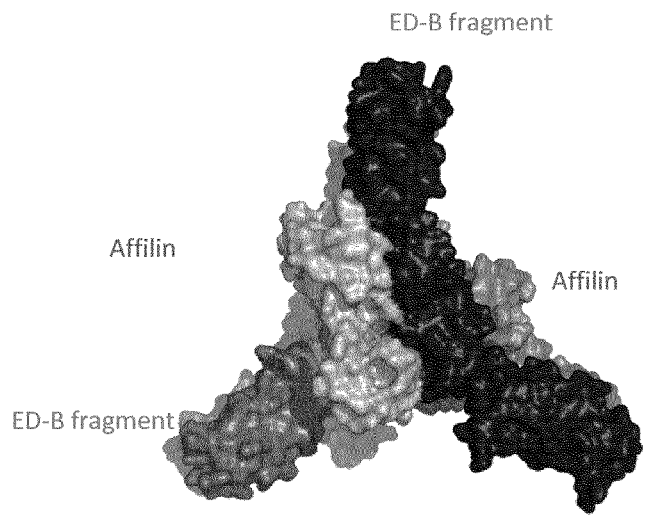
FIG. 2B. Affilin in complex with ED-B fragment
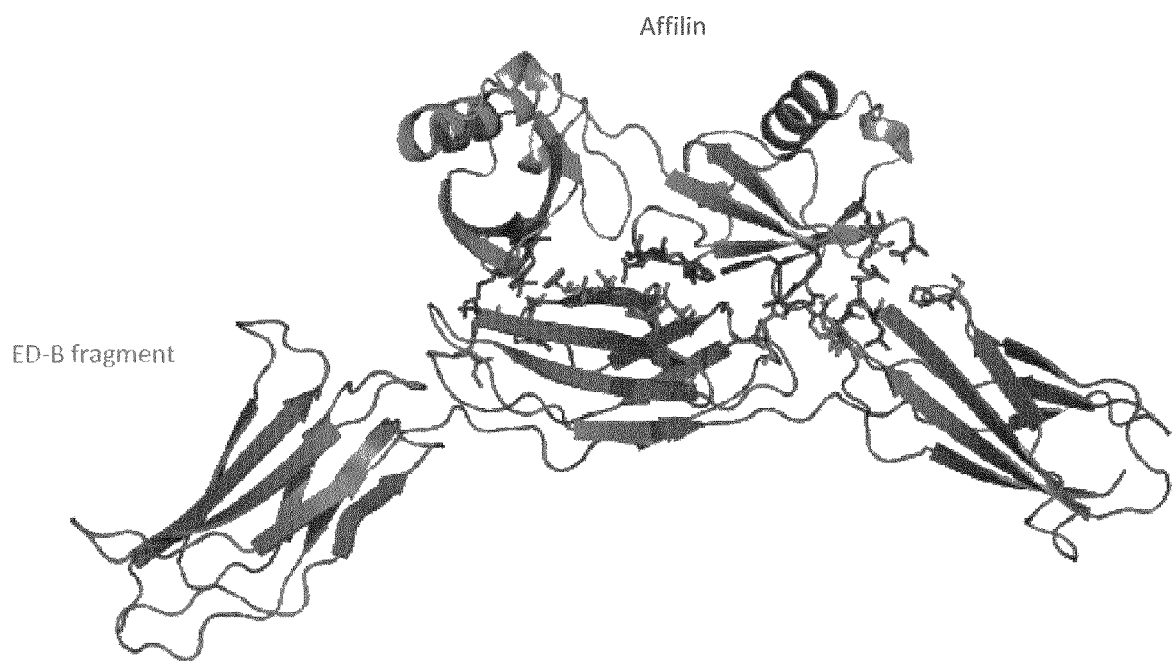

FIG. 2C. Residues involved in the interaction between SEQ ID NO: 2 with ED-B fragment

FIG. 2D. Electrostatic properties of the interface between SEQ ID NO: 2 and ED-B fragment

FIG. 3. Analysis of serum stability of ED-B binding domains via concentration dependent ELISA
FIG. 3A. Affilin-138801
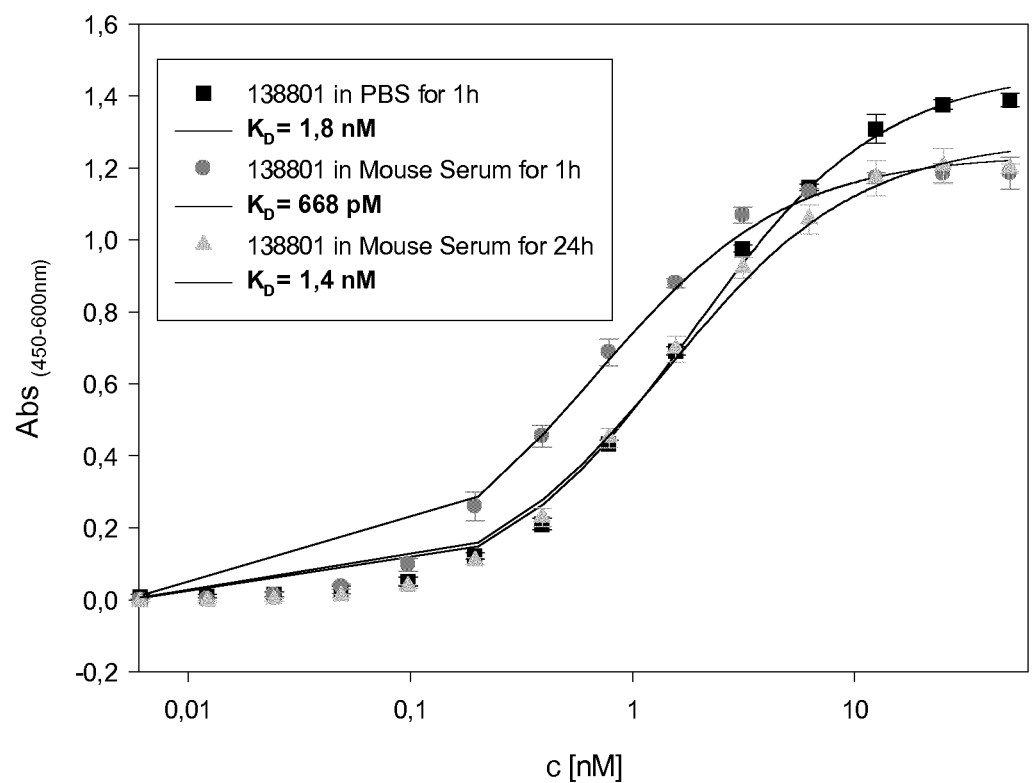

FIG. 3B. Affilin-138800
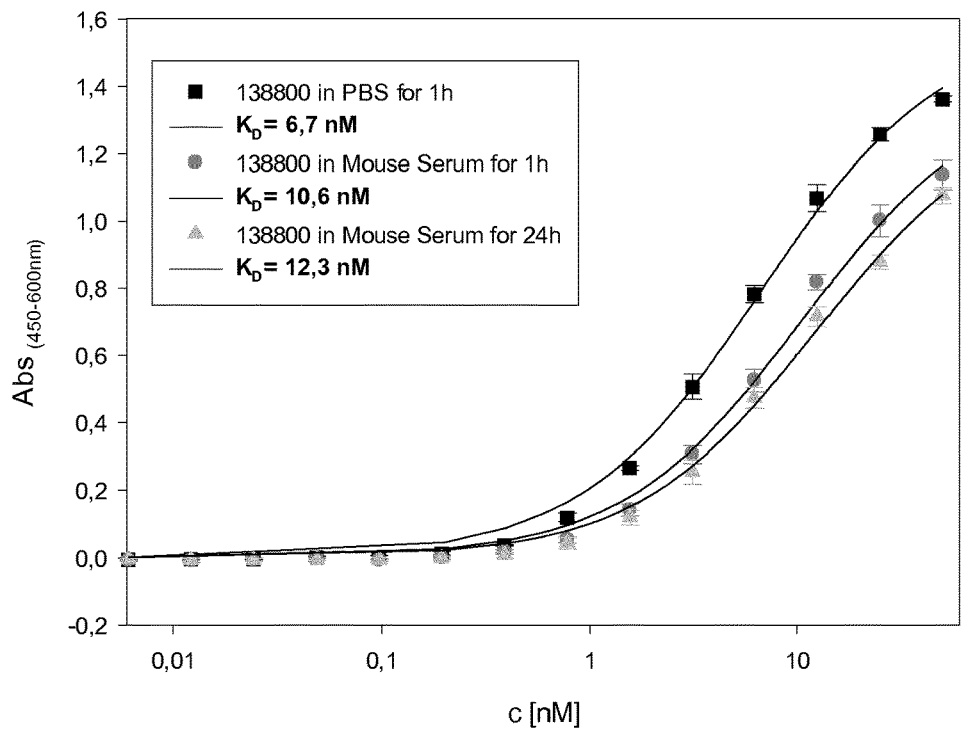
FIG. 3C. Affilin-77404
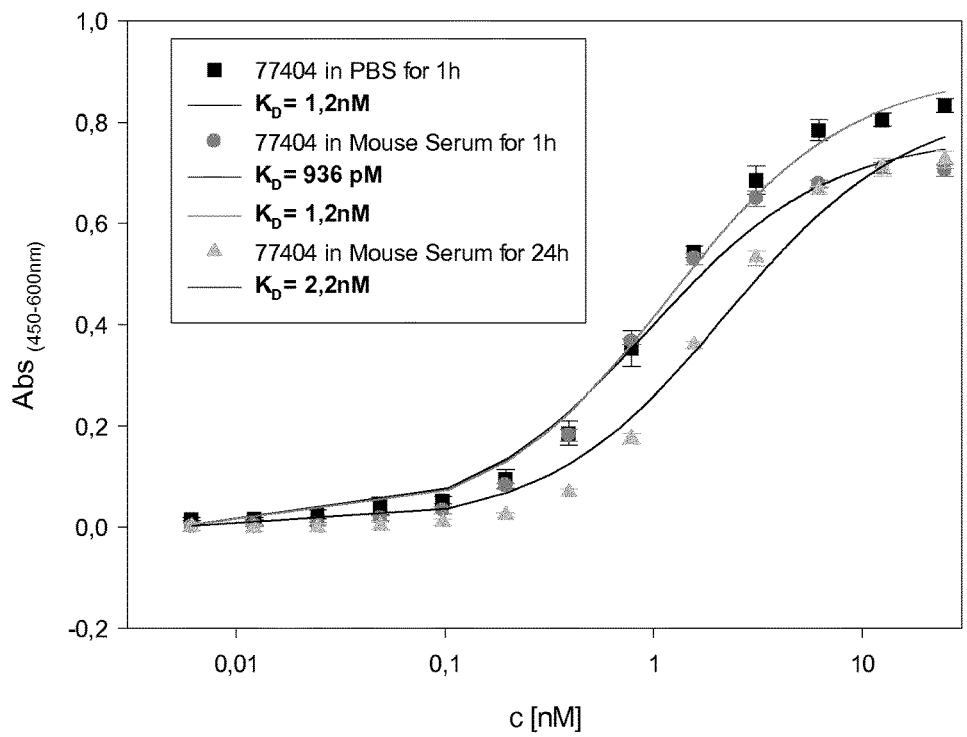

FIG. 4. Analysis of serum stability of ED-B binding domains via label-free interaction assays using SPR (Biacore)

FIG. 5. Binding of ED-B specific Affilin proteins compared to wildtype ubiquitin on Wi-38-cells FIG. 6. Binding of Afflin proteins to ED-B expressing human cells after 24 h in mouse serum or PBS

FIG. 7. Affilin-138800 shows strong binding on extracellular matrix of Wi38 cells after 24 h incubation in serum
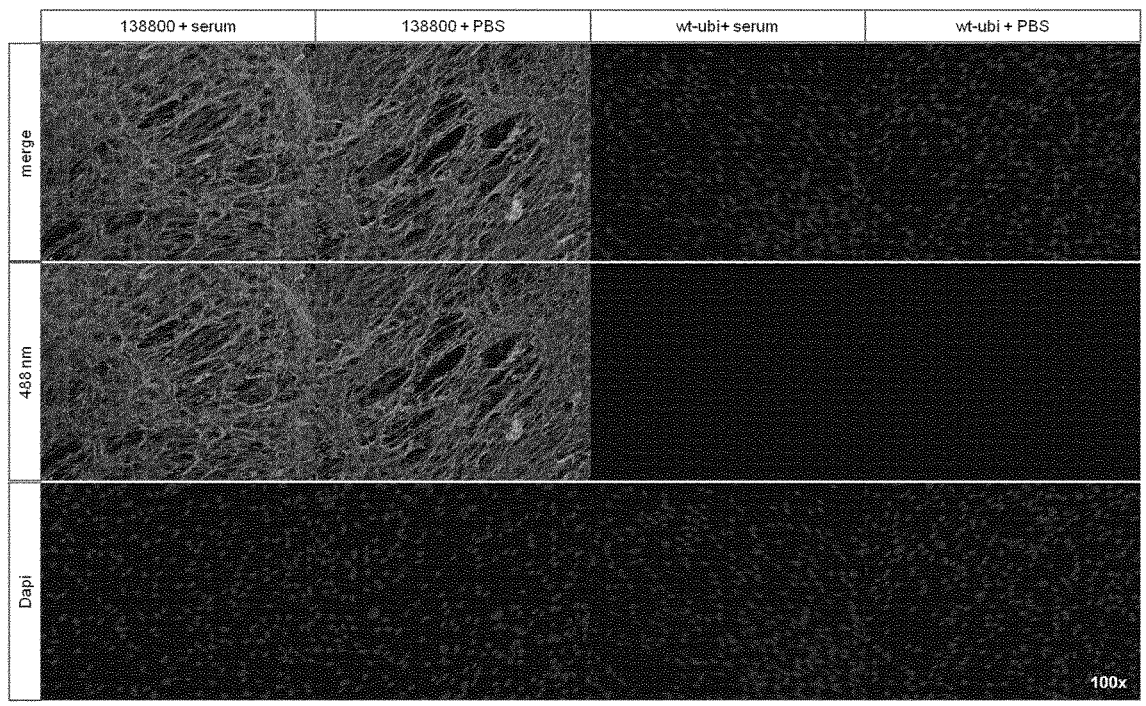

FIG. 8. DSF analysis of Affilin-181494 and Affilin-138800
FIG. 8A. Affilin-181494
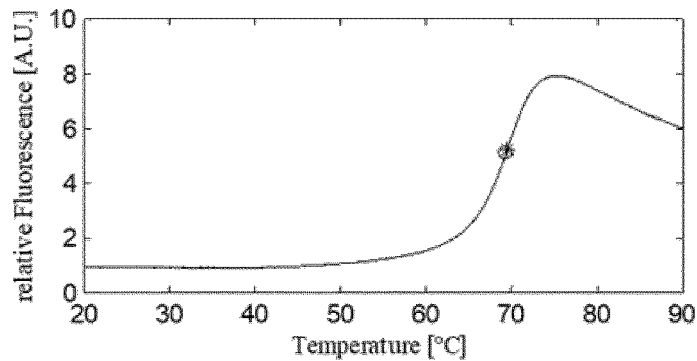
FIG. 8B. Affilin-138800
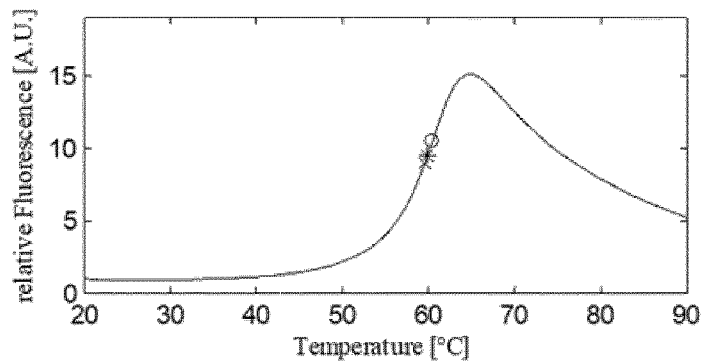
FIG. 8C. Affilin-190761
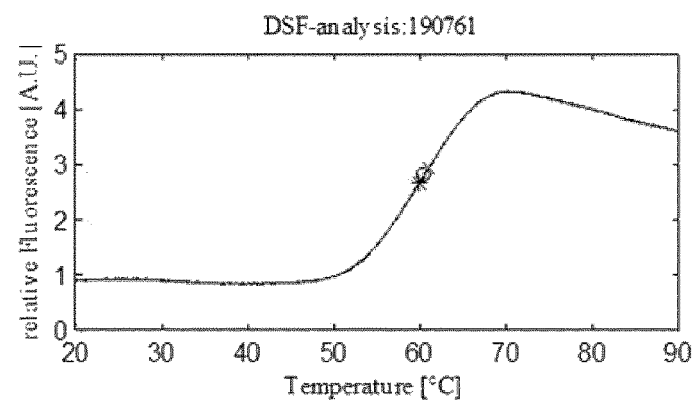

EC50 determination of 138800 on Wi38-cells

EC50 determination of 190761 on Wi38-cells

FUSION PROTEINS WITH SPECIFICITY FOR ED-B AND LONG SERUM HALF-LIFE FOR DIAGNOSIS OR TREATMENT OF CANCER

FIELD OF THE INVENTION

The invention relates to fusion proteins comprising at least one extradomain B of fibronectin (ED-B) specific binding domain with high stability in serum and at least one APS domain essentially consisting of or consisting of up to about 80 amino acids selected from alanine, proline, serine, and optionally aspartic acid. The fusion protein further comprises at least one coupling site consisting of at least one cysteine. The invention relates to the use of the fusion proteins or of compositions comprising the fusion proteins for medical applications, such as diagnosis or treatment of cancer or cardiovascular diseases.

BACKGROUND OF THE INVENTION

Extradomain B (ED-B) is one of the oncofetal fibronectin isoforms mediating cell adhesion and migration and is specifically expressed particularly in cancer, e.g. in cancer-associated processes like tumorigenesis and angiogenesis. ED-B is an important marker of angiogenesis and tumorigenesis and is considered a promising target for selective targeting of tumor vasculature and stroma. For diagnostic or therapeutic medical applications it is of advantage to attach effector molecules such as radioisotopes, chemotherapy drugs, cytotoxic agents, and cytokines to an ED-B specific binding protein. Ubiquitin muteins (also referred to as Affilin®) with specific binding activity are particularly suitable for diagnostic or therapeutic applications because ubiquitin does not influence immunological functions or hematological parameters and has no toxicological effects. Selected examples for Ubiquitin muteins with specificity and high affinity for the ED-B domain were described (EP2513138B1, EP2367843B1).

Some diagnostic or therapeutic applications require the extension of half-life of proteins to prolong their retention time in the circulation to effectively target the tumor. Standard procedures for half-life extension of biologically active proteins include the reduction of the renal clearance by exceeding the glomerular filtration threshold. In standard procedures, this is achieved by extending the molecular size to at least 60 kDa with, for example, Fc, IgG, albumin protein, or PEG.

Due to an ongoing need in diagnosis and therapy of cancer there is an ongoing requirement for novel tumor specific proteins with improved stability in serum in order to facilitate medical applications that require prolonged retention time.

The present invention provides novel fusion proteins with high affinity and specificity for the cancer target ED-B and with high serum stability due to the stable EDB-specific Affilin® domain in combination with the APS domain. The fusion proteins of the invention are particularly well-suited for medical applications that require specific targeting to ED-B and stability in serum.

The above overview does not necessarily describe all problems solved by the present invention.

SUMMARY OF THE INVENTION

A first aspect of the present invention is to provide a fusion protein with high affinity and specificity for the cancer target ED-B suitable for applications that require stability of the fusion protein in serum. This is achieved with the fusion protein comprising at least one ED-B binding domain consisting of an amino acid sequence selected from the group consisting of SEQ ID NOs: 1-13 and 53 or amino acids with at least 90% identity to SEQ ID NOs: 1-13 and 53; and at least one APS-domain essentially consisting of or consisting of 20-80 amino acid residues selected from the group of 20-60% alanine, 20-40% proline, 10-60% serine, optionally up to 10% aspartic acid, and at least one cysteine residue for the specific coupling of chemical moieties. The present invention further relates to fusion proteins wherein the ED-B binding domain has a specific binding affinity to the extracellular domain of ED-B of 10 nM or less in serum after incubation for at least 20 h. The invention is further directed to fusion proteins that comprise 1, 2, 3, or 4 identical or different EB-D binding domains and 1, 2, 3, 4, or 5 identical or different APS-domains, preferably wherein ED-B binding domains are connected via an APS-domain, preferably wherein the fusion protein comprises 2 ED-B binding domains and 2 APS-domains. The invention is related to fusion proteins wherein at least one cysteine is included in the most C-terminal APS-domain, preferably wherein the at least one cysteine is located at the C-terminus of the most C-terminal APS-domain of the fusion protein or about 20-40 amino acids from the C-terminal end of the fusion protein. In some embodiments, the invention is further related to fusion proteins wherein the order of the parts of the fusion protein from the N-terminus to the C-terminus is as follows: (i) first ED-B binding domain, first APS-domain including cysteine, or (ii) first ED-B binding domain, first APS-domain including aspartic acid and cysteine, or (iii) first ED-B binding domain, first APS-domain, second ED-B binding domain, second APS-domain including cysteine, or (iv) first ED-B binding domain, first APS-domain including aspartic acid, second ED-B binding domain, second APS-domain including aspartic acid and cysteine; or (v) first APS-domain, first ED-B binding domain, second APS-domain, second ED-B binding domain, third APS-domain including cysteine; or (vi) first APS-domain including aspartic acid, first ED-B binding domain, second APS-domain including aspartic acid, second ED-B binding domain, third APS-domain including aspartic acid and cysteine.

The present invention relates to a fusion protein wherein chemical moieties selected from the group consisting of chelators, drugs, toxins, dyes, and small molecules are coupled to the at least one cysteine, preferably wherein the chemical moiety is a chelator as complexing agent for the coupling of further substances, preferably for the coupling of radioisotopes.

The present invention relates to the use of the fusion protein in the diagnosis or treatment of cancer including but not limited to breast, ovarian, prostate, non-small cell lung, colorectal, pancreatic, skin, hepatocellular, intracraneal meningeoma, glioblastoma, or for use in the diagnosis or treatment of cardiovascular diseases including atherosclerotic plaques, myocardial infarction or inflammation preferably for use in molecular imaging.

The present invention relates to a composition comprising the fusion protein as described herein.

The present invention is directed to a method for the production of a fusion protein as described herein, comprising the steps: (a) culturing a suitable host cell under suitable conditions for the expression of the binding protein in order to obtain said fusion protein; and (b) optionally isolating said fusion protein.

This summary of the invention does not necessarily describe all features of the present invention. Other embodiments will become apparent from a review of the ensuing detailed description.

BRIEF DESCRIPTION OF THE FIGURES

FIG. 1. Schematic drawing of fusion proteins of the invention. Open circle: ED-B specific Affilin domain, black line: APS domain, closed dark grey circle: aspartic acid, grey triangle: cysteine.

FIG. 2. Interaction of Affilin-138800 with ED-B. FIG. 2A. Crystal structure of SEQ ID NO: 2 in complex with ED-B fragment 7B8. Surface presentation of the complexes in asymmetric unit cell reveal a rotated arrangement (120°) of three complexes. The three 7B8 molecules are colored in shades of dark grey and Affilin molecules in shades of light grey. FIG. 2B. Cartoon presentation of the overall view of the complex of SEQ ID NO: 2 (structure on top of the cartoon) with ED-B fragment 7B8 (structure at the lower part of the cartoon). Residues involved in interaction are shown as sticks. The interaction area was calculated 1100 Å$^2$ using the program pymol. FIG. 2C. Detailed view of SEQ ID NO: 2 with residues involved in the interaction shown as sticks. FIG. 2D. Electrostatic properties of the interface between SEQ ID NO: 2 and 7B8. The predominantly acidic cavity (A, upper molecule, medium grey) between the domains B and 7 of the ED-B fragment 7B8 is mainly covered by the mostly basic residues of SEQ ID NO: 2 (B, lower molecule, dark grey). The isoelectric point of the ED-B domain 7B8 had a calculated value of 4.1 and induced a negatively charged surface (buffer pH 6.0) whereas the interaction between Affilin and ED-B was promoted by the predominantly positively charged binding site of SEQ ID NO: 2.

FIG. 3. Analysis of serum stability of ED-B binding domains via concentration dependent ELISA in PBS (black square), 1 h in mouse serum (grey filled circle), or 24 h in mouse serum (light grey triangle). FIG. 3A. Binding of Affilin-138801 to ED-B; FIG. 3B. Binding of Affilin-138800 to ED-B; FIG. 3C. Binding of Affilin-77404 to ED-B.

FIG. 4. Analysis of serum stability of ED-B binding domains via label-free interaction assays using SPR (Biacore). The proteins were incubation for several times in mouse serum and then captured using their C-terminal STREP-tag and STREPTACTIN columns.

FIG. 6 A-D show no decrease of binding of Affilin-77404 or Affilin-138800 on cells after incubation for 24 h in mouse serum compared to incubation in PBS. FIG. 6 E-G show the stability of 181494 after incubation for 1 h in mouse serum and a slight decrease of binding after 24 h incubation in mouse serum.

FIG. 7. Analysis of binding of 100 nM Affilin-138800 (column 1 and 2) and wt-ubi (column 3 and 4) on Wi38-cells after 24 h incubation in mouse-serum (columns 1 and 3) or PBS (columns 2 and 4) with immunocytology. Affilin-138800 shows strong staining on the extracellular matrix of Wi38-cells whereas the wildtype control shows no staining.

FIG. 8. DSF Analysis of Affilin-181494 (FIG. 8A), Affilin-138800 (FIG. 8B), and Affilin-190761 (FIG. 8C)

DETAILED DESCRIPTION OF THE INVENTION

Figure 4A:
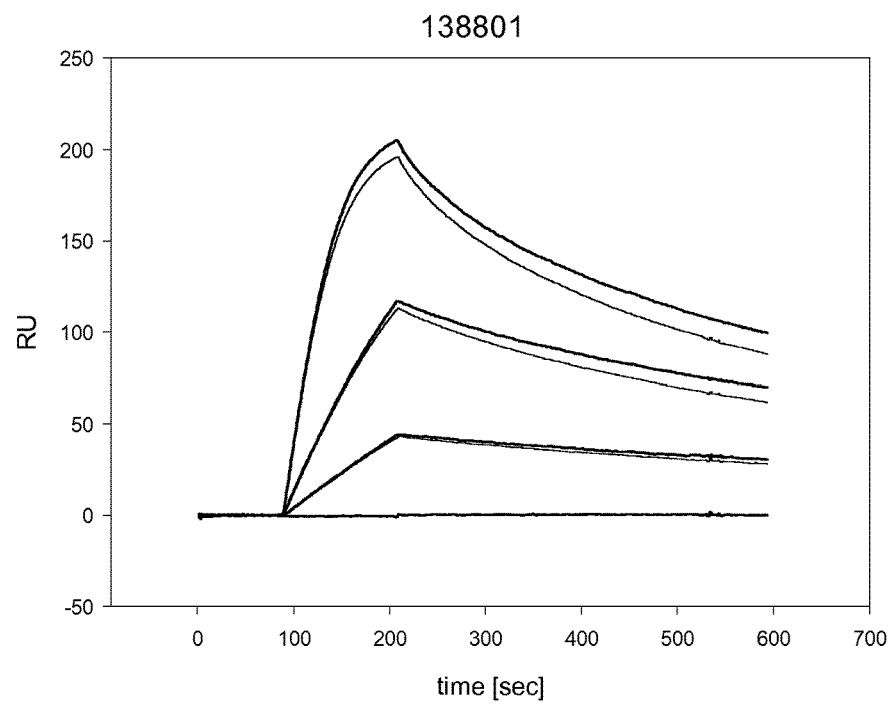
FIG. 4A. Binding kinetics of Affilin-138801 in serum or PBS.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

Definitions

The term "about", as used herein, encompasses the explicitly recited amounts as well as deviations therefrom of up to ±20%. More preferably, a deviation of up to ±15%, more preferably of up to ±10%, and most preferably up to 5% is encompassed by the term "about". The term "at least about 10, 20, 30, 40, 50, 60, 70, 80 amino acid residues" is not limited to the concise number of amino acid residues but also comprises amino acid stretches that comprise up to 20% additional or comprise up to 20% less residues. For example "about 40 amino acid residues" may also comprise 32 to 48 amino acid residues without deferring from the present invention.

The term "ED-B" refers to extra domain B of oncofetal human fibronectin. ED-B occurs in an oncofetal fibronectin isoform between the domains $Fn^{III}7$ and $Fn^{III}8$ through alternative splicing of pre-mRNA. The term "67B89" or "7B8" refers to human ED-B flanked by its neighboring N-terminal domains 6 and 7 and C-terminal domains 8 and 9 (Uniprot P02751-7 for human 7B8, Uniprot P11276 for murine 7B8). The extra-domain B is conserved to 100% in human and mouse.

The term "fusion protein" relates to a protein comprising at least a first amino acid chain joined genetically to at least a second amino acid chain. Thus, a fusion protein may comprise a multimer of proteins/peptides which are expressed as a single, linear polypeptide. It may comprise one, two, three, four, or even more proteins/peptides. For example, a fusion protein can be created through joining of two or more genes that originally coded for separate proteins/peptides. As will be explained below in greater detail, the "fusion protein" of the invention comprises at least two components, namely (i) at least one ED-B binding domain and (ii) at least one APS domain.

The term "fused" means that the components are linked by peptide bonds, either directly or via peptide linkers.

The term "domain" refers to a sub-structure which is part of a fusion protein.

The terms "ED-B binding domain" or "ED-B binding protein" refer to an amino acid sequence capable of binding to ED-B. Any such binding protein may comprise additional components such as, for example, multimerization moieties, polypeptide tags, and/or non-proteinaceous polymer molecules.

The term "Affilin" or "Affilin®" (registered trademark of Navigo Proteins GmbH, formerly SciI Proteins GmbH) as used herein refers to non-immunoglobulin derived binding proteins based on ubiquitin muteins. An Affilin is not a naturally occurring ubiquitin existing in or isolated from nature.

The terms "Affilin" as used herein refers to derivatives of bis-ubiquitin which differ from bis-ubiquitin (for example, SEQ ID NO: 31 or SEQ ID NO: 32) or from proteins with at least 95% amino acid identity to SEQ ID NOs: 31-32 by amino acid exchanges, insertions, deletions, or any combination thereof, provided that the Affilin has a specific binding affinity to ED-B. The functional property of ED-B binding is a de novo created property for the Affilin. An Affilin molecule according to this invention comprises or consists of two modified ubiquitin moieties linked together in a head-to-tail fusion. A "head-to-tail fusion" is to be understood as fusing two proteins or peptides together by connecting them in the direction (head) N-C-N-C- (tail), as described for example in EP2379581 B1 which is incorporated herein by reference. To generate a bis-ubiquitin, two ubiquitin muteins may be connected directly without any linker or with peptide linkers, for example "GG" or "GIG".

The term "APS domain" refers to a sub-structure of the fusion protein essentially consisting of or consisting of three amino acids (alanine, proline, serine), or essentially consisting of or consisting of four amino acids (alanine, proline, serine, aspartic acid), or essentially consisting of or consisting of five amino acids (alanine, proline, serine, aspartic acid, cysteine).

The term "coupling site" as employed herein means a cysteine or a cysteine rich amino acid sequence that is capable of reacting with other chemical groups to couple the fusion protein of the invention to other chemical moieties.

The term "binding" according to the invention preferably relates to a specific binding.

The term "dissociation constant" or "$K_D$" defines the specific binding affinity. As used herein, the term "$K_D$" (usually measured in "mol/L", sometimes abbreviated as "M") is intended to refer to the dissociation equilibrium constant of the particular interaction between between a binding protein (e.g., ED-B specific Affilin) and a target protein (e.g. ED-B).

As used herein, the terms "bind specifically", "specifically bind", and "specific binding" are understood to mean that the ED-B binding domain of the fusion protein of the invention has a selective binding affinity for ED-B with a dissociation constant $K_D$ of preferably 10 nM ($10^{-8}$M) or less, preferably 1 nM ($10^{-9}$M) or less, preferably 100 pM ($10^{-10}$M), or preferably 10 pM ($10^{-11}$M) or less. A high affinity corresponds to a low value of $K_D$. "Specific binding" means herein that a protein binds stronger to a target for which it is specific, compared to the binding to another molecule.

The terms "protein" and "polypeptide" refer to any chain of two or more amino acid residues linked by peptide bonds, and do not refer to a specific length of the product. Thus, "peptides", "protein", "amino acid chain," or any other term used to refer to a chain of two or more amino acid residues, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well known in the art. Thus, fusion proteins comprising two or more domains fall under the definition of the term "protein" or "polypeptides".

The term "conjugate" as used herein relates to a protein comprising or essentially consisting of at least a first protein attached chemically to other substances such as to a second protein or a non-proteinaceous moiety. The conjugation can be performed by means of organic synthesis or by use of enzymes including natural processes of enzymatic post-translational modifications. Examples for protein conjugates are glycoproteins (conjugated protein with carbohydrate component) or lipoproteins (conjugated protein with lipid component). The molecule can be attached for example at one or several sites through any form of a linker. Chemical coupling can be performed by chemistry well known to someone skilled in the art, including substitution (e.g. N-succinimidyl chemistry), addition or cycloaddition (e.g. maleimide chemistry or click chemistry) or oxidation chemistry (e.g. disulfide formation). Some examples of non-proteinaceous polymer molecules which may be chemically attached to a fusion protein of the invention are hydroxyethyl starch, polyethylene glycol, polypropylene glycol, dendritic polymers, polyoxyalkylene, chelators, drugs, toxins, small molecules, dyes, and others.

A fusion protein may further comprise one or more reactive groups or peptidic or non-peptidic components such as ligands or therapeutically or diagnostically relevant molecules such as radionuclides or toxins. It may also comprise small organic or non-amino acid based substances, e.g. a sugar, oligo- or polysaccharide, fatty acid, etc. Methods for attaching a protein of interest to such non-proteinaceous components are well known in the art, and are thus not described in further detail here.

As used herein, "substitutions" are defined as exchanges of an amino acid by another amino acid. Given the known genetic code, and recombinant and synthetic DNA techniques, the skilled scientist can readily construct DNAs encoding the amino acid variants. The term "insertions" comprises the addition of amino acid residues to the original amino acid sequence wherein the original amino acid sequence remains stable without significant structural change. The term "deletion" means that one or more amino acid residues are taken out of the original sequence and the amino acids originally N-terminal and C-terminal of the deleted amino acid are now directly connected and form a continuous amino acid sequence.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity. To determine the sequence identity, the sequence of a query protein is aligned to the sequence of a reference protein. Methods for alignment are well known in the art. For example, the SIM Local similarity program is preferably employed (Xiaoquin Huang and Webb Miller (1991), Advances in Applied Mathematics, vol. 12: 337-357), that is freely available (see also: http://www.expasy.org/tools/sim-prot.html). For multiple alignment analysis ClustalW is preferably used (Thompson et al. (1994) Nucleic Acids Res., 22(22): 4673-4680).

Each amino acid of the query sequence that differs from the reference amino acid sequence at a given position is counted as one difference. An insertion or deletion in the query sequence is also counted as one difference. For example, an insertion of a linker between two ubiquitin moieties is counted as one difference compared to the reference sequence. The sum of differences is then related to the length of the reference sequence to yield a percentage of non-identity. The quantitative percentage of identity is calculated as 100 minus the percentage of non-identity. In specific cases of determining the identity of ubiquitin muteins aligned against unmodified ubiquitin, differences in positions 45, 75 and/or 76 are not counted, in particular, because they are not relevant for the novel binding capability of the ubiquitin mutein but are only modifications relevant for certain experimental settings (F45W, G75A, G76A).

The term "drug" means any substance which can affect any physical or biochemical properties of a biological organism, including but not limited to viruses, bacteria, fungi, plants, animals, and humans. In particular, the term includes any substance intended for diagnosis, treatment, or prevention of diseases in organisms, in particular humans or animals.

Embodiments of the Invention

The present invention will now be further described in more detail. Each embodiment defined below may be combined with any other embodiment or embodiments unless clearly indicated to the contrary. In particular, any feature indicated as being preferred or advantageous may be combined with any other feature or features indicated as being preferred or advantageous.

The present invention relates to a fusion protein comprising at least ED-B-specific domain, and at least one APS domain consisting of up to about 80 amino acid residues wherein the APS domain is essentially consisting of or consisting of alanine, proline, serine, and optionally an acidic amino acid. The fusion protein also comprises a coupling site for the coupling of chemical moieties. In preferred embodiments, the coupling site is at least one Cysteine located at the C-terminus or about 20-40 amino acids from the C-terminal end of the fusion protein. The invention relates to a fusion protein comprising at least one ED-B binding domain consisting of an amino acid sequence selected from the group consisting of SEQ ID NOs: 1-13, and 53 or amino acid sequence with at least 90% identity to SEQ ID NOs: 1-13, and 53; and at least one APS-domain essentially consisting of or consisting of 20-80 amino acid residues selected from the group of 20-60% alanine, 20-40% proline, 10-60% serine, optionally up to 10% aspartic acid, and optionally at least one cysteine as coupling site. It is important that the ED-B binding domain of the fusion protein is stable in serum, i.e. that the ED-B binding domain has a specific binding affinity to the extracellular domain of ED-B of 10 nM or less in serum after incubation for at least 20 h. Fusion proteins may comprise or consist of SEQ ID NO: 21-30 or amino acid sequences with at least 80% sequence identity, at least 85% sequence identity, at least 90% sequence identity, at least 95% sequence identity, or at least 98% sequence identity to SEQ ID NO: 21-30.

Structure of the fusion protein from the N-terminus to the C-terminus. In one embodiment of the invention, the fusion protein comprises 1, 2, 3, 4 ED-B specific domains, preferably 1 or 2 ED-B specific domains. In some embodiment of the invention, the fusion protein comprises at least two identical ED-B binding domains. In other embodiments of the invention, the fusion protein comprises two different ED-B binding domains. In some embodiments, the fusion protein comprises two identical or different APS domains. In preferred embodiments of the invention, two ED-B binding domains are connected via an APS-domain.

The order of the domains of the fusion protein preferably from the N-terminus to the C-terminus is, for example, as follows (see FIG. 1): (i) first ED-B binding domain, first APS-domain including cysteine, or (ii) first ED-B binding domain, first APS-domain including aspartic acid and cysteine, or (iii) first ED-B binding domain, first APS-domain, second ED-B binding domain, second APS-domain including cysteine, or (iv) first ED-B binding domain, first APS-domain including aspartic acid, second ED-B binding domain, second APS-domain including aspartic acid and cysteine, or (v) first APS-domain, first ED-B binding domain, second APS-domain, second ED-B binding domain, third APS-domain including cysteine; or (vi) first APS-domain including aspartic acid, first ED-B binding domain, second APS-domain including aspartic acid, second ED-B binding domain, third APS-domain including aspartic acid and cysteine.

Other permutations are possible. It is preferred that the APS domain is fused to the C-terminus of an ED-B specific Affilin. It is further preferred that an APS domain consists of maximal 79 amino acids.

ED-B binding domain. The ED-B binding domain of the fusion protein consists of SEQ ID NO: 1-13 and 53 or at least 90% identical amino acid sequences or functional variants thereof. The ED-B binding domains (ED-B specific Affilin) of SEQ ID NOs: 1-13 and 53 or sequences with at least 90%, at least 95%, or at least 98% identical amino acid residues thereto have a specific binding affinity to the extracellular domain of ED-B of 10 nM or less in serum after incubation for at least 20 h, preferably at least 24 h or longer. The ED-B specific Affilin proteins of SEQ ID NO: 1-13 and 53 are particularly serum stable (see FIGS. 3-7).

Affilin-77404 (SEQ ID NO: 1) and variants with at least 90% identical amino acid residues thereto have the following amino acid motifs: 4W, 6H, 62N, 64K, 65L, 66S, preferably 2R, 2T or 2V, and 63P or 63F (Table 1). The numbering of amino acid residues in Table 1 corresponds to bis-ubiquitin (SEQ ID NO: 31). Table 1 refers only to differences in the ubiquitin moieties of the Affilin proteins, not reflecting the linker sequence.

Table 1. Affilin-77404 (SEQ ID NO: 1) and Amino Acid Sequences with at Least 90% Identity

|   | 2 | 4 | 6 | 62 | 63 | 64 | 65 | 66 | 85 | 87 | 141 | 142 | 143 | 144 | 145 | further subst. | identity |
|---|---|---|---|----|----|----|----|----|----|----|-----|-----|-----|-----|-----|----------------|----------|
| wt | Q | F | K | Q | K | E | S | T | K | L | Q | K | E | S | T | | |
| 77404 | R | W | H | N | P | K | L | S | H | Q | G | W | Q | A | P | | 100.00% |
| 77404-1 | R | W | H | N | F | K | L | S | H | Q | G | W | Q | A | P | | 99.90% |
| 77404-2 | V | W | H | N | F | K | L | S | H | Q | G | W | Q | A | P | | 98.68% |
| 77404-3 | T | W | H | N | F | K | L | S | H | Q | G | W | Q | A | P | | 98.68% |
| 77404-4 | T | W | H | N | F | K | L | S | R | H | G | W | Q | [S] | P | | 96.70% |
| 77404-5 | T | W | H | N | F | K | L | S | L | D | G | W | Q | [S] | P | | 96.70% |
| 77404-6 | T | W | H | N | F | K | L | S | L | T | G | W | Q | [S] | P | | 96.70% |
| 77404-7 | T | W | H | N | F | K | L | S | D | S | G | W | Q | A | P | | 96.70% |
| 77404-8 | T | W | H | N | F | K | L | S | H | E | G | W | Q | V | P | E95G | 96.05% |
| 77404-9 | T | W | H | N | F | K | L | S | T | Q | G | W | Q | [S] | P | | 96.05% |
| 77404-10 | T | W | H | N | F | K | L | S | D | V | G | W | N | A | P | I44S | 94.73% |
| 77404-11 | T | W | H | N | P | K | L | S | D | P | D | R | L | P | V | K33R, G132E | 94.07% |
| 77404-12 | T | W | H | N | F | K | L | S | D | P | G | R | L | P | K | E113K | 94.07% |
| 77404-13 | T | W | H | N | F | K | L | S | D | P | W | H | H | D | F | | 94.07% |
| 77404-14 | T | W | H | N | P | K | L | S | H | T | W | H | H | D | M | G77R | 94.07% |
| 77404-15 | T | W | H | N | F | K | L | S | D | D | A | T | L | P | N | | 94.07% |
| 77404-16 | T | W | H | N | F | K | L | S | Y | P | W | T | R | D | W | | 94.07% |
| 77404-17 | T | W | H | N | F | K | L | S | Y | Y | W | S | G | E | F | | 94.07% |
| 77404-18 | T | W | H | N | F | K | L | S | H | Q | G | W | Q | A | P | | 94.07% |
| 77404-19 | T | W | H | N | F | K | L | S | S | A | H | H | L | P | [T] | | 94.07% |
| 77404-20 | T | W | H | N | F | K | L | S | S | F | H | Y | L | P | K | | 94.07% |
| 77404-21 | T | W | H | N | F | K | L | S | S | F | H | Y | L | P | K | L8W | 93.40% |
| 77404-22 | T | W | H | N | F | K | L | S | S | Y | W | P | G | D | M | E130A | 93.40% |

Affilin-138800 (SEQ ID NO: 2) and variants with at least 90% identical amino acids thereto have the following consensus amino acid motifs: 6H, 142D, 143Y or 143W or 143A, 144R, 145F or 145W or 145Y (Table 2). The numbering corresponds to bis-ubiquitin (SEQ ID NO: 31). The bis-ubiquitin of SEQ ID NO: 31 has a linker of GIG; some of the Affilin-proteins, for example, 138800, 181494, 181493, 181492, 181491 have "GG" as linker between the two ubiquitin mutein domains whereas Affilin-138801 and 102472 have "GIG" as linking sequence between the two ubiquitin mutein domains. Affilin-190761 has no linker between the two ubiquitin mutein domains. Table 2 refers only to differences in the ubiquitin moieties of the Affilin proteins, not reflecting the linker sequence.

Table 2. Affilin-138800 (SEQ ID NO: 2) and Amino Acid Sequences with at Least 90% Identity

| SEQ 31/32 | | 6 | 8 | 38 | 62 | 63 | 64 | 65 | 66 | 85 | 87 | 141 | 142 | 143 | 144 | 145 | additional substitutions | identity |
|---|---|---|---|----|----|----|----|----|----|----|----|-----|-----|-----|-----|-----|--------------------------|----------|
| | wildtyp | K | L | P | Q | K | E | S | T | K | L | Q | K | E | S | T | | |
| SEQ 2 | 138800 | H | D | Q | D | P | Q | L | K | T | Q | — | D | Y | R | F | | 100% |
| SEQ 5 | 181491 | H | D | Q | D | P | Q | L | K | T | Q | — | D | A | R | F | | 99.34% |
| SEQ 3 | 138801 | H | D | [P] | D | P | Q | L | K | T | Q | — | D | Y | R | Y | | 98.68% |
| SEQ 4 | 102472 | H | D | [P] | D | P | Q | L | K | T | Q | — | D | Y | R | Y | | 98.68% |
| SEQ 6 | 181492 | H | D | Q | D | P | Q | L | K | T | Q | — | D | Y | R | F | R153G, A154L | 98.68% |
| SEQ 7 | 181493 | H | D | Q | D | P | Q | L | K | T | Q | — | D | Y | R | F | R153A, A154L | 98.68% |
| | 138800-1 | H | D | [P] | D | P | Q | L | K | T | Q | — | D | Y | R | F | del A154, del A155 | 98.03% |
| SEQ 13 | 181494 | H | D | Q | — | — | Q | K | K | T | Q | — | D | Y | R | F | del Q62, del K63, L67S | 96.05% |
| | 13880-2 | H | D | [P] | D | P | Q | L | K | T | Q | — | D | Y | R | Y | D21N, M80I, K90E, E113V | 96.05% |
| | 138810 | H | D | [P] | D | P | Q | L | K | T | Q | — | D | Y | R | Y | D21N, M80I, I82T, K90E, E113V | 95.39% |
| | 138802 | H | D | [P] | D | P | Q | L | K | T | Q | — | D | Y | R | Y | E24K, P37L, I78N, M80I, I82T, T93M | 95.39% |
| SEQ 53 | 190761 | H | D | [P] | A | H | Q | P | Q | Q | M | — | D | Y | R | Y | | 94.07% |
| SEQ 12 | 138800-3 | H | R | [P] | A | H | Q | P | Q | Q | M | — | D | Y | R | Y | | 94.07% |
| | 138808 | H | D | [P] | D | P | K | L | K | T | Q | — | D | Y | R | Y | E16K, V17A, P37L, M80I, I82T, E113V | 94.07% |

| SEQ 31/32 | wildtyp | 6 K | 8 L | 38 P | 62 Q | 63 K | 64 E | 65 S | 66 T | 85 K | 87 L | 141 Q | 142 K | 143 E | 144 S | 145 T | additional substitutions | identity |
|---|---|---|---|---|---|---|---|---|---|---|---|---|---|---|---|---|---|---|
| SEQ 13 | 138800-4 | H | D | [P] | [Q] | [K] | K | [S] | H | T | Q | — | D | Y | R | F | H68V, V70R, del L73, del R74 | 94.07% |
| SEQ 11 | 138800-5 | H | T | [P] | [Q] | G | V | R | M | M | R | — | D | Y | R | W | | 93.40% |
| SEQ 8 | 138800-6 | H | W | [P] | N | W | V | R | Q | L | W | — | D | W | R | W | | 93.40% |
| | 138800-7 | H | T | [P] | T | L | T | P | [T] | L | [L] | — | D | W | R | W | | 93.40% |
| SEQ 9 | 138800-8 | H | W | [P] | N | W | V | R | Q | L | W | — | D | W | R | W | G77I | 92.76% |
| SEQ 10 | 138800-9 | H | W | [P] | N | W | V | R | Q | L | W | — | D | W | R | W | L94G | 92.76% |
| | 138800-10 | H | D | [P] | H | N | W | R | N | I | I | — | D | W | R | W | K29E, E130K | 92.76% |
| | 138800-11 | H | H | [P] | N | R | D | K | R | N | N | — | D | W | R | W | K90E, Q128R | 92.10% |
| | consensus | H | | | | | | | | | | — | D | Y/W/A | R | F/W/Y | | |

In some embodiments, the ED-B binding protein comprises at least one ubiquitin mutein with deletions in position Q62 and K63 in SEQ ID NO: 37 (or SEQ ID NO: 38) and substitutions at least selected from the group consisting of K6H, L8D, E64Q, S65K, T66K, and L67S in SEQ ID NO: 37 (or SEQ ID NO: 38). In further embodiments, the ED-B binding protein comprises a ubiquitin mutein that has at least one additional substitution, preferably P38Q. In some embodiments, the ED-B binding protein comprises of at least one additional ubiquitin mutein with a deletion in position Q62 and substitutions at least selected from the group consisting K6T, L8Q, K63D, E64Y or E64W or E64F or E64A, S65R, and T66F or T66Y or T66W. In preferred embodiments, two ubiquitin muteins are linked together in a head-to-tail arrangement, either directly or by a linker, preferably a peptide linker, for example, selected from GG or GIG. In preferred embodiment, the ED-B binding protein comprises of two ubiquitin muteins wherein modifications of ubiquitin (SEQ ID NO: 37 or SEQ ID NO: 38) comprise in the first ubiquitin mutein deletions in position Q62 and K63 and substitutions at least selected from the group consisting of K6H, L8D, E64Q, S65K or S65P, T66K or T66Q, and L67S, and in the second ubiquitin mutein a deletion in position Q62 and substitutions at least selected from the group consisting K6T or K6Q, L8Q or L8M, K63D, E64Y or E64W or E64F or E64A, S65R, and T66F or T66Y or T66W. In the second ubiquitin mutein domain of the ED-B binding protein, the motif 63D, 64Y, 65R, 66Y is preferred. Some embodiments relate to ED-B binding protein of SEQ ID NO: 13 or of amino acid sequences with at least 90%, at least 94%, at least 95%, at least 96%, at least 97%, at least 98% or at least 99% amino acid identity to SEQ ID NO: 13, provided that said proteins have deletions in positions Q62 and K63 in the first ubiquitin mutein. Some embodiments relate to ED-B binding protein of SEQ ID NO: 13 (Affilin-181494) that has a high specific binding affinity to ED-B of $10^{-9}$ M or less, as determined by Biacore, and a midpoint of thermal transition of about 69° C., as measured via differential scanning fluorimetry (DSF) (see Table 5).

Far-UV circular dichroism (CD) measurements were performed to analyze the secondary structure of Affilin-138800 (SEQ ID NO: 2, as tag free protein) in comparison to wildtype bis-ubiquitin. Structural comparison of SEQ ID NO: 2 and wild-type bis-ubiquitin showed that the typical ubiquitin fold is not altered. SEQ ID NO: 2 shows a typical ubiquitin fold structure, thus the scaffold tolerates the amino acid exchanges without significant structural perturbations.

Further, the crystal structure of SEQ ID NO: 2 in complex with an ED-B containing fibronectin fragment 7B8 was solved to 2.3 Å resolution and revealed a binding to sheet C', loops CC' and EF of ED-B and loops FG and BC from domain 8 on 7B8. Each complex consists of one Affilin (SEQ ID NO: 2) and one ED-B containing fibronectin fragment 7B8. The largest structural difference occurs in the N-terminal domain of the ED-B containing fibronectin fragment. All domains involved in binding interaction of each complex showed only slightly different orientation. The binding site covered mainly the extra domain B and the "hinge" region between the extra domain B and the C-terminal domain 8 of the fibronectin (FIG. 2). Additional intermolecular contacts (400-550 Å$^2$) between the adjacent complex molecules in the asymmetric unit may result from packing interactions in the crystal environment.

In an embodiment, a fusion protein of the invention comprises one or two ED-B binding domains.

In some embodiments, the fusion protein is a multimer of ED-B binding domains, preferably of two identical ED-B binding domains connected via an APS domain. In other embodiments, two different ED-B binding domains are connected via an APS domain. The different ED-B binding domains may have specificity for the same epitope or for different epitopes.

APS domain. In an embodiment of the invention, the fusion protein of the invention comprises an APS domain covalently connecting two ED-B-specific Affilins. In such embodiment, the fusion protein comprises an APS-domain of 10 to 80 amino acid residues between two ED-B-specific Affilin moieties and a second APS-domain at the C-terminal end.

The present invention further relates to a fusion protein wherein an APS domain consists of 20-60% alanine, 20-40% proline, and 10-60% serine residues. Thus, the APS domain is hydrophilic and without secondary or tertiary structure. The advantage of having an APS domain of the invention is that the functional and structural characteristics of the ED-B binding domain are maintained and that the APS domain increases the hydrodynamic radius and solubility of the fusion protein.

Defined length of a APS domain of up to 80 amino acids. The length of the APS domain varies between at least 10 and up to a maximum of 80 amino acids. More preferably, the APS domain has a length between 20 and 80 amino acids. In one embodiment of the invention the APS domain consists of 40 amino acids. In one embodiment of the invention the APS domain consists of 60 amino acids. In one embodiment of the invention the APS domain consists of 79 amino acids. In one embodiment of the invention the first APS domain of the fusion protein consists of 40 amino acids, and the second APS domain of the fusion protein consists of 60 amino acids.

Amino acid composition of APS domain. An APS domain essentially consists of amino acids selected from the group of Ala, Pro, or Ser. It is preferred that the APS domain consist of about 30% to about 60% alanine, about 20% to about 45% proline, and about 10% to about 60% serine, preferably about 40% to about 60% alanine, about 20% to about 40% proline, and about 10% to about 30% serine. In some embodiments of the invention, the APS domain consists of 40-50% alanine, 25-35% proline, 20-30% serine, and optionally about 10% acidic amino acid, i.e. aspartic acid or glutamic acid. Acidic residues decrease the overall isoelectric point of the molecule which in turn is known to decrease renal clearance of the protein. Therefore, the advantage of an APS domain comprising acidic residues is an increased in-vivo half-life. In some embodiments, alanine, proline, serine, and optionally aspartic acid are distributed throughout the amino acid sequence so that not more than a maximum of 2, 3, 4 identical amino acid residues are adjacent, preferably a maximum of 3 amino acids. It is preferred that a maximum of 3 alanine residues are adjacent. It is further preferred that alanine is distributed every 1-4 amino acids with a maximum of 3 residues adjacent, that proline is distributed every 1-7 amino acids with a maximum of 2 residues adjacent, that serine is distributed every 1-8 amino acids with a maximum of 1 residues adjacent. In domains with aspartic acid, the aspartic acid residues are regularly distributed, preferably every 4-5 amino acids. In the most C-terminal domain, it is preferred that the aspartic acid residues are located N-terminal of the cysteine residue.

Coupling sites. In an embodiment of the invention, the coupling site (cysteine) is directly located at the C-terminus of the most C-terminal APS-domain. In other embodiments of the invention, the coupling site (i.e., cysteine) is not directly located at the C-terminus of the compound but is embedded in the most C-terminal APS-domain. It is preferred that the most terminal cysteine residue (Cys) is located at least about 5, at least about 10 amino acids, at least about 20 amino acids, at least about 30 amino acids, at least about 40 amino acids from the most C-terminal amino acid. In an embodiment of the invention, a coupling site is Cys or CysXaaCys or CysXaaXaaCys or CysXaaXaaXaaCys, wherein Xaa is preferably selected from the group consisting of alanine, proline, serine. In preferred embodiments, the fusion protein of the invention contains 1 or 2 cysteine residues for conjugating chemical moieties, for example for radioimaging purposes. An additional coupling site can be introduced in the Affilin sequence, for example, at position S57C (SEQ ID NOs: 34-36).

Suitable APS domains are, for example, selected from the group consisting of (SEQ ID NO: 14)
SAPAASPSPAAPAPSPASPAPASPASAPSAPASAPAAASA;

(SEQ ID NO: 15)
SAPAASPSAAAPAPSPASPAPASPASAPSAPASAPPAASCSAPAASPSP
AAPAPSPASPA;

(SEQ ID NO: 16)
SAPAASPDPAAPAPSDASPAPASDASAPSAPDSAPAAASA;

(SEQ ID NO: 17)
SAPAADPSAAADAPSPADPAPASDASAPSDPASADPAASCSAPAASPSP
AAPAPSPASPA;

(SEQ ID NO: 18)
SAPAASPSPAAPAPSPASPAPASPASAPSAPASAPAAASASAPAASPSP
AAPAPSPASPAPASPASAPSAPASAPAASA;

(SEQ ID NO: 19)
SAPAASPSAAAPAPSPASPAPASPASAPSAPASAPPAASPSAPAASPSP
AAPAPSPASCAAASPSAPAASPSPAAPAPS;
and (SEQ ID NO: 20)
SAPAASPSAAAPAPSPASPAPASPASAPSAPASAPPAASPSAPAASPSP
AAPAPSPASPAAASPSAPAASPSPAAPAPS, or from amino acid sequences with at least 85% identity, at least 90% identity, at least 95% identity, or at least 98% identity thereto. In some embodiments, the amino acid sequences of the APS domain of the fusion protein of the invention essentially consist or consist of SEQ ID NOs: 14-20 or amino acid sequences with at least 80% identity, at least 85% identity, at least 90% identity, at least 95% identity, or at least 98% identity thereto.

TABLE 3

Amino acid composition of APS domains of the invention

|  | Ala | Pro | Ser | Asp | Cys |
|---|---|---|---|---|---|
| SEQ ID NO: 14 |  |  |  |  |  |
| Number of amino acids in APS | 18 | 12 | 10 | 0 | 0 |
| APS domain consists of | 0.45 | 0.3 | 0.25 | 0 | 0 |
| Distribution in domain, every ( ) aa | 1 to 4 | 1 to 3 | 1 to 6 | 0 | 0 |
| Adjacent identical amino acid(s) | 1 to 3 | 1 | 1 | 0 | 0 |
| SEQ ID NO: 15 |  |  |  |  |  |
| Number of amino acids in APS | 25 | 19 | 15 | 0 | 1 |
| APS domain consists of | 0.4167 | 0.3167 | 0.25 | 0 | 0.0166 |
| Distribution in domain, every ( ) aa | 1 to 4 | 1 to 6 | 1 to 6 | 0 | 20 from C- |
| Adjacent identical amino acid(s) | 1 to 3 | 1 to 2 | 1 | 0 | 1 |
| SEQ ID NO: 16 |  |  |  |  |  |
| Number of amino acids in APS | 17 | 10 | 9 | 4 | 0 |
| APS domain consists of | 0.425 | 0.25 | 0.225 | 0.1 | 0 |
| Distribution in domain, every ( ) aa | 1 to 4 | 1 to 6 | 1 to 8 | 7 | 0 |
| Adjacent identical amino acid(s) | 1 to 3 | 1 | 1 | 1 | 0 |
| SEQ ID NO: 17 |  |  |  |  |  |
| Number of amino acids in APS | 24 | 16 | 13 | 6 | 1 |
| APS domain consists of | 0.4 | 0.2667 | 0.2167 | 0.1 | 0.0166 |
| Distribution in domain, every ( ) aa | 1 to 4 | 1 to 6 | 1 to 7 | 4 to 5* | 20 from C-term |
| Adjacent identical amino acid(s) | 1 to 3 | 1 | 1 | 1 | 1 |

TABLE 3-continued

Amino acid composition of APS domains of the invention

|  | Ala | Pro | Ser | Asp | Cys |
|---|---|---|---|---|---|
| SEQ ID NO: 18 | | | | | |
| Number of amino acids in APS | 35 | 24 | 20 | 0 | 0 |
| APS domain consists of | 0.443 | 0.304 | 0.253 | 0 | 0 |
| Distribution in domain, every ( ) aa | 1 to 4 | 1 to 7 | 1 to 6 | 0 | 0 |
| Adjacent identical amino acid(s) | 1 to 3 | 1 | 1 | 0 | 0 |
| SEQ ID NO: 19 | | | | | |
| Number of amino acids in APS | 33 | 25 | 20 | 0 | 1 |
| APS domain consists of | 0.4177 | 0.3165 | 0.2532 | 0 | 0.0126 |
| Distribution in domain, every ( ) aa | 1 to 4 | 1 to 6 | 1 to 6 | 0 | 20 from C-term |
| Adjacent identical amino acid(s) | 1 to 3 | 1 | 1 | 0 | 1 |
| SEQ ID NO: 20 | | | | | |
| Number of amino acids in APS | 33 | 26 | 20 | 0 | 0 |
| APS domain consists of | 0.4177 | 0.3291 | 0.2532 | 0 | 0 |
| Distribution in domain, every ( ) aa | 1 to 4 | 1 to 4 | 1 to 6 | 0 | 0 |
| Adjacent identical amino acid(s) | 1 to 3 | 1 to 2 | 1 | 0 | 0 |

*before C-terminal

The further characterization of the fusion protein of the invention can be performed in the form of the isolated, soluble proteins. The appropriate methods are known to those skilled in the art or described in the literature. Such methods include the determination of physical, biophysical and functional characteristics of the proteins. The affinity and specificity of the variants isolated can be detected by means of biochemical standard methods as discussed above and in the Examples and as known to those skilled in the art. For stability analysis, for example, spectroscopic or fluorescence-based methods in connection with chemical or thermal unfolding are known to those skilled in the art, including e.g. differential scanning fluorimetry (DSF).

Determination of binding affinity. Methods for determining binding affinities, i.e. for determining the dissociation constant $K_D$, are known to a person of ordinary skill in the art and can be selected for instance from the following methods known in the art: surface plasmon resonance (SPR) based technology, Bio-layer interferometry (BLI), enzyme-linked immunosorbent assay (ELISA), flow cytometry, fluorescence spectroscopy techniques, isothermal titration calorimetry (ITC), analytical ultracentrifugation, radioimmunoassay (RIA or IRMA), and enhanced chemiluminescence (ECL). Some of the methods are described in more detail in the Examples below. Typically, the dissociation constant $K_D$ is determined at 20° C., 25° C., or 30° C. If not specifically indicated otherwise, the $K_D$ values recited herein are determined at 22° C.+/−3° C. by surface plasmon resonance. In an embodiment of the invention, the fusion protein or the ED-B binding domain has a dissociation constant $K_D$ to ED-B in the range between 0.1 nM and 100 nM, preferably between 0.1 nM and 10 nM.

Specific examples for chemical moieties. The present invention relates to a fusion protein wherein the chemical moieties that are coupled to the coupling site of the fusion protein are selected from the group consisting of dyes, chelators, drugs, toxins, and small molecules. Examples for small molecules are low molecular weight (below about 5000 Daltons) proteins. An example for a suitable dye is EDANS (5-[(2-aminoethyl)amino]naphthalene-1-sulfonic acid).

An example for a chelator is DOTA which can be used as complexing agent for molecules with various structures, including radioisotopes. The resulting fusion protein can be used with a number of e.g. radioisotopes, in particular for a use in medical applications in diagnosis or therapy. Examples for toxins are selected from, but by no means limited to, auristatins, tubulysins, amanitins, doxorubicin, maytansines, calicheamicin, vinca alkaloids, camptothecin, and duocarmycin.

Use of the fusion protein. Fusion proteins with coupled chelators, drugs, toxins, and small molecules can be particularly useful for use in the diagnosis or treatment of cancer including breast, ovarian, prostate, non-small cell lung, colorectal, pancreatic, human skin, hepatocellular, intracraneal meningeoma, glioblastoma or for use in the diagnosis or treatment of cardiovascular diseases including atherosclerotic plaques, myocardial infarction or inflammation and others. For example, fusion protein with dyes coupled to the coupling site can be useful in the diagnosis of cancer. For example, fusion protein with chelators coupled to the coupling site can be useful in diagnostic or therapeutic applications; for example, further substances such as radioisotopes can be coupled to chelators, preferably for use in molecular imaging.

Composition of the fusion protein. The present invention also relates to a composition that comprises a fusion protein for use in medicine, preferably for use in the diagnosis or treatment of cancer or cardiovascular diseases. The invention also relates to a kit that comprises a composition of a fusion protein in a predefined amount and optionally further components such as solutions, buffers, handling devices, and others, suitable for handling the fusion protein or preparing the fusion protein for further use.

Nucleic acid molecule. In one embodiment, the present invention is directed to a nucleic acid molecule, preferably an isolated nucleic acid molecule, encoding fusion protein as disclosed above. In one embodiment, the present invention is directed to a vector comprising the nucleic acid molecule. A vector means any molecule or entity (e.g., nucleic acid, plasmid, bacteriophage or virus) that can be used to transfer protein coding information into a host cell. In one embodiment, the vector is an expression vector.

In one embodiment, the present invention is directed to an expression system which comprises a nucleic acid or a vector as disclosed above, for example a prokaryotic host cell, for example E. coli, or a eukaryotic host, for example yeast *Saccharomyces cerevisiae* or *Pichia pastoris* or mammalian cells such as CHO cells.

Method for the production of a fusion protein. The present invention is directed to a method for the production of a fusion protein of the invention, comprising the step(s): (a) culturing a suitable host cell under suitable conditions for the expression of the binding protein in order to obtain said fusion protein; and (b) optionally isolating said fusion protein. Suitable conditions for culturing a prokaryotic or eukaryotic host are well-known to the person skilled in the art.

Fusion proteins of the invention are generated artificially, generally by recombinant DNA technology well-known to a skilled person. Fusion proteins may be prepared by any of the many conventional and well-known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

In a further embodiment of the present invention the production of the alkaline stable Ig binding protein is performed by cell-free in vitro transcription/translation.

The present invention is further directed to a method for the preparation of a fusion protein of the invention, said method comprising the following steps: preparing a nucleic acid encoding a fusion protein as defined above; introducing said nucleic acid into an expression vector; introducing said expression vector into a host cell; cultivating the host cell; subjecting the host cell to culturing conditions under which a fusion protein is expressed, thereby producing a fusion protein as described above; optionally isolating the fusion protein); and optionally conjugating the fusion protein with further functional moieties as described above. Cultivation of cells and protein expression for the purpose of protein production can be performed at any scale, starting from small volume shaker flasks to large fermenters, applying technologies well-known to those skilled in the art.

EXAMPLES

The following Examples are provided for further illustration of the invention. The invention, however, is not limited thereto, and the following Examples merely show the practicability of the invention on the basis of the above description. For a complete disclosure of the invention reference is made also to the literature cited in the application which is incorporated completely into the application by reference.

Example 1. Cloning of Fusion Proteins

The genes for the desired fusion proteins were generated by GeneArt™ gene synthesis (Thermo Fisher Scientific) and cloned into a derivate of a pET28a vector (Novagen, Merck KGaA) for tag-free expression. Ligation products were transformed into *E. coli* XL2-blue cells (Agilent Technologies) via electroporation. Single colonies were screened by PCR to identify constructs containing inserts of the right size. DNA sequencing was used to verify the correct sequences of selected clones.

Example 2. Purification of Proteins

Example 2a. Expression and Purification of ED-B Binding Affilin Proteins

The genes for Affilin proteins were cloned into pPR-IBA1b and expressed as C-terminal Strep-tag II fusion protein in BL21(DE3). Protein expression was done in a 1-liter scale followed by cell disruption using ultra sonication and purification via a StrepTactin Superflow column (IBA, Goettingen, Germany) according to the instruction of the manufacturer. The second purification step was carried out as analytical size exclusion chromatography via a Superdex 75 pg 16/600 column in PBS pH 7.4.

For crystallization experiments, Affilin-138800 (SEQ ID NO: 2) was cloned as tag free protein into pET20b and subsequently transferred into electro-competent *E. coli* BL21(DE3) cells. After cell harvest and cell disruption the lysate was purified via a HiTrap Q Sepharose FF column, a HiTrap Phenyl HP and finally dialyzed against PBS pH 7.4 overnight.

The analytical size exclusion chromatography was carried out on a Superdex 75 5/150 GL column (GE Healthcare) in PBS using a Summit HPLC system (Dionex, Idstein, Germany). The apparent molecular size was calculated using the gel filtration standard (Bio-Rad Laboratories, Hercules, Calif., USA).

The purity of the protein samples was analyzed by reversed phase chromatography using an Ultimate 3000 UHPLC system (Dionex, Idstein, Germany). A PLRP-S column (Santa Clara, Calif., USA) with 5 µm particle size and 300 Å pore size was used at 55° C. The gradient was set to 10% 2-propanol, 0.1% TFA to 80% 2-propanol, 0.1% TFA.

TABLE 4

Purification of ED-B binding Affilin proteins

| SEQ ID NO: | Affilin | SE-HPLC main peak (%) | Ret. Time [min] | App. MW (kDa) | MW (kDa) | RP-HPLC main peak (%) | Ret. Time [min] | Total Area (mAU * mL) 10 mm layer thickness |
|---|---|---|---|---|---|---|---|---|
| 2 | 138800 | 100 | 5.95 | 14.43 | 18.604 | 100 | 18.88 | 10.3 |
| 5 | 181491 | 100 | 5.89 | 15.34 | 18.512 | 100 | 18.88 | 8.7 |
| 6 | 181492 | 100 | 6.15 | 11.75 | 18.547 | 100 | 20.78 | 8.7 |
| 7 | 181493 | 100 | 5.88 | 15.50 | 18.561 | 100 | 21.46 | 12.8 |
| 13 | 181494 | 100 | 6.09 | 12.50 | 18.381 | 100 | 18.41 | 10.8 |

Example 2b. Purification of ED-B Binding Fusion Proteins

The genes for the anti ED-B fusion proteins were expressed as N-terminal 6×His-SUMO fusion in BL21 (DE3). Purification was done according to the SUMO purification protocol, including Ni-agarose purification, SUMO-hydrolase cleavage, a second Ni-agarose step and a final size exclusion chromatography. The purity of the protein samples was analyzed by reversed phase chromatography using an Ultimate 3000 UHPLC system (Dionex, Idstein, Germany) and a PLRP-S column (Santa Clara, Calif., USA).

Example 3. Production of Fibronectin Fragments

The genes for the fibronectin fragments 67689 and 6789 (Uniprot ID P02751-7, sequence 1080-1538) were obtained via gene synthesis (Geneart, Regensburg, Germany) and cloned into pET28a expression vector. The vector was transferred into electro competent E. coli HMS174 (DE3) cells (Novagen, Darmstadt, Germany) for protein production of 768. For co-crystallization with Affilin molecules, another construct was used based on the fibronectin domain 7, extra domain B and domain 8. This fragment was also cloned in pET28a and transferred into E. coli BL21 (DE3) (Lucigen, Middleton, Wis., USA). After protein expression the cells were lysed and the protein was purified via a Q-Sepharose FF 26/200 column, ammonium sulfate precipitation, a Phenyl HP column and a final size exclusion on a Superdex 75 26/600 column. All chromatographic steps were carried out on an Aekta Explorer system (GE Healthcare).

For labeling of the fragment 67689 with biotin the sample was dialyzed against 50 mM sodium phosphate buffer pH 6.5 to obtain a preferred N-terminal biotinylation. The target protein 67689 was incubated with a 30-fold molar excess of EZ-Link Sulfo-NHS-LC-Biotin reagent (Pierce, Rockford, Ill., USA) for 24 hours at 4° C. Subsequently the solution was dialyzed against PBS pH 7.4 to remove non-coupled biotin.

Example 4. Analysis of Serum Stability of ED-B Binding Proteins Via Concentration Dependent ELISA The ELISA was carried out in 96-well medium binding plates (Microlon 200, Greiner Bio-One, Kremsmuenster, Austria). Coating with target 67689 and off-target 6789 (both 5 µg/ml in PBS) was performed by overnight incubation at 4° C. The wells were then washed with PBST and blocked with 3% BSA solution for 2 h at room temperature. Various concentrations of Affilin protein were applied on target coated plates in mouse serum for 1 and 24 h at 37° C. Between all incubation steps the wells were washed 3-fold with PBST. For detection of Affilin binding to 67689 anti-Ubi-antibody and anti-IgG-POD were used, followed by TMB Plus (Kem-En-Tec Diagnostics, Taastrup, Denmark) incubation. Measuring the absorbance at 450 nm was carried out with a Sunrise microplate reader (Tecan, Maennedorf, Switzerland). FIG. 3 shows that the binding affinity of Affilin-77404, Affilin-138800, and Affilin-138801 is not affected in mouse serum for 1 and 24 h.

Example 5. Analysis of Serum Stability of ED-B Binding Proteins Via SPR

Figure 4B:
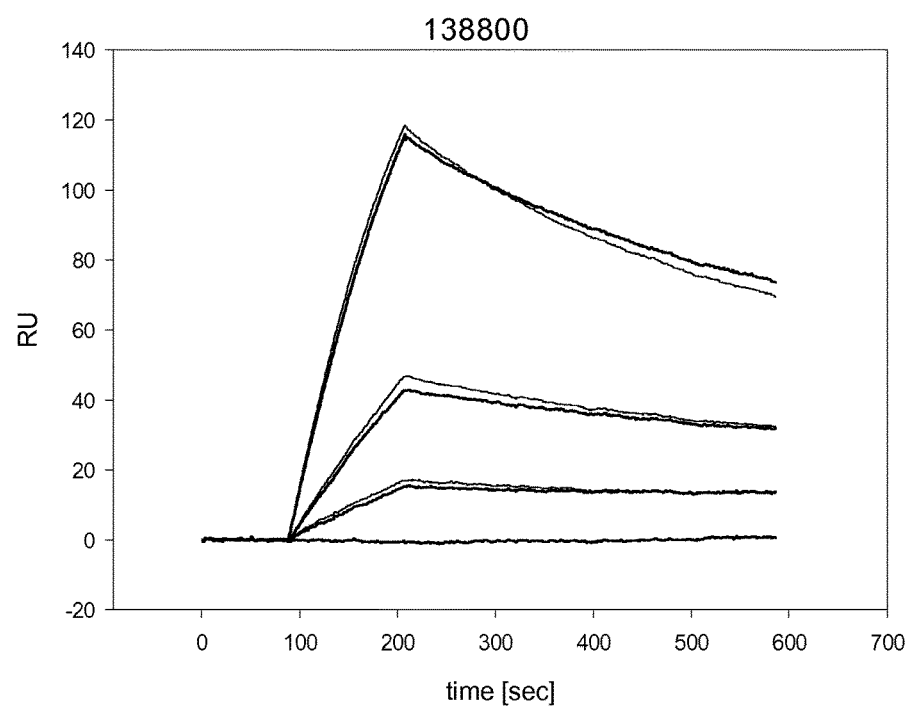
FIG. 4B. Binding kinetics of Affilin-138800 in serum or PBS. Incubation in serum, thin line; incubation PBS, thick line.

After serum incubation, surface plasmon resonance (SPR) measurements on a Biacore 3000 (GE Healthcare) were used to determine the binding behavior of Affilin-138800 and Affilin-77404 to target 67689 and off-target 6789. The protein was captured from serum incubation after 1 h and 24 using streptactin matrix (IBA, Goettingen). Biotinylated target and off target were immobilized on a streptavidin chip (GE Healthcare) followed by concentration dependent injection of Affilin molecules (0-500 nM) in PBST. All 67689-traces were corrected by subtraction of the 6789 flow channel. $K_D$, $k_{on}$ and $K_{off}$ values were calculated by fitting the traces using a global kinetic fitting (1:1 Langmuir model, BIAevaluation 3.0 software). Results are shown in FIG. 4 and Table 5. Evaluated dissociation constants ($K_D$) were standardized against off-target and indicated.

Example 6. Thermal Stability

Thermal transition of proteins was measured via differential scanning fluorimetry (DSF). DSF measurements were performed with a protein concentration of 0.1 mg/ml protein in PBS pH 7.4 and a 10-fold dilution of SYPRO Orange (Invitrogen, Carlsbad, Calif., USA) in a real-time PCR device (Light Cycler 480, Roche Diagnostics, Mannheim, Germany). The fluorescence was measured at 465 nm excitation and 580 nm emission. For all measurements a temperature range of 20-90° C. with 1 K/min increment was analyzed. The fluorescence raw data was plotted against the temperature. The inflexion point ($T_m$) was derived from the maximum of the first deviation of the fluorescence curve. Results are shown in FIG. 8 and Table 5.

TABLE 5

Biochemical characterization of Affilin proteins.

| SEQ ID NO: | Affilin | DSF App. Tm (° C.) | Biacore Kon (1/Ms) | Koff (1/s) | KD |
|---|---|---|---|---|---|
| 2 | 138800 | 59.73 | 1.24E+06 | 7.83E−04 | 634 pM |
| 5 | 181491 | 61.54 | 9.69E+05 | 6.87E−02 | 71.1 nM |
| 6 | 181492 | 57.48 | 1.52E+06 | 6.65E−03 | 4.37 nM |
| 7 | 181493 | 51.45 | 1.93E+06 | 6.91E−03 | 3.59 nM |
| 13 | 181494 | 69.38 | 1.64E+06 | 1.18E−03 | 725 pM |
| 3 | 138801 | 60.38 | 1.63E+06 | 1.51E−03 | 925 pM |
| 53 | 190761 | 59.90 | 5.83E+06 | 3.73E−03 | 638 pM |
| 35 | 181490 | 59.6 | 1.54E+06 | 9.48E−04 | 615 pM |
| 51 | 184169 | 59.4 | 5.05E+05 | 1.62E−03 | 3.22 nM |
| 50 | 184168 | 65.5 | 4.19E+05 | 1.22E−03 | 2.91 nM |

Example 7. Analysis of Secondary Structure of Affilin-138800 (CD-Spectroscopy)

Far-UV circular dichroism (CD) experiments on a Jasco J-810 spectropolarimeter (Jasco, Gross-Umstadt, Germany) were used to analyze the secondary structure of the Affilin variants. The proteins diluted in PBS pH 7.4 were measured from 190 to 250 nm at 20° C. in a 0.1 mm quartz cuvette. A scanning rate of 50 nm per minute at a bandwidth of 1 nm was used. An average of 30 spectra per probe was used and all spectra were buffer corrected.

Example 8. Protein Crystallization and Structure Determination

Affilin-138800 (SEQ ID NO: 2, as tag free protein) and fibronectin fragment 7B8 were equimolar incubated at room temperature for 1 h and the protein complex was then purified via size exclusion chromatography (Superdex 75, 26/600) in 10 mM HEPES, 100 mM NaCl pH 7.3. The purified complex was concentrated up to 21.8 mg/ml. In order to assess the molecular ratio of the 7B8-Affilin complex an analytical SE-HPLC was run using a Superdex 200 5/150 GL column in 10 mM HEPES, 100 mM NaCl pH 7.3. The screening for initial crystallization conditions of the complex was achieved at 15° C. using a semi-automated pipetting robot (Cartesian Microsys 4000, Zinsser Analytic, Germany). For the sitting drop crystallization 200 nl of the protein solution were added to 200 nl of the reservoir solution from the commercial screening kits (768 conditions, Jena Bioscience, Jena, Germany; Sigma Aldrich, Steinheim, Germany).

The X-ray diffraction properties of the crystals were analyzed at −180° C. using an X-ray source with a rotation anode (Micromaxx 007 generator, Rigaku, Japan) and a CCD detector (Saturn 944+, Rigaku, Japan). Subsequently the crystals were frozen for a data collection at the BESSY II synchrotron (Helmholtz Center, Berlin, Germany). The datasets were collected using a hybrid pixel detector (Pilatus 6M, Dectris, Switzerland) and de diffraction images were analyzed and processed with the XDS software package. The phase problem was solved by Molecular Replacement with the program PHASER. The model building was carried out by using the program COOT and refined with PHENIX. For the structure validation MOLPROBITY was used.

Figure 5A:
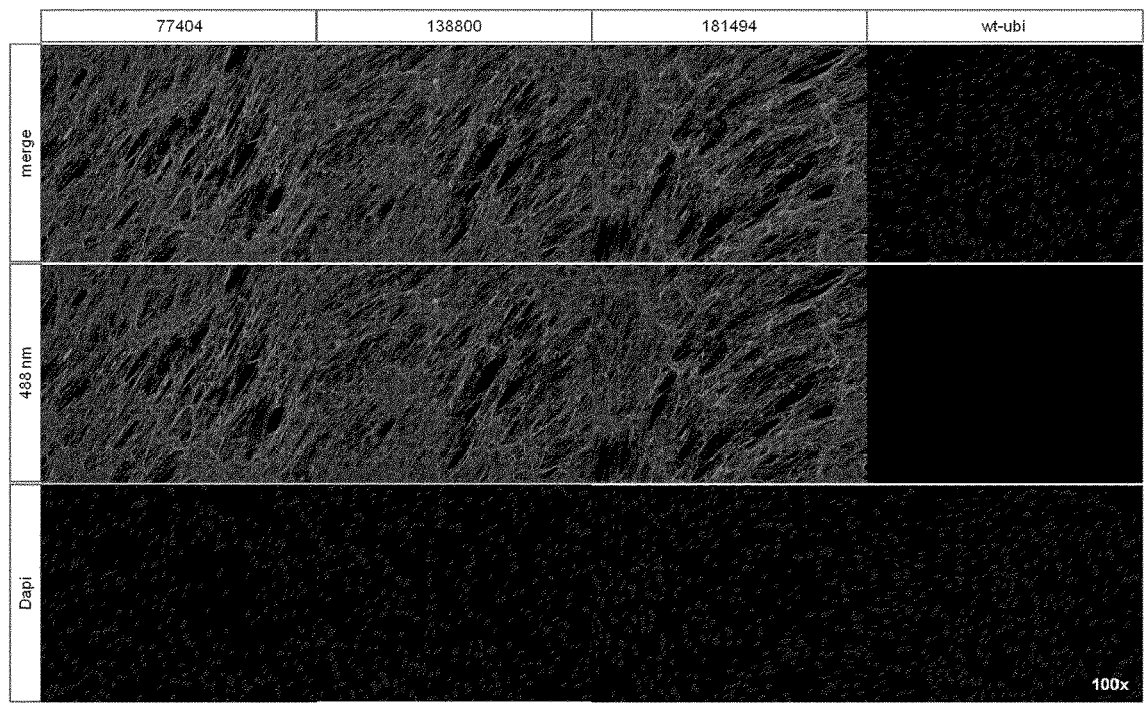
FIG. 5. Analysis of 100 nM Affilin-77404, Affilin-138800, Affilin-181494 and wt-ubi (FIG. 5A) or Affilin-190761, Affilin-138800, and wt-ubi (FIG. 5B) by immunological staining on of ED-B expressing human cells (Wi38). Shown is the specific ED-B binding of 100 nM Affilin-77404, Affilin-138800, Affilin-181494, and Affilin-190761, and no binding of wildtype ubiquitin.
Figure 5B:
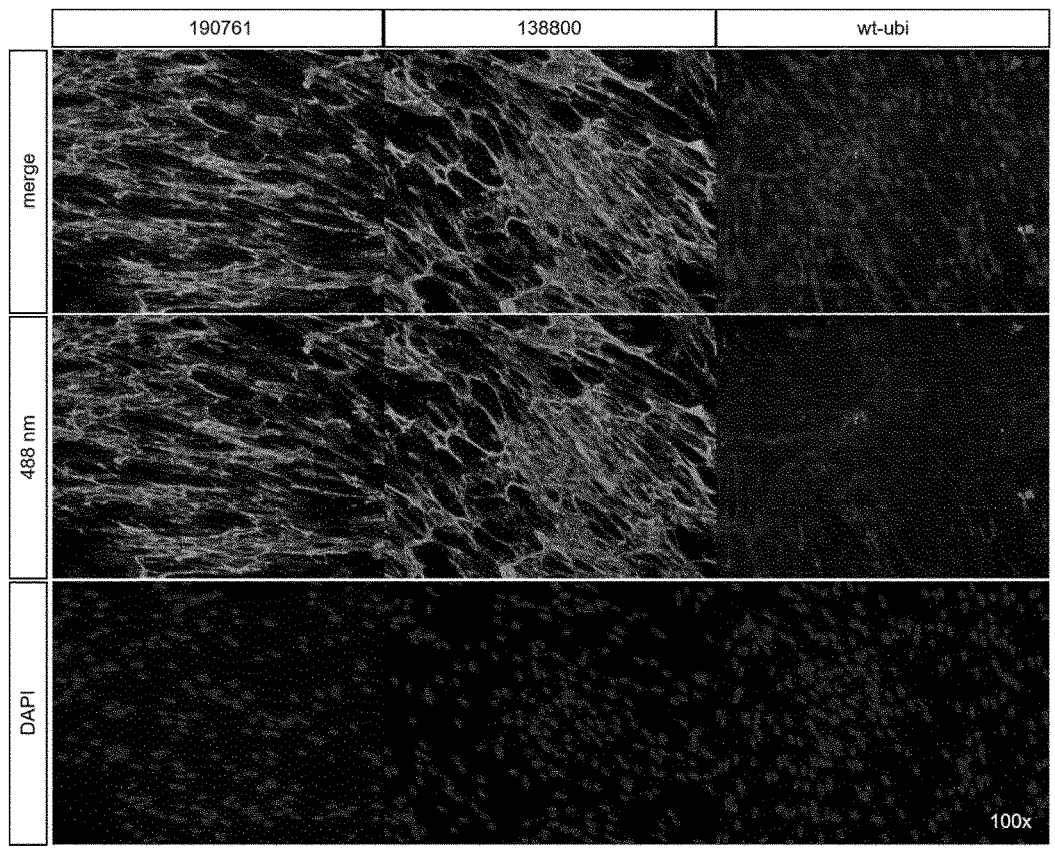

Example 9. Functional Characterization: Immunofluorescence Staining of Different Anti-EDB-Affilins High ED-B-expressing Wi38-cells and low ED-B-expressing NHDF-cells were seeded in Poly-D-Lysin-coated Chamber-Slides (Sigma-Aldrich). After cultivation for 72 h the cells were fixed with ice cold methanol for 5 min at −20° C. and blocked with 5% Horse serum/PBS for 1 h at room temperature (rt). Affilin-77404, Affilin-138800, Affilin-181494, Affilin-190761 or wt-ubi (SEQ ID NO: 31) were incubated on cells at concentrations of 100 nM, 10 nM and 1 nM. After incubation for 1 h the cells were washed 3 times with PBS and incubated with anti-StrepTag-antibody for 1 h at rt and then with anti-rabbit-IgG-Alexa488-antibody (1:1000) for 1 h at rt. Nuclei were stained with 4 μg/ml DAPI for 5 min at rt. FIG. 5 shows strong binding of Affilin-77404, Affilin-138800, Affilin-190761 and Affilin-181494 at a concentration of 100 nM on ED-B expressing Wi38-cells. No staining with the ubiquitin control was obtained. The Affilin proteins show weak specific staining on NHDF-cells (data not shown).

Example 10. Functional Characterization: Serum Stability (Fluorescence Assay)

Figure 6:
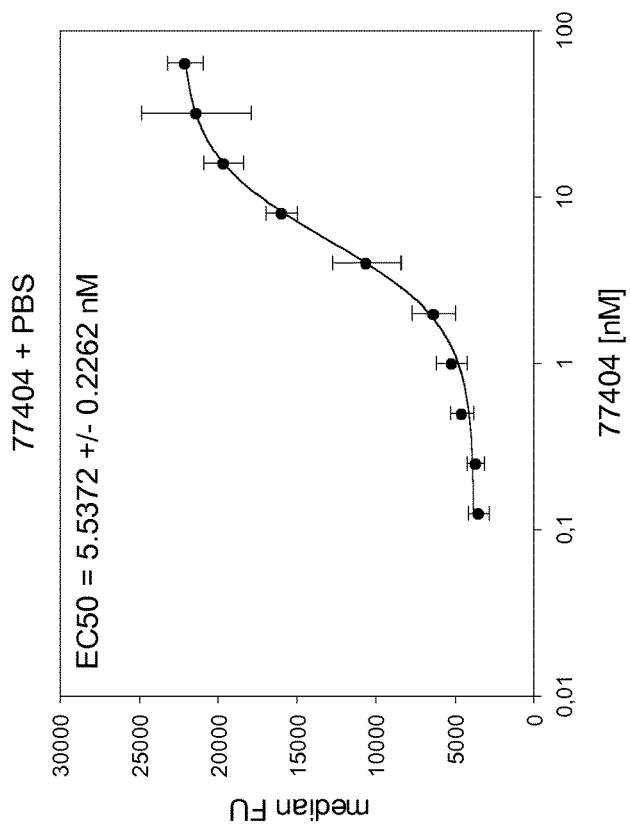
FIG. 6. Analysis of serum stability of ED-B specific Affilin proteins. Binding was measured after incubation of the variants under different conditions and subsequent immunological staining of ED-B expressing human cells (Wi38).
Figure 6:
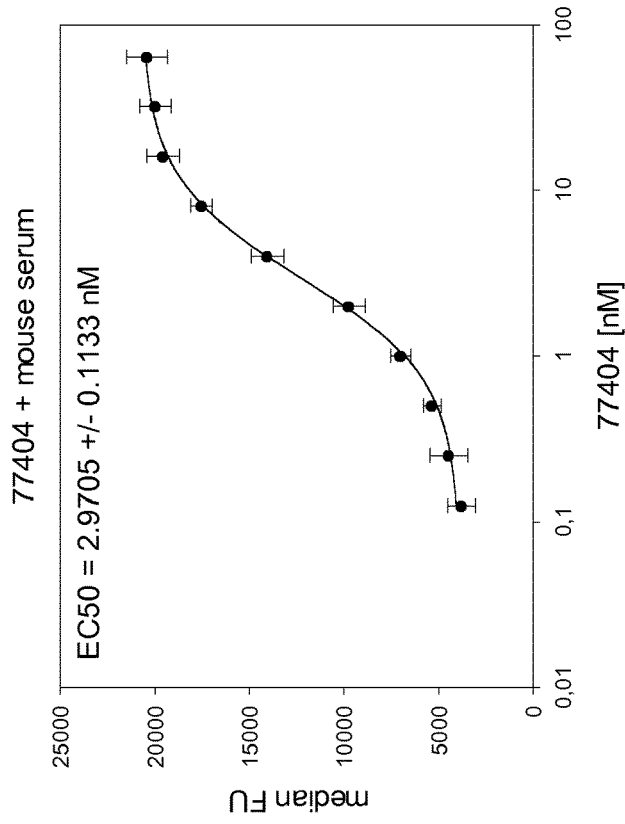
Figure 6:
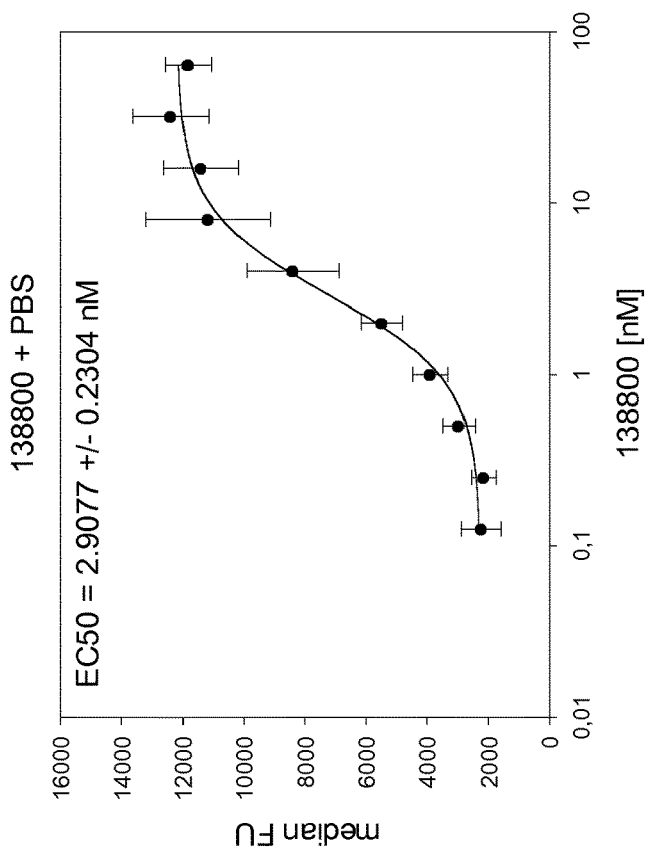
Figure 6:
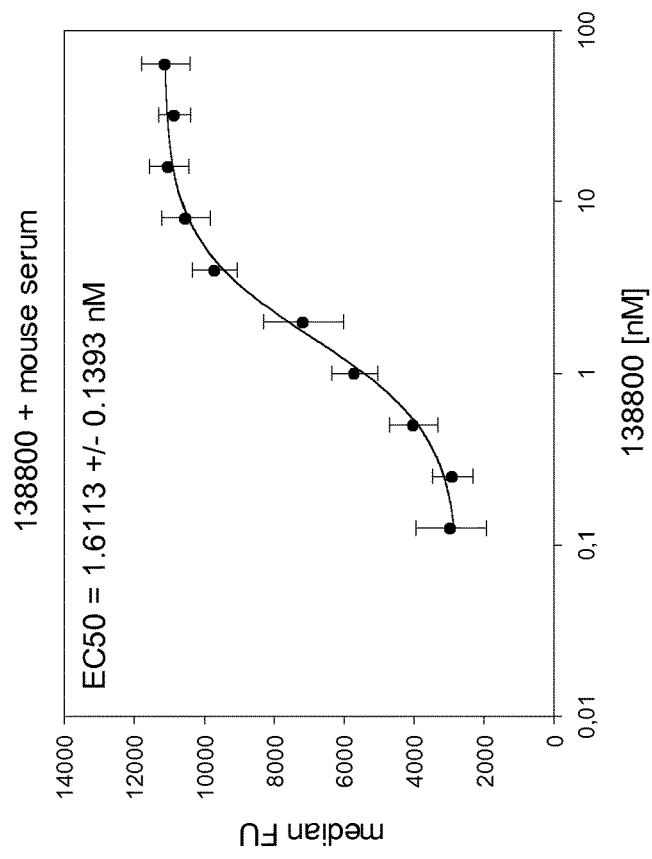
Figure 6:
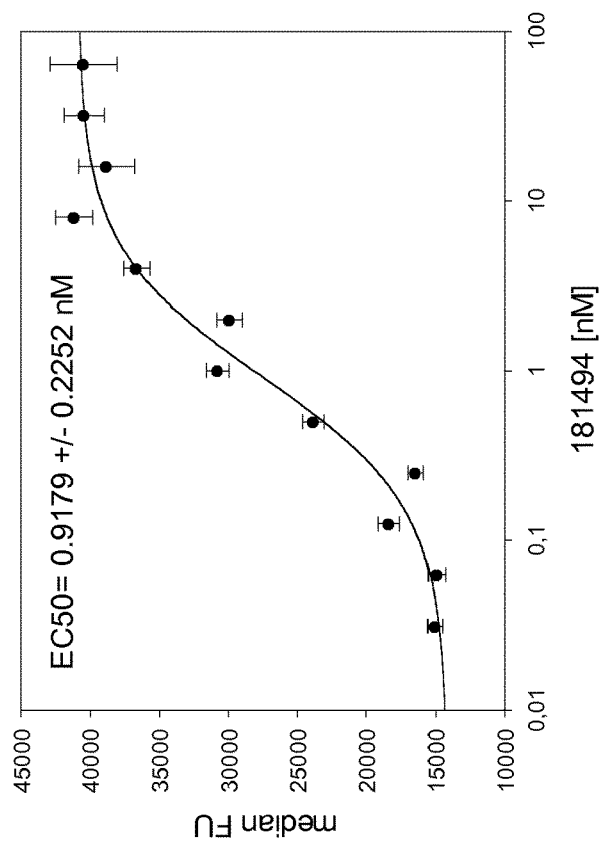
Figure 6:
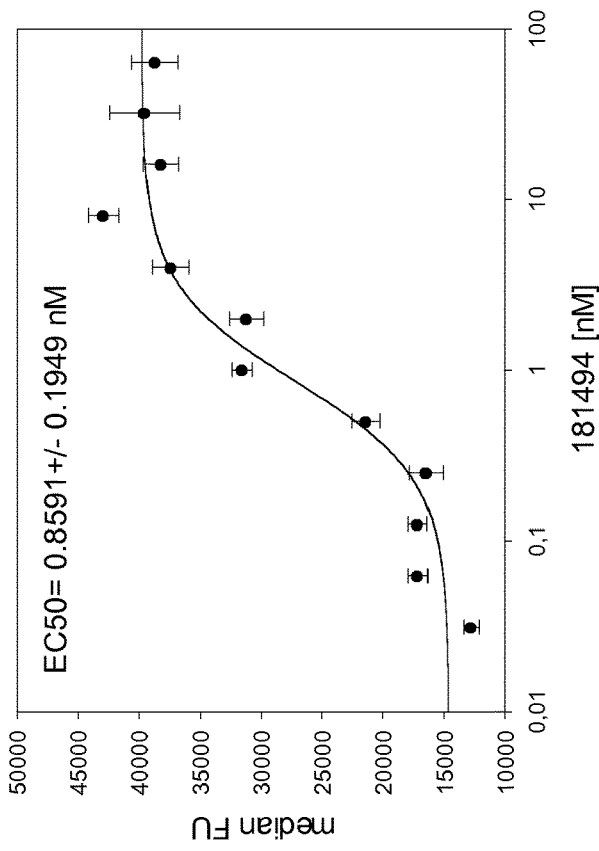
Figure 6G:
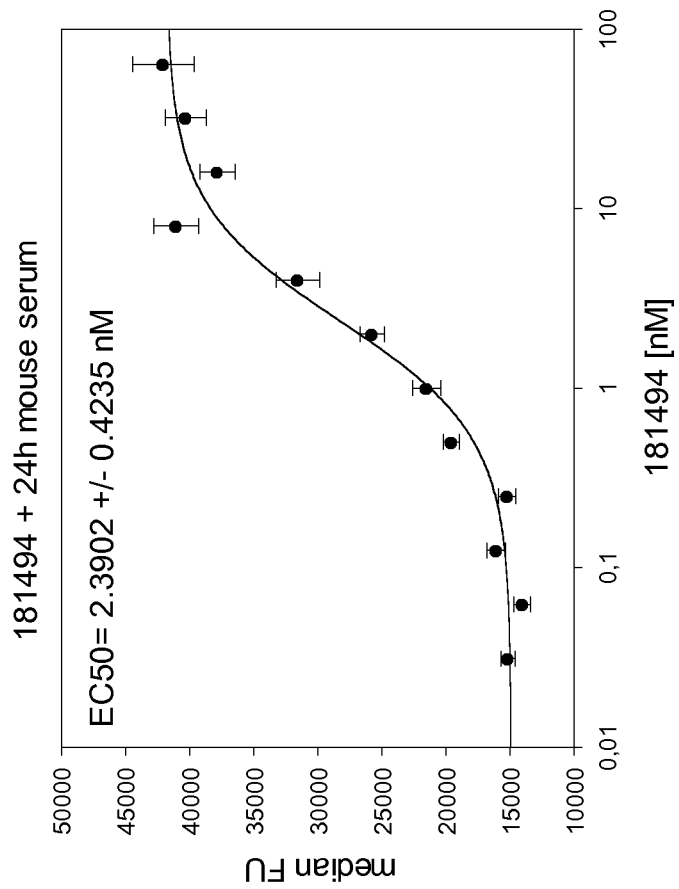

Wi38-cells were seeded in a Poly-D-Lysin-coated 96-well plate and grown for 72 h at 37° C. and 5% $CO_2$. Affilin-77404 or Affilin-138800 was incubated at a concentration of 64 nM in mouse serum or PBS for 24 h at 37° C. Affilin-181494 was incubated in mouse serum at 37° C. for 1 h and 24 h respectively. Affilin-181494 without serum incubation (0 h) was used as control. Dilution series of Affilin-77404, or Affilin-138800 in PBS and dilution series of Affilin-181494 in mouse serum were incubated on ice-cold Methanol-fixed and blocked (5% Horse-Serum/PBS) cells for 1 h at rt. Affilin binding was detected by incubation with rabbit anti-StrepTag-antibody (1:500) for 1 h and subsequently with anti-rabbit-IgG-Alexa488-antibody (1:1000) for 1 h. Fluorescence was measured with a Tecan Infinite Pro 200 plate reader at an excitation wavelength of 488 nm and emission wavelength of 520 nm. FIG. 6 A-D show no decrease of binding of Affilin-77404 or Affilin-138800 on cells after 24 h in mouse serum compared to PBS incubation; thus, Affilin-77404 and Affilin-138800 are stable in mouse serum. FIG. 6 E-F show no decrease of stability of Affilin-181494 after 1 h serum incubation and only a slight decrease after 24 h incubation in mouse serum.

Example 11. Functional Characterization: Serum Stability (Microscopy)

Wi38-cells were seeded at a concentration of 60.000 cells/ml in Poly-D-Lysin-coated Lab-Tek® Chamber-Slides (Sigma-Aldrich) and cultivated for 72 h at 37° C. 500 nM of Affilin-138800, Affilin-138801, Affilin-77404 or wt-ubi (SEQ ID NO: 31) were incubated in mouse serum for 1 h, 3 h or 24 h at 37° C. To investigate the serum stability, methanol fixed and blocked cells were incubated with 10 or 100 nM of serum treated Affilin proteins for 1 h at rt. After incubation with anti-StrepTag-antibody (1:500) and anti-rabbit-IgG-Alexa488 (1:1000) for 1 h at rt respectively, the nuclei were stained with 4 μg/ml DAPI. Analysis was done by microscopy and is summarized in Table 6. Table 6 shows the rating of the staining intensity of Affilin proteins 138800, 138801, 77404, and wt-ubi. Affilin-138800 and Affilin-77404 show strong binding after 1 h or 24 h in mouse serum. Affilin-138801 shows slightly decreased binding after 24 h incubation in serum.

TABLE 6

| ED-B Affilin proteins are stable in mouse serum. strong binding: +++; medium binding: ++; low binding: + | | | |
|---|---|---|---|
| Affilin | incubation time | c in nM | Wi38 |
| 138800 | 0 h Serum | 10 | ++ |
| | | 100 | ++ |
| | 3 h Serum | 10 | ++ |
| | | 100 | ++ |
| | 24 h Serum | 10 | ++ |
| | | 100 | ++ |
| 138801 | 0 h Serum | 10 | +++ |
| | | 100 | +++(+) |
| | 3 h Serum | 10 | +++ |
| | | 100 | +++ |
| | 24 h Serum | 10 | ++ |
| | | 100 | ++ |
| 77404 | 0 h Serum | 10 | ++ |
| | | 100 | ++ |
| | 3 h Serum | 10 | ++ |
| | | 100 | ++ |
| | 24 h Serum | 10 | ++ |
| | | 100 | ++ |
| wt-ubi | 0 h Serum | 10 | — |
| | | 100 | — |
| | 3 h Serum | 10 | — |
| | | 100 | — |
| | 24 h Serum | 10 | — |
| | | 100 | — |

FIG. 7 shows binding of 100 nM Affilin-138800 (column 1 and 2) and wt-ubi (column 3 and 4) on Wi-38-cells after 24 h incubation in mouse-serum (column 1, 3) or PBS (column 2, 4). Affilin-138800 shows a strong binding on extracellular matrix of Wi38-cells. The wild-type control shows no binding.

Example 12. EC50 Determination on Wi38-Cells

Poly-D-Lysin-coated 96-well plates were used to Wi38-cells with 60000 cells/ml per well. The cells were grown for 72 h at 37° C. and 5% $CO_2$, fixed with methanol for 5 min and blocked with 5% horse serum. Cells were incubated with dilution series of Affilin-138800 or Affilin-190761 in PBS with a start concentration of 200 nM for 45 min at rt. The binding of Affilin was detected by incubation with rabbit anti-StrepTag-antibody (1:500) and anti-rabbit-IgG-Alexa488-antibody (1:1000) for 1 h at rt. The measurements were done with a Tecan Infinite pro 200 plate reader.

Figure 9A:
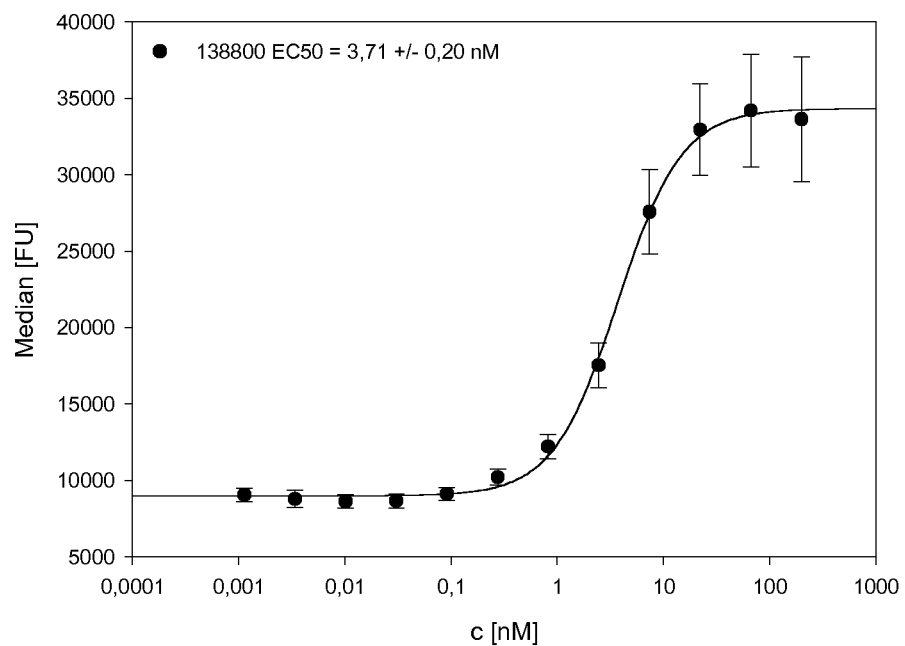
FIG. 9. EC50 determination of Affilin-138800 (FIG. 9A) and of Affilin-190761 (FIG. 9B) on Wi38-cells.
Figure 9B:
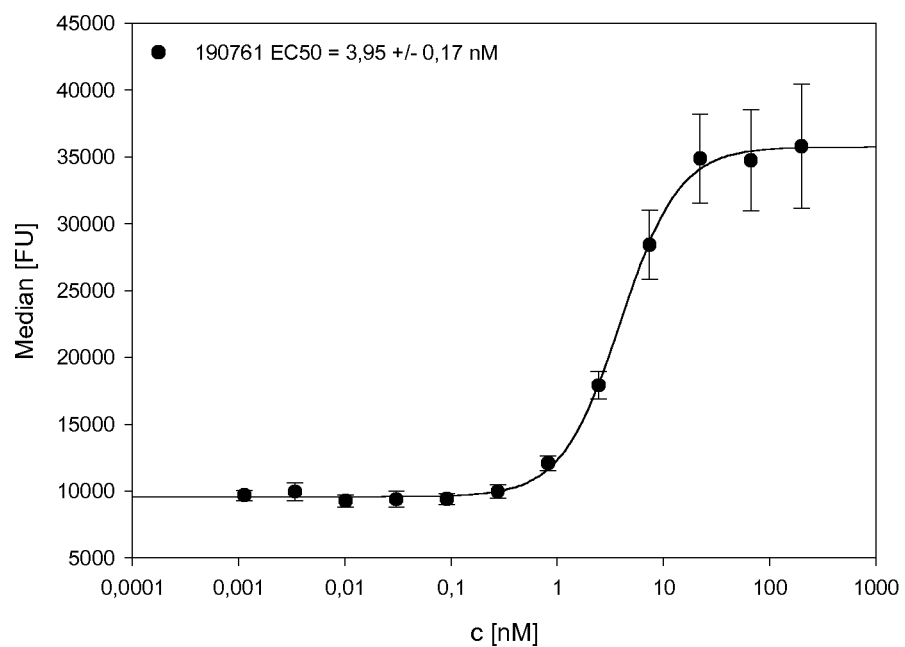

FIG. 9 shows EC50 determination of Affilin-138800 (FIG. 9A) and of Affilin-190761 (FIG. 9B) on Wi38-cells. The EC50 of Affilin-190761 is similar to Affilin-138800 with 4 nM.

The invention claimed is:

1. A fibronectin extracellular domain B (ED-B) binding protein comprising an amino acid sequence at least 90% identical to SEQ ID NO: 2, wherein the fibronectin ED-B binding protein comprises:
   (i) a histidine (H) at the position corresponding to position 6 of the wild-type sequence of SEQ ID NO: 32;
   (ii) an aspartic acid (D), arginine (R), threonine (T), or tryptophan (W) at the position corresponding to position 8 of SEQ ID NO: 32;
   (iii) a glutamine (Q), or proline (P) at the position corresponding to position 38 of SEQ ID NO: 32;
   (iv) an aspartic acid (D), alanine (A), glutamine (Q), or asparagine (N), or a deletion at the position corresponding to position 62 of SEQ ID NO: 32;
   (v) a proline (P), histidine (H), lysine (K), glycine (G), tryptophan (W), or a deletion at the position corresponding to position 63 of SEQ ID NO: 32;
   (vi) a glutamine (Q), lysine (K), valine (V), at the position corresponding to position 64 of SEQ ID NO: 32;
   (vii) a leucine (L), lysine (K), proline (P), serine (S), or arginine (R) at the position corresponding to position 65 of SEQ ID NO: 32;
   (viii) a lysine (K), glutamine (Q), histidine (H), or methionine (M) at the position corresponding to position 66 of SEQ ID NO: 32;
   (ix) a threonine (T), glutamine (Q), methionine (M), or leucine (L) at the position corresponding to position 85 of SEQ ID NO: 32;
   (x) a glutamine (Q), methionine (M), arginine (R), or tryptophan (W) at the position corresponding to position 87 of SEQ ID NO: 32;
   (xi) a deletion at the position corresponding to position 141 of SEQ ID NO: 32;
   (xii) an aspartic acid (D) at the position corresponding to position 142 of SEQ ID NO: 32;
   (xiii) a tyrosine (Y), tryptophan (W), or alanine (A) at the position corresponding to position 143 of SEQ ID NO: 32;
   (xiv) an arginine (R) at the position corresponding to position 144 of SEQ ID NO: 32; and
   (xv) a phenylalanine (F), tryptophan (W), or tyrosine (Y) at the position corresponding to position 145 of the wild-type sequence of SEQ ID NO: 32,
and wherein the ED-B binding protein or variant thereof has a binding affinity to the extracellular domain B of fibronectin of 10 nM or less in serum after incubation for at least 20 hours.

2. The fibronectin ED-B binding protein of claim 1, further comprising one or more chemical moieties conjugated thereto via an added C-terminal cysteine, and further wherein the one or more chemical moieties are selected from the group consisting of chelators, drugs, toxins, dyes, and small molecules.

3. A method for producing the fibronectin ED-B binding protein of claim 1, the method comprising culturing a host cell comprising a nucleic acid sequence that encodes the fibronectin ED-B binding protein of claim 1 under conditions wherein the nucleic acid sequence is expressed in the host cell, whereby the protein of claim 1 is produced in the host cell.

4. The method of claim 3, wherein the chemical moiety is a chelator that can function as a complexing agent for coupling of one or more additional substances.

5. The method of claim 4, wherein the chelator can function as a complexing agent for coupling of a radioisotope.

6. The protein of claim 1, wherein the protein comprises the amino acid sequence of any one of SEQ ID NOs: 2-13 and 53.

7. A method for diagnosing and/or treating a cancer or cardiovascular disease in a subject in need thereof, the method comprising administering to the subject a therapeutically effective amount of a composition comprising the fibronectin ED-B binding protein of claim 1.

8. The method of claim 7, wherein the cancer is selected from the group consisting of breast cancer, non-small cell lung cancer, ovarian cancer, prostate cancer, colorectal cancer, pancreatic cancer, human skin cancer, hepatocellular cancer, intracranial meningioma, and glioblastoma.

9. The method of claim 7, wherein the cardiovascular disease is associated with atherosclerotic plaques, myocardial infarction, or inflammation.

10. A method for molecular imaging, the method comprising:
   (a) administering to a subject a composition comprising the fibronectin ED-B binding protein of claim 1 coupled to a detectable moiety; and
   (b) detecting the detectable moiety.

* * * * *

SEQUENCE LISTING

<160> NUMBER OF SEQ ID NOS: 52

<210> SEQ ID NO 1
<211> LENGTH: 155
<212> TYPE: PRT
<213> ORGANISM: Artificial Sequence
<220> FEATURE:
<223> OTHER INFORMATION: Artificially synthesized Affilin-77404

<400> SEQUENCE: 1

```
Met Arg Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Pro Lys
    50                  55                  60

Leu Ser Leu His Leu Val Leu Arg Leu Arg Ala Ala Gly Ile Gly Met
65                  70                  75                  80

Gln Ile Phe Val His Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Trp Gln Ala
    130                 135                 140

Pro Leu His Leu Val Leu Arg Leu Arg Ala Ala
145                 150                 155
```

<210> SEQ ID NO 2
<211> LENGTH: 153
<212> TYPE: PRT
<213> ORGANISM: Artificial Sequence
<220> FEATURE:
<223> OTHER INFORMATION: Artificially synthesized Affilin-138800

<400> SEQUENCE: 2

```
Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
    50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu
            100                 105                 110

Gly Ile Pro Pro Asp Gln Gln Arg Leu Ile Trp Ala Gly Lys Gln Leu
        115                 120                 125

Glu Asp Gly Arg Thr Leu Ser Asp Tyr Asn Ile Asp Tyr Arg Phe Leu
    130                 135                 140
```

His Leu Val Leu Arg Leu Arg Ala Ala
145                 150

<210> SEQ ID NO 3
<211> LENGTH: 154
<212> TYPE: PRT
<213> ORGANISM: Artificial Sequence
<220> FEATURE:
<223> OTHER INFORMATION: Artificially synthesized Affilin-138801

<400> SEQUENCE: 3

Met Gln Ile Phe Val His Thr Asp Thr Gly Lys Thr Ile Thr Leu Glu
1               5                   10                  15

Val Glu Pro Ser Asn Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
    50                  55                  60

Leu Lys Leu His Leu Val Arg Leu Arg Ala Ala Gly Ile Gly Ile
65                  70                  75                  80

Gln Thr Phe Val Thr Thr Gln Thr Gly Glu Thr Ile Thr Leu Glu Val
                85                  90                  95

Glu Pro Ser Asp Thr Ile Glu Asn Val Lys Ala Lys Ile Gln Asp Lys
            100                 105                 110

Val Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Asp Tyr Arg Tyr
    130                 135                 140

Leu His Leu Val Leu Arg Leu Arg Ala Ala
145                 150

<210> SEQ ID NO 4
<211> LENGTH: 154
<212> TYPE: PRT
<213> ORGANISM: Artificial Sequence
<220> FEATURE:
<223> OTHER INFORMATION: Artificially synthesized Affilin-102472

<400> SEQUENCE: 4

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
    50                  55                  60

Leu Lys Leu His Leu Val Leu Arg Leu Arg Ala Ala Gly Ile Gly Met
65                  70                  75                  80

Gln Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Asp Tyr Arg Tyr
    130                 135                 140

```
Leu His Leu Val Leu Arg Leu Arg Ala Ala
145                 150
```

<210> SEQ ID NO 5
<211> LENGTH: 153
<212> TYPE: PRT
<213> ORGANISM: Artificial Sequence
<220> FEATURE:
<223> OTHER INFORMATION: Artificially synthesized Affilin-138800 Y141A

<400> SEQUENCE: 5

```
Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
    50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu
            100                 105                 110

Gly Ile Pro Pro Asp Gln Gln Arg Leu Ile Trp Ala Gly Lys Gln Leu
        115                 120                 125

Glu Asp Gly Arg Thr Leu Ser Asp Tyr Asn Ile Asp Ala Arg Phe Leu
    130                 135                 140

His Leu Val Leu Arg Leu Arg Ala Ala
145                 150
```

<210> SEQ ID NO 6
<211> LENGTH: 153
<212> TYPE: PRT
<213> ORGANISM: Artificial Sequence
<220> FEATURE:
<223> OTHER INFORMATION: Artificially synthesized Affilin-138800 RAGL

<400> SEQUENCE: 6

```
Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
    50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu
            100                 105                 110

Gly Ile Pro Pro Asp Gln Gln Arg Leu Ile Trp Ala Gly Lys Gln Leu
        115                 120                 125

Glu Asp Gly Arg Thr Leu Ser Asp Tyr Asn Ile Asp Tyr Arg Phe Leu
```

His Leu Val Leu Arg Leu Gly Leu Ala
145                 150

<210> SEQ ID NO 7
<211> LENGTH: 153
<212> TYPE: PRT
<213> ORGANISM: Artificial Sequence
<220> FEATURE:
<223> OTHER INFORMATION: Artificially synthesized Affilin-138800 RAAL

<400> SEQUENCE: 7

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Gln Asp Gln Gln Arg Leu Ile Trp Ala Gly Lys
            35                  40                  45

Gln Leu Glu Asp Gly Arg Thr Leu Ser Asp Tyr Asn Ile Asp Pro Gln
50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu
                100                 105                 110

Gly Ile Pro Pro Asp Gln Gln Arg Leu Ile Trp Ala Gly Lys Gln Leu
            115                 120                 125

Glu Asp Gly Arg Thr Leu Ser Asp Tyr Asn Ile Asp Tyr Arg Phe Leu
    130                 135                 140

His Leu Val Leu Arg Leu Ala Leu Ala
145                 150

<210> SEQ ID NO 8
<211> LENGTH: 151
<212> TYPE: PRT
<213> ORGANISM: Artificial Sequence
<220> FEATURE:
<223> OTHER INFORMATION: Artificially synthesized Affilin-138800 2274-4

<400> SEQUENCE: 8

Met Gln Ile Phe Val His Thr Trp Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Gln Asp Gln Gln Arg Leu Ile Trp Ala Gly Lys
            35                  40                  45

Gln Leu Glu Asp Gly Arg Thr Leu Ser Asp Tyr Asn Ile Asn Trp Val
50                  55                  60

Arg Gln Leu His Leu Val Leu Arg Leu Arg Ala Ala Met Gln Ile Phe
65                  70                  75                  80

Val Leu Thr Trp Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Asp Tyr Arg Trp Leu His Leu
            130                 135                 140

Val Leu Arg Leu Arg Ala Ala
145                 150

<210> SEQ ID NO 9
<211> LENGTH: 151
<212> TYPE: PRT
<213> ORGANISM: Artificial Sequence
<220> FEATURE:
<223> OTHER INFORMATION: Artificially synthesized Affilin-138800 2274-42

<400> SEQUENCE: 9

Met Gln Ile Phe Val His Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asn Trp Val
    50                  55                  60

Arg Gln Leu His Leu Val Leu Arg Leu Arg Ala Ala Ile Gln Ile Phe
65                  70                  75                  80

Val Leu Thr Trp Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Asp Tyr Arg Trp Leu His Leu
    130                 135                 140

Val Leu Arg Leu Arg Ala Ala
145                 150

<210> SEQ ID NO 10
<211> LENGTH: 151
<212> TYPE: PRT
<213> ORGANISM: Artificial Sequence
<220> FEATURE:
<223> OTHER INFORMATION: Artificially synthesized Affilin-138800 2274-43

<400> SEQUENCE: 10

Met Gln Ile Phe Val His Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asn Trp Val
    50                  55                  60

Arg Gln Leu His Leu Val Leu Arg Leu Arg Ala Ala Met Gln Ile Phe
65                  70                  75                  80

Val Leu Thr Trp Thr Gly Lys Thr Ile Thr Leu Gly Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Asp Tyr Arg Trp Leu His Leu
        130                 135                 140

Val Leu Arg Leu Arg Ala Ala
145                 150

<210> SEQ ID NO 11
<211> LENGTH: 151
<212> TYPE: PRT
<213> ORGANISM: Artificial Sequence
<220> FEATURE:
<223> OTHER INFORMATION: Artificially synthesized Affilin-138800 2273-31

<400> SEQUENCE: 11

Met Gln Ile Phe Val His Thr Thr Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Gln Gly Val
    50                  55                  60

Arg Met Leu His Leu Val Leu Arg Leu Arg Ala Ala Met Gln Ile Phe
65                  70                  75                  80

Val Met Thr Arg Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Asp Tyr Arg Trp Leu His Leu
    130                 135                 140

Val Leu Arg Leu Arg Ala Ala
145                 150

<210> SEQ ID NO 12
<211> LENGTH: 151
<212> TYPE: PRT
<213> ORGANISM: Artificial Sequence
<220> FEATURE:
<223> OTHER INFORMATION: Artificially synthesized Affilin-138800 2273-32

<400> SEQUENCE: 12

Met Gln Ile Phe Val His Thr Arg Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Ala His Gln
    50                  55                  60

Pro Gln Leu His Leu Val Leu Arg Leu Arg Ala Ala Met Gln Ile Phe
65                  70                  75                  80

Val Gln Thr Met Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp

```
                    115                 120                 125

Gly Arg Thr Leu Ser Asp Tyr Asn Ile Asp Tyr Arg Tyr Leu His Leu
    130                 135                 140

Val Leu Arg Leu Arg Ala Ala
145                 150

<210> SEQ ID NO 13
<211> LENGTH: 151
<212> TYPE: PRT
<213> ORGANISM: Artificial Sequence
<220> FEATURE:
<223> OTHER INFORMATION: Artificially synthesized Affilin-181494 (del
      62/63)

<400> SEQUENCE: 13

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Gln Asp Gln Gln Arg Leu Ile Trp Ala Gly Lys
            35                  40                  45

Gln Leu Glu Asp Gly Arg Thr Leu Ser Asp Tyr Asn Ile Gln Lys Lys
50                  55                  60

Ser His Leu Val Leu Arg Leu Arg Ala Ala Gly Gly Met Gln Ile Phe
65                  70                  75                  80

Val Thr Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Asp Tyr Arg Phe Leu His Leu
    130                 135                 140

Val Leu Arg Leu Arg Ala Ala
145                 150

<210> SEQ ID NO 14
<211> LENGTH: 40
<212> TYPE: PRT
<213> ORGANISM: Artificial Sequence
<220> FEATURE:
<223> OTHER INFORMATION: Artificially synthesized APS domain

<400> SEQUENCE: 14

Ser Ala Pro Ala Ala Ser Pro Ser Pro Ala Ala Pro Ala Pro Ser Pro
1               5                   10                  15

Ala Ser Pro Ala Pro Ala Ser Pro Ala Ser Ala Pro Ser Ala Pro Ala
                20                  25                  30

Ser Ala Pro Ala Ala Ala Ser Ala
            35                  40

<210> SEQ ID NO 15
<211> LENGTH: 60
<212> TYPE: PRT
<213> ORGANISM: Artificial Sequence
<220> FEATURE:
<223> OTHER INFORMATION: Artificially synthesized APS domain with cys

<400> SEQUENCE: 15

Ser Ala Pro Ala Ala Ser Pro Ser Ala Ala Ala Pro Ala Pro Ser Pro
```

```
1               5                   10                  15
Ala Ser Pro Ala Pro Ala Ser Pro Ala Ser Ala Pro Ser Ala Pro Ala
            20                  25                  30

Ser Ala Pro Pro Ala Ala Ser Cys Ser Ala Pro Ala Ala Ser Pro Ser
        35                  40                  45

Pro Ala Pro Ala Pro Ser Pro Ala Ser Pro Ala
    50                  55                  60
```

<210> SEQ ID NO 16
<211> LENGTH: 40
<212> TYPE: PRT
<213> ORGANISM: Artificial Sequence
<220> FEATURE:
<223> OTHER INFORMATION: Artificially synthesized APS domain with Asp

<400> SEQUENCE: 16

```
Ser Ala Pro Ala Ala Ser Pro Asp Pro Ala Ala Pro Ala Pro Ser Asp
1               5                   10                  15

Ala Ser Pro Ala Pro Ala Ser Asp Ala Ser Ala Pro Ser Ala Pro Asp
            20                  25                  30

Ser Ala Pro Ala Ala Ala Ser Ala
        35                  40
```

<210> SEQ ID NO 17
<211> LENGTH: 60
<212> TYPE: PRT
<213> ORGANISM: Artificial Sequence
<220> FEATURE:
<223> OTHER INFORMATION: Artificially synthesized APS domain with Asp
      and Cys

<400> SEQUENCE: 17

```
Ser Ala Pro Ala Ala Asp Pro Ser Ala Ala Asp Ala Pro Ser Pro
1               5                   10                  15

Ala Asp Pro Ala Pro Ala Ser Asp Ala Ser Ala Pro Ser Asp Pro Ala
            20                  25                  30

Ser Ala Asp Pro Ala Ala Ser Cys Ser Ala Pro Ala Ala Ser Pro Ser
        35                  40                  45

Pro Ala Ala Pro Ala Pro Ser Pro Ala Ser Pro Ala
    50                  55                  60
```

<210> SEQ ID NO 18
<211> LENGTH: 79
<212> TYPE: PRT
<213> ORGANISM: Artificial Sequence
<220> FEATURE:
<223> OTHER INFORMATION: Artificially synthesized APS domain

<400> SEQUENCE: 18

```
Ser Ala Pro Ala Ala Ser Pro Ser Pro Ala Ala Pro Ala Pro Ser Pro
1               5                   10                  15

Ala Ser Pro Ala Pro Ala Ser Pro Ala Ser Ala Pro Ser Ala Pro Ala
            20                  25                  30

Ser Ala Pro Ala Ala Ala Ser Ala Ser Ala Pro Ala Ala Ser Pro Ser
        35                  40                  45

Pro Ala Ala Pro Ala Pro Ser Pro Ala Ser Pro Ala Ser Pro
    50                  55                  60

Ala Ser Ala Pro Ser Ala Pro Ala Ser Ala Pro Ala Ala Ser Ala
65                  70                  75
```

<210> SEQ ID NO 19
<211> LENGTH: 79
<212> TYPE: PRT
<213> ORGANISM: Artificial Sequence
<220> FEATURE:
<223> OTHER INFORMATION: Artificially synthesized APS domain with Cys

<400> SEQUENCE: 19

Ser Ala Pro Ala Ala Ser Pro Ser Ala Ala Pro Ala Pro Ser Pro
1               5                   10                  15

Ala Ser Pro Ala Pro Ala Ser Pro Ala Ser Pro Ala Ser Ala Pro Ala
            20                  25                  30

Ser Ala Pro Pro Ala Ala Ser Pro Ser Ala Pro Ala Ala Ser Pro Ser
        35                  40                  45

Pro Ala Ala Pro Ala Pro Ser Pro Ala Ser Cys Ala Ala Ala Ser Pro
    50                  55                  60

Ser Ala Pro Ala Ala Ser Pro Ser Pro Ala Ala Pro Ala Pro Ser
65                  70                  75

<210> SEQ ID NO 20
<211> LENGTH: 79
<212> TYPE: PRT
<213> ORGANISM: Artificial Sequence
<220> FEATURE:
<223> OTHER INFORMATION: Artificially synthesized APS domain

<400> SEQUENCE: 20

Ser Ala Pro Ala Ala Ser Pro Ser Ala Ala Pro Ala Pro Ser Pro
1               5                   10                  15

Ala Ser Pro Ala Pro Ala Ser Pro Ala Ser Pro Ala Ser Ala Pro Ala
            20                  25                  30

Ser Ala Pro Pro Ala Ala Ser Pro Ser Ala Pro Ala Ala Ser Pro Ser
        35                  40                  45

Pro Ala Ala Pro Ala Pro Ser Pro Ala Ser Pro Ala Ala Ala Ser Pro
    50                  55                  60

Ser Ala Pro Ala Ala Ser Pro Ser Pro Ala Ala Pro Ala Pro Ser
65                  70                  75

<210> SEQ ID NO 21
<211> LENGTH: 213
<212> TYPE: PRT
<213> ORGANISM: Artificial Sequence
<220> FEATURE:
<223> OTHER INFORMATION: Artificially synthesized Fusion protein
      Affilin-138800 / APS domain

<400> SEQUENCE: 21

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
    50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu

```
                   100                 105                 110
Gly Ile Pro Pro Asp Gln Gln Arg Leu Ile Trp Ala Gly Lys Gln Leu
            115                 120                 125

Glu Asp Gly Arg Thr Leu Ser Asp Tyr Asn Ile Asp Tyr Arg Phe Leu
        130                 135                 140

His Leu Val Leu Arg Leu Arg Ala Ala Ser Ala Pro Ala Ala Ser Pro
145                 150                 155                 160

Ser Ala Ala Pro Ala Pro Ser Pro Ala Ser Pro Ala Pro Ala Ser
                165                 170                 175

Pro Ala Ser Ala Pro Ser Ala Pro Ala Ser Ala Pro Ala Ala Ser
            180                 185                 190

Cys Ser Ala Pro Ala Ala Ser Pro Ser Pro Ala Ala Pro Ala Pro Ser
            195                 200                 205

Pro Ala Ser Pro Ala
        210

<210> SEQ ID NO 22
<211> LENGTH: 213
<212> TYPE: PRT
<213> ORGANISM: Artificial Sequence
<220> FEATURE:
<223> OTHER INFORMATION: Artificially synthesized Fusion protein
      Affilin-138800 / APS domain with Asp

<400> SEQUENCE: 22

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
            85                  90                  95

Pro Ser Asp Thr Ile Glu Asn Val Lys Ala Lys Ile Gln Asp Lys Glu
            100                 105                 110

Gly Ile Pro Pro Asp Gln Gln Arg Leu Ile Trp Ala Gly Lys Gln Leu
            115                 120                 125

Glu Asp Gly Arg Thr Leu Ser Asp Tyr Asn Ile Asp Tyr Arg Phe Leu
        130                 135                 140

His Leu Val Leu Arg Leu Arg Ala Ala Ser Ala Pro Ala Ala Asp Pro
145                 150                 155                 160

Ser Ala Ala Asp Ala Pro Ser Pro Ala Asp Pro Ala Pro Ala Ser
                165                 170                 175

Asp Ala Ser Ala Pro Ser Asp Pro Ala Ser Ala Asp Pro Ala Ala Ser
            180                 185                 190

Cys Ser Ala Pro Ala Ala Ser Pro Ser Pro Ala Ala Pro Ala Pro Ser
            195                 200                 205

Pro Ala Ser Pro Ala
        210

<210> SEQ ID NO 23
<211> LENGTH: 406
```

```
<212> TYPE: PRT
<213> ORGANISM: Artificial Sequence
<220> FEATURE:
<223> OTHER INFORMATION: Artificially synthesized Fusion protein
      Affilin-138800 / APS domain / Affilin-138800 / APS domain with Cys

<400> SEQUENCE: 23
```

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
    50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu
            100                 105                 110

Gly Ile Pro Pro Asp Gln Gln Arg Leu Ile Trp Ala Gly Lys Gln Leu
        115                 120                 125

Glu Asp Gly Arg Thr Leu Ser Asp Tyr Asn Ile Asp Tyr Arg Phe Leu
    130                 135                 140

His Leu Val Leu Arg Leu Arg Ala Ala Ser Ala Pro Ala Ala Ser Pro
145                 150                 155                 160

Ser Pro Ala Ala Pro Ala Pro Ser Pro Ala Ser Pro Ala Pro Ala Ser
                165                 170                 175

Pro Ala Ser Ala Pro Ser Ala Pro Ala Ser Ala Pro Ala Ala Ala Ser
            180                 185                 190

Ala Met Gln Ile Phe Val His Thr Asp Thr Gly Lys Thr Ile Thr Leu
        195                 200                 205

Glu Val Glu Pro Ser Asp Thr Ile Glu Asn Val Lys Ala Lys Ile Gln
    210                 215                 220

Asp Lys Glu Gly Ile Pro Gln Asp Gln Gln Arg Leu Ile Trp Ala Gly
225                 230                 235                 240

Lys Gln Leu Glu Asp Gly Arg Thr Leu Ser Asp Tyr Asn Ile Asp Pro
                245                 250                 255

Gln Leu Lys Leu His Leu Val Leu Arg Leu Arg Ala Ala Gly Gly Met
            260                 265                 270

Gln Ile Phe Val Thr Thr Gln Thr Gly Lys Thr Ile Thr Leu Glu Val
        275                 280                 285

Glu Pro Ser Asp Thr Ile Glu Asn Val Lys Ala Lys Ile Gln Asp Lys
    290                 295                 300

Glu Gly Ile Pro Pro Asp Gln Gln Arg Leu Ile Trp Ala Gly Lys Gln
305                 310                 315                 320

Leu Glu Asp Gly Arg Thr Leu Ser Asp Tyr Asn Ile Asp Tyr Arg Phe
                325                 330                 335

Leu His Leu Val Leu Arg Leu Arg Ala Ala Ser Ala Pro Ala Ala Ser
            340                 345                 350

Pro Ser Ala Ala Ala Pro Ala Pro Ser Pro Ala Ser Pro Ala Pro Ala
        355                 360                 365

Ser Pro Ala Ser Ala Pro Ser Ala Pro Ala Ser Ala Pro Pro Ala Ala
    370                 375                 380

```
Ser Cys Ser Ala Pro Ala Ala Ser Pro Ser Pro Ala Ala Pro Ala Pro
385                 390                 395                 400

Ser Pro Ala Ser Pro Ala
                405

<210> SEQ ID NO 24
<211> LENGTH: 406
<212> TYPE: PRT
<213> ORGANISM: Artificial Sequence
<220> FEATURE:
<223> OTHER INFORMATION: Artificially synthesized Fusion protein
      Affilin-138800 / APS domain with Asp / Affilin-138800 / APS domain
      with Asp and Cys

<400> SEQUENCE: 24

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu
            100                 105                 110

Gly Ile Pro Pro Asp Gln Gln Arg Leu Ile Trp Ala Gly Lys Gln Leu
        115                 120                 125

Glu Asp Gly Arg Thr Leu Ser Asp Tyr Asn Ile Asp Tyr Arg Phe Leu
130                 135                 140

His Leu Val Leu Arg Leu Arg Ala Ala Ser Ala Pro Ala Ala Ser Pro
145                 150                 155                 160

Asp Pro Ala Ala Pro Ala Pro Ser Asp Ala Ser Pro Ala Pro Ala Ser
                165                 170                 175

Asp Ala Ser Ala Pro Ser Ala Pro Asp Ser Ala Pro Ala Ala Ala Ser
            180                 185                 190

Ala Met Gln Ile Phe Val His Thr Asp Thr Gly Lys Thr Ile Thr Leu
        195                 200                 205

Glu Val Glu Pro Ser Asp Thr Ile Glu Asn Val Lys Ala Lys Ile Gln
210                 215                 220

Asp Lys Glu Gly Ile Pro Gln Asp Gln Gln Arg Leu Ile Trp Ala Gly
225                 230                 235                 240

Lys Gln Leu Glu Asp Gly Arg Thr Leu Ser Asp Tyr Asn Ile Asp Pro
                245                 250                 255

Gln Leu Lys Leu His Leu Val Leu Arg Leu Arg Ala Ala Gly Gly Met
            260                 265                 270

Gln Ile Phe Val Thr Thr Gln Thr Gly Lys Thr Ile Thr Leu Glu Val
        275                 280                 285

Glu Pro Ser Asp Thr Ile Glu Asn Val Lys Ala Lys Ile Gln Asp Lys
290                 295                 300

Glu Gly Ile Pro Pro Asp Gln Gln Arg Leu Ile Trp Ala Gly Lys Gln
305                 310                 315                 320
```

```
Leu Glu Asp Gly Arg Thr Leu Ser Asp Tyr Asn Ile Asp Tyr Arg Phe
            325                 330                 335

Leu His Leu Val Leu Arg Leu Arg Ala Ala Ser Ala Pro Ala Ala Asp
            340                 345                 350

Pro Ser Ala Ala Ala Asp Ala Pro Ser Pro Ala Asp Pro Ala Pro Ala
            355                 360                 365

Ser Asp Ala Ser Ala Pro Ser Asp Pro Ala Ser Ala Asp Pro Ala Ala
            370                 375                 380

Ser Cys Ser Ala Pro Ala Ala Ser Pro Ser Pro Ala Ala Pro Ala Pro
385                 390                 395                 400

Ser Pro Ala Ser Pro Ala
            405

<210> SEQ ID NO 25
<211> LENGTH: 464
<212> TYPE: PRT
<213> ORGANISM: Artificial Sequence
<220> FEATURE:
<223> OTHER INFORMATION: Artificially synthesized Fusion protein
      Affilin-138800 / APS domain  / Affilin-138800 / APS domain with
      Cys

<400> SEQUENCE: 25

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Asp Pro Gln
50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu
            100                 105                 110

Gly Ile Pro Pro Asp Gln Gln Arg Leu Ile Trp Ala Gly Lys Gln Leu
        115                 120                 125

Glu Asp Gly Arg Thr Leu Ser Asp Tyr Asn Ile Asp Tyr Arg Phe Leu
130                 135                 140

His Leu Val Leu Arg Leu Arg Ala Ala Ser Ala Pro Ala Ala Ser Pro
145                 150                 155                 160

Ser Pro Ala Ala Pro Ala Pro Ser Pro Ala Ser Pro Ala Pro Ala Ser
            165                 170                 175

Pro Ala Ser Ala Pro Ser Ala Pro Ser Pro Ala Ala Ala Ala Ala Ser
            180                 185                 190

Ala Ser Ala Pro Ala Ala Ser Pro Ser Pro Ala Ala Pro Ala Pro Ser
        195                 200                 205

Pro Ala Ser Pro Ala Pro Ala Ser Pro Ala Ser Ala Pro Ser Ala Pro
    210                 215                 220

Ala Ser Ala Pro Ala Ala Ser Ala Met Gln Ile Phe Val His Thr Asp
225                 230                 235                 240

Thr Gly Lys Thr Ile Thr Leu Glu Val Glu Pro Ser Asp Thr Ile Glu
                245                 250                 255

Asn Val Lys Ala Lys Ile Gln Asp Lys Glu Gly Ile Pro Gln Asp Gln
```

```
            260                 265                 270
Gln Arg Leu Ile Trp Ala Gly Lys Gln Leu Glu Asp Gly Arg Thr Leu
        275                 280                 285

Ser Asp Tyr Asn Ile Asp Pro Gln Leu Lys Leu His Leu Val Leu Arg
        290                 295                 300

Leu Arg Ala Ala Gly Gly Met Gln Ile Phe Val Thr Gln Thr Gly
305                 310                 315                 320

Lys Thr Ile Thr Leu Glu Val Glu Pro Ser Asp Thr Ile Glu Asn Val
                325                 330                 335

Lys Ala Lys Ile Gln Asp Lys Glu Gly Ile Pro Pro Asp Gln Gln Arg
                340                 345                 350

Leu Ile Trp Ala Gly Lys Gln Leu Glu Asp Gly Arg Thr Leu Ser Asp
        355                 360                 365

Tyr Asn Ile Asp Tyr Arg Phe Leu His Leu Val Leu Arg Leu Arg Ala
        370                 375                 380

Ala Ser Ala Pro Ala Ala Ser Pro Ser Ala Ala Pro Ala Pro Ser
385                 390                 395                 400

Pro Ala Ser Pro Ala Pro Ala Ser Pro Ala Ser Ala Pro Ser Ala Pro
                405                 410                 415

Ala Ser Ala Pro Pro Ala Ala Ser Pro Ser Ala Pro Ala Ala Ser Pro
                420                 425                 430

Ser Pro Ala Ala Pro Ala Pro Ser Pro Ala Ser Pro Ala Ala Ala Ser
        435                 440                 445

Pro Ser Ala Pro Ala Ala Ser Pro Ser Pro Ala Ala Pro Ala Pro Ser
450                 455                 460
```

<210> SEQ ID NO 26
<211> LENGTH: 215
<212> TYPE: PRT
<213> ORGANISM: Artificial Sequence
<220> FEATURE:
<223> OTHER INFORMATION: Artificially synthesized Fusion protein
    Affilin-77404 / APS domain with Cys

<400> SEQUENCE: 26

```
Met Arg Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Asn Pro Lys
50                  55                  60

Leu Ser Leu His Leu Val Leu Arg Leu Arg Ala Ala Gly Ile Gly Met
65                  70                  75                  80

Gln Ile Phe Val His Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Gly Trp Gln Ala
        130                 135                 140

Pro Leu His Leu Val Leu Arg Leu Arg Ala Ala Ser Ala Pro Ala Ala
145                 150                 155                 160
```

Ser Pro Ser Ala Ala Pro Ala Pro Ser Pro Ala Ser Pro Ala Pro
                165                 170                 175

Ala Ser Pro Ala Ser Ala Pro Ser Ala Pro Ala Ser Ala Pro Pro Ala
            180                 185                 190

Ala Ser Cys Ser Ala Pro Ala Ala Ser Pro Ser Pro Ala Ala Pro Ala
            195                 200                 205

Pro Ser Pro Ala Ser Pro Ala
        210                 215

<210> SEQ ID NO 27
<211> LENGTH: 215
<212> TYPE: PRT
<213> ORGANISM: Artificial Sequence
<220> FEATURE:
<223> OTHER INFORMATION: Artificially synthesized Fusion protein
      Affilin-77404 / APS domain with Asp and Cys

<400> SEQUENCE: 27

Met Arg Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Pro Lys
50                  55                  60

Leu Ser Leu His Leu Val Leu Arg Leu Arg Ala Ala Gly Ile Gly Met
65                  70                  75                  80

Gln Ile Phe Val His Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Trp Gln Ala
130                 135                 140

Pro Leu His Leu Val Leu Arg Leu Arg Ala Ala Ser Ala Pro Ala Ala
145                 150                 155                 160

Asp Pro Ser Ala Ala Asp Ala Pro Ser Pro Ala Asp Pro Ala Pro
                165                 170                 175

Ala Ser Asp Ala Ser Ala Pro Ser Asp Pro Ala Ser Ala Asp Pro Ala
            180                 185                 190

Ala Ser Cys Ser Ala Pro Ala Ala Ser Pro Ser Pro Ala Ala Pro Ala
            195                 200                 205

Pro Ser Pro Ala Ser Pro Ala
        210                 215

<210> SEQ ID NO 28
<211> LENGTH: 410
<212> TYPE: PRT
<213> ORGANISM: Artificial Sequence
<220> FEATURE:
<223> OTHER INFORMATION: Artificially synthesized Fusion protein
      Affilin-77404 / APS domain / Affilin-77404 / APS domain with Cys

<400> SEQUENCE: 28

Met Arg Ile Trp Val His Thr Leu Thr Gly Lys Thr Ile Thr Leu Glu
1               5                   10                  15

-continued

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Pro Lys
    50                  55                  60

Leu Ser Leu His Leu Val Leu Arg Leu Arg Ala Ala Gly Ile Gly Met
65                  70                  75                  80

Gln Ile Phe Val His Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Trp Gln Ala
    130                 135                 140

Pro Leu His Leu Val Leu Arg Leu Arg Ala Ala Ser Ala Pro Ala Ala
145                 150                 155                 160

Ser Pro Ser Pro Ala Ala Pro Ala Pro Ser Pro Ala Ser Pro Ala Pro
                165                 170                 175

Ala Ser Pro Ala Ser Ala Pro Ser Ala Pro Ser Ala Pro Ala Ala
                180                 185                 190

Ala Ser Ala Met Arg Ile Trp Val His Thr Leu Thr Gly Lys Thr Ile
            195                 200                 205

Thr Leu Glu Val Glu Pro Ser Asp Thr Ile Glu Asn Val Lys Ala Lys
210                 215                 220

Ile Gln Asp Lys Glu Gly Ile Pro Pro Asp Gln Gln Arg Leu Ile Trp
225                 230                 235                 240

Ala Gly Lys Gln Leu Glu Asp Gly Arg Thr Leu Ser Asp Tyr Asn Ile
            245                 250                 255

Asn Pro Lys Leu Ser Leu His Leu Val Leu Arg Leu Arg Ala Ala Gly
        260                 265                 270

Ile Gly Met Gln Ile Phe Val His Thr Gln Thr Gly Lys Thr Ile Thr
    275                 280                 285

Leu Glu Val Glu Pro Ser Asp Thr Ile Glu Asn Val Lys Ala Lys Ile
290                 295                 300

Gln Asp Lys Glu Gly Ile Pro Pro Asp Gln Gln Arg Leu Ile Trp Ala
305                 310                 315                 320

Gly Lys Gln Leu Glu Asp Gly Arg Thr Leu Ser Asp Tyr Asn Ile Gly
            325                 330                 335

Trp Gln Ala Pro Leu His Leu Val Leu Arg Leu Arg Ala Ala Ser Ala
        340                 345                 350

Pro Ala Ala Ser Pro Ser Ala Ala Pro Ala Pro Ser Pro Ala Ser
    355                 360                 365

Pro Ala Pro Ala Ser Pro Ala Ser Ala Pro Ser Ala Pro Ala Ser Ala
    370                 375                 380

Pro Pro Ala Ala Ser Cys Ser Ala Pro Ala Ala Ser Pro Ser Pro Ala
385                 390                 395                 400

Ala Pro Ala Pro Ser Pro Ala Ser Pro Ala
            405                 410

<210> SEQ ID NO 29
<211> LENGTH: 410
<212> TYPE: PRT

<213> ORGANISM: Artificial Sequence
<220> FEATURE:
<223> OTHER INFORMATION: Artificially synthesized Fusion protein
    Affilin-77404 / APS domain with Asp / Affilin-77404 / APS domain
    with Asp and Cys

<400> SEQUENCE: 29

```
Met Arg Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Pro Lys
    50                  55                  60

Leu Ser Leu His Leu Val Leu Arg Leu Arg Ala Ala Gly Ile Gly Met
65                  70                  75                  80

Gln Ile Phe Val His Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Trp Gln Ala
    130                 135                 140

Pro Leu His Leu Val Leu Arg Leu Arg Ala Ala Ser Ala Pro Ala Ala
145                 150                 155                 160

Ser Pro Asp Pro Ala Ala Pro Ala Pro Ser Asp Ala Ser Pro Ala Pro
                165                 170                 175

Ala Ser Asp Ala Ser Ala Pro Ser Ala Pro Asp Ser Ala Pro Ala Ala
            180                 185                 190

Ala Ser Ala Met Arg Ile Trp Val His Thr Leu Thr Gly Lys Thr Ile
        195                 200                 205

Thr Leu Glu Val Glu Pro Ser Asp Thr Ile Glu Asn Val Lys Ala Lys
    210                 215                 220

Ile Gln Asp Lys Glu Gly Ile Pro Pro Asp Gln Gln Arg Leu Ile Trp
225                 230                 235                 240

Ala Gly Lys Gln Leu Glu Asp Gly Arg Thr Leu Ser Asp Tyr Asn Ile
                245                 250                 255

Asn Pro Lys Leu Ser Leu His Leu Val Leu Arg Leu Arg Ala Ala Gly
            260                 265                 270

Ile Gly Met Gln Ile Phe Val His Thr Gln Thr Gly Lys Thr Ile Thr
        275                 280                 285

Leu Glu Val Glu Pro Ser Asp Thr Ile Glu Asn Val Lys Ala Lys Ile
    290                 295                 300

Gln Asp Lys Glu Gly Ile Pro Pro Asp Gln Gln Arg Leu Ile Trp Ala
305                 310                 315                 320

Gly Lys Gln Leu Glu Asp Gly Arg Thr Leu Ser Asp Tyr Asn Ile Gly
                325                 330                 335

Trp Gln Ala Pro Leu His Leu Val Leu Arg Leu Arg Ala Ala Ser Ala
            340                 345                 350

Pro Ala Ala Asp Pro Ser Ala Ala Asp Ala Pro Ser Pro Ala Asp
        355                 360                 365

Pro Ala Pro Ala Ser Asp Ala Ser Ala Pro Ser Asp Pro Ala Ser Ala
    370                 375                 380
```

Asp Pro Ala Ala Ser Cys Ser Ala Pro Ala Ser Pro Ser Pro Ala
385                 390                 395                 400

Ala Pro Ala Pro Ser Pro Ala Ser Pro Ala
                405                 410

<210> SEQ ID NO 30
<211> LENGTH: 468
<212> TYPE: PRT
<213> ORGANISM: Artificial Sequence
<220> FEATURE:
<223> OTHER INFORMATION: Artificially synthesized Fusion protein
      Affilin-77404 / APS domain with Asp / Affilin-77404 / APS domain
      with Asp and Cys

<400> SEQUENCE: 30

Met Arg Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Pro Lys
50                  55                  60

Leu Ser Leu His Leu Val Leu Arg Leu Arg Ala Ala Gly Ile Gly Met
65                  70                  75                  80

Gln Ile Phe Val His Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Trp Gln Ala
    130                 135                 140

Pro Leu His Leu Val Leu Arg Leu Arg Ala Ala Ser Ala Pro Ala Ala
145                 150                 155                 160

Ser Pro Ser Pro Ala Ala Pro Ala Pro Ser Pro Ala Ser Pro Ala Pro
                165                 170                 175

Ala Ser Pro Ala Ser Ala Pro Ser Ala Pro Ala Ser Pro Ala Ala
            180                 185                 190

Ala Ser Ala Ser Ala Pro Ala Ala Ser Pro Ser Pro Ala Ala Pro Ala
    195                 200                 205

Pro Ser Pro Ala Ser Pro Ala Pro Ala Ser Pro Ala Ser Ala Pro Ser
210                 215                 220

Ala Pro Ala Ser Ala Pro Ala Ala Ser Ala Met Arg Ile Trp Val His
225                 230                 235                 240

Thr Leu Thr Gly Lys Thr Ile Thr Leu Glu Val Glu Pro Ser Asp Thr
                245                 250                 255

Ile Glu Asn Val Lys Ala Lys Ile Gln Asp Lys Glu Gly Ile Pro Pro
            260                 265                 270

Asp Gln Gln Arg Leu Ile Trp Ala Gly Lys Gln Leu Glu Asp Gly Arg
        275                 280                 285

Thr Leu Ser Asp Tyr Asn Ile Asn Pro Lys Leu Ser Leu His Leu Val
    290                 295                 300

Leu Arg Leu Arg Ala Ala Gly Ile Gly Met Gln Ile Phe Val His Thr
305                 310                 315                 320

-continued

```
Gln Thr Gly Lys Thr Ile Thr Leu Glu Val Glu Pro Ser Asp Thr Ile
                325                 330                 335

Glu Asn Val Lys Ala Lys Ile Gln Asp Lys Glu Gly Ile Pro Pro Asp
            340                 345                 350

Gln Gln Arg Leu Ile Trp Ala Gly Lys Gln Leu Glu Asp Gly Arg Thr
        355                 360                 365

Leu Ser Asp Tyr Asn Ile Gly Trp Gln Ala Pro Leu His Leu Val Leu
    370                 375                 380

Arg Leu Arg Ala Ala Ser Ala Pro Ala Ala Ser Pro Ser Ala Ala Ala
385                 390                 395                 400

Pro Ala Pro Ser Pro Ala Ser Pro Ala Pro Ala Ser Pro Ala Ser Ala
                405                 410                 415

Pro Ser Ala Pro Ala Ser Ala Pro Pro Ala Ala Ser Pro Ser Ala Pro
                420                 425                 430

Ala Ala Ser Pro Ser Pro Ala Ala Pro Ala Pro Ser Pro Ala Ser Pro
            435                 440                 445

Ala Ala Ala Ser Pro Ser Ala Pro Ala Ala Ser Pro Ser Pro Ala Ala
        450                 455                 460

Pro Ala Pro Ser
465

<210> SEQ ID NO 31
<211> LENGTH: 155
<212> TYPE: PRT
<213> ORGANISM: Artificial Sequence
<220> FEATURE:
<223> OTHER INFORMATION: Artificially synthesized bis-ubiquitin
      (CID64156)

<400> SEQUENCE: 31

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala Gly Ile Gly Met
65                  70                  75                  80

Gln Ile Phe Val Lys Thr Leu Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gln Lys Glu Ser
    130                 135                 140

Thr Leu His Leu Val Leu Arg Leu Arg Ala Ala
145                 150                 155

<210> SEQ ID NO 32
<211> LENGTH: 155
<212> TYPE: PRT
<213> ORGANISM: Artificial Sequence
<220> FEATURE:
<223> OTHER INFORMATION: Artificially synthesized bis-ubiquitin,
      wildtype
```

<400> SEQUENCE: 32

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ile Gly Met
65                  70                  75                  80

Gln Ile Phe Val Lys Thr Leu Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Phe Ala Gly Lys Gln
            115                 120                 125

Leu Glu Asp Gly Arg Thr Leu Ser Asp Tyr Asn Ile Gln Lys Glu Ser
        130                 135                 140

Thr Leu His Leu Val Leu Arg Leu Arg Gly Gly
145                 150                 155
```

<210> SEQ ID NO 33
<211> LENGTH: 155
<212> TYPE: PRT
<213> ORGANISM: Artificial Sequence
<220> FEATURE:
<223> OTHER INFORMATION: Artificially synthesized Affilin-1041D11

<400> SEQUENCE: 33

```
Met Gln Ile Phe Val Trp Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Arg Lys
    50                  55                  60

Phe Pro Leu His Leu Val Leu Arg Leu Arg Ala Ala Gly Ile Gly Met
65                  70                  75                  80

Arg Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Trp Ser Asn Trp
        130                 135                 140

Glu Leu His Leu Val Leu Arg Leu Arg Ala Ala
145                 150                 155
```

<210> SEQ ID NO 34
<211> LENGTH: 155
<212> TYPE: PRT
<213> ORGANISM: Artificial Sequence
<220> FEATURE:

<223> OTHER INFORMATION: Artificially synthesized Affilin-77404 with
     S57C

<400> SEQUENCE: 34

Met Arg Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Cys Asp Tyr Asn Ile Asn Pro Lys
50                  55                  60

Leu Ser Leu His Leu Val Leu Arg Leu Arg Ala Ala Gly Ile Gly Met
65                  70                  75                  80

Gln Ile Phe Val His Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Trp Gln Ala
    130                 135                 140

Pro Leu His Leu Val Leu Arg Leu Arg Ala Ala
145                 150                 155

<210> SEQ ID NO 35
<211> LENGTH: 153
<212> TYPE: PRT
<213> ORGANISM: Artificial Sequence
<220> FEATURE:
<223> OTHER INFORMATION: Artificially synthesized Affilin-138800 with
     S57C

<400> SEQUENCE: 35

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Cys Asp Tyr Asn Ile Asp Pro Gln
50                  55                  60

Leu Lys Leu His Leu Val Leu Arg Leu Arg Ala Ala Gly Gly Met Gln
65                  70                  75                  80

Ile Phe Val Thr Thr Gln Thr Gly Lys Thr Ile Thr Leu Glu Val Glu
                85                  90                  95

Pro Ser Asp Thr Ile Glu Asn Val Lys Ala Lys Ile Gln Asp Lys Glu
            100                 105                 110

Gly Ile Pro Pro Asp Gln Gln Arg Leu Ile Trp Ala Gly Lys Gln Leu
        115                 120                 125

Glu Asp Gly Arg Thr Leu Ser Asp Tyr Asn Ile Asp Tyr Arg Phe Leu
    130                 135                 140

His Leu Val Leu Arg Leu Arg Ala Ala
145                 150

<210> SEQ ID NO 36
<211> LENGTH: 151

```
<212> TYPE: PRT
<213> ORGANISM: Artificial Sequence
<220> FEATURE:
<223> OTHER INFORMATION: Artificially synthesized Affilin-181494 with
      S57C (corresponding to pos 57 of SEQ ID NO 32)

<400> SEQUENCE: 36

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Cys Asp Tyr Asn Ile Gln Lys Lys
    50                  55                  60

Ser His Leu Val Leu Arg Leu Arg Ala Ala Gly Gly Met Gln Ile Phe
65                  70                  75                  80

Val Thr Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Asp Tyr Arg Phe Leu His Leu
    130                 135                 140

Val Leu Arg Leu Arg Ala Ala
145                 150

<210> SEQ ID NO 37
<211> LENGTH: 76
<212> TYPE: PRT
<213> ORGANISM: Artificial Sequence
<220> FEATURE:
<223> OTHER INFORMATION: Artificially synthesized ubiquitin (monomer
      based on 64156)

<400> SEQUENCE: 37

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala
65                  70                  75

<210> SEQ ID NO 38
<211> LENGTH: 76
<212> TYPE: PRT
<213> ORGANISM: Artificial Sequence
<220> FEATURE:
<223> OTHER INFORMATION: Artificially synthesized ubiquitin wildtype

<400> SEQUENCE: 38

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30
```

```
Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
 50                  55                  60

Ser Thr Leu His Leu Val Leu Arg Leu Arg Gly Gly
 65                  70                  75
```

<210> SEQ ID NO 39
<211> LENGTH: 211
<212> TYPE: PRT
<213> ORGANISM: Artificial Sequence
<220> FEATURE:
<223> OTHER INFORMATION: Artificially synthesized Fusion protein
      Affilin--181494 / APS domain

<400> SEQUENCE: 39

```
Met Gln Ile Phe Val His Thr Asp Thr Gly Lys Thr Ile Thr Leu Glu
 1               5                  10                  15

Val Glu Pro Ser Asp Thr Ile Glu Asn Val Lys Ala Lys Ile Gln Asp
             20                  25                  30

Lys Glu Gly Ile Pro Gln Asp Gln Gln Arg Leu Ile Trp Ala Gly Lys
         35                  40                  45

Gln Leu Glu Asp Gly Arg Thr Leu Ser Asp Tyr Asn Ile Gln Lys Lys
 50                  55                  60

Ser His Leu Val Leu Arg Leu Arg Ala Ala Gly Met Gln Ile Phe
 65                  70                  75                  80

Val Thr Thr Gln Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Asp Tyr Arg Phe Leu His Leu
        130                 135                 140

Val Leu Arg Leu Arg Ala Ala Ser Ala Pro Ala Ala Ser Pro Ser Ala
145                 150                 155                 160

Ala Ala Pro Ala Pro Ser Pro Ala Ser Pro Ala Pro Ala Ser Pro Ala
                165                 170                 175

Ser Ala Pro Ser Ala Pro Ala Ser Ala Pro Ala Ala Ser Cys Ser
                180                 185                 190

Ala Pro Ala Ala Ser Pro Ser Pro Ala Ala Pro Ala Pro Ser Pro Ala
                195                 200                 205

Ser Pro Ala
    210
```

<210> SEQ ID NO 40
<211> LENGTH: 211
<212> TYPE: PRT
<213> ORGANISM: Artificial Sequence
<220> FEATURE:
<223> OTHER INFORMATION: Artificially synthesized Fusion protein
      Affilin-181494 / APS domain with Asp

<400> SEQUENCE: 40

```
Met Gln Ile Phe Val His Thr Asp Thr Gly Lys Thr Ile Thr Leu Glu
 1               5                  10                  15

Val Glu Pro Ser Asp Thr Ile Glu Asn Val Lys Ala Lys Ile Gln Asp
             20                  25                  30
```

Lys Glu Gly Ile Pro Gln Asp Gln Gln Arg Leu Ile Trp Ala Gly Lys
            35                  40                  45

Gln Leu Glu Asp Gly Arg Thr Leu Ser Asp Tyr Asn Ile Gln Lys Lys
 50                  55                  60

Ser His Leu Val Leu Arg Leu Arg Ala Ala Gly Gly Met Gln Ile Phe
 65                  70                  75                  80

Val Thr Thr Gln Thr Gly Lys Thr Ile Thr Leu Glu Val Glu Pro Ser
                    85                  90                  95

Asp Thr Ile Glu Asn Val Lys Ala Lys Ile Gln Asp Lys Glu Gly Ile
                    100                 105                 110

Pro Pro Asp Gln Gln Arg Leu Ile Trp Ala Gly Lys Gln Leu Glu Asp
                    115                 120                 125

Gly Arg Thr Leu Ser Asp Tyr Asn Ile Asp Tyr Arg Phe Leu His Leu
            130                 135                 140

Val Leu Arg Leu Arg Ala Ala Ser Ala Pro Ala Ala Asp Pro Ser Ala
145                 150                 155                 160

Ala Ala Asp Ala Pro Ser Pro Ala Asp Pro Ala Pro Ala Ser Asp Ala
                    165                 170                 175

Ser Ala Pro Ser Asp Pro Ala Ser Ala Asp Pro Ala Ala Ser Cys Ser
                    180                 185                 190

Ala Pro Ala Ala Ser Pro Ser Pro Ala Ala Pro Ala Pro Ser Pro Ala
                    195                 200                 205

Ser Pro Ala
    210

<210> SEQ ID NO 41
<211> LENGTH: 402
<212> TYPE: PRT
<213> ORGANISM: Artificial Sequence
<220> FEATURE:
<223> OTHER INFORMATION: Artificially synthesized Fusion protein
      Affilin-181494 / APS domain / Affilin--181494/ APS domain with Cys

<400> SEQUENCE: 41

Met Gln Ile Phe Val His Thr Asp Thr Gly Lys Thr Ile Thr Leu Glu
 1                5                  10                  15

Val Glu Pro Ser Asp Thr Ile Glu Asn Val Lys Ala Lys Ile Gln Asp
                20                  25                  30

Lys Glu Gly Ile Pro Gln Asp Gln Gln Arg Leu Ile Trp Ala Gly Lys
            35                  40                  45

Gln Leu Glu Asp Gly Arg Thr Leu Ser Asp Tyr Asn Ile Gln Lys Lys
 50                  55                  60

Ser His Leu Val Leu Arg Leu Arg Ala Ala Gly Gly Met Gln Ile Phe
 65                  70                  75                  80

Val Thr Thr Gln Thr Gly Lys Thr Ile Thr Leu Glu Val Glu Pro Ser
                    85                  90                  95

Asp Thr Ile Glu Asn Val Lys Ala Lys Ile Gln Asp Lys Glu Gly Ile
                    100                 105                 110

Pro Pro Asp Gln Gln Arg Leu Ile Trp Ala Gly Lys Gln Leu Glu Asp
                    115                 120                 125

Gly Arg Thr Leu Ser Asp Tyr Asn Ile Asp Tyr Arg Phe Leu His Leu
            130                 135                 140

Val Leu Arg Leu Arg Ala Ala Ser Ala Pro Ala Ala Ser Pro Ser Pro
145                 150                 155                 160

Ala Ala Pro Ala Pro Ser Pro Ala Ser Pro Ala Pro Ala Ser Pro Ala 165                 170                 175
Ser Ala Pro Ser Ala Pro Ala Ser Ala Pro Ala Ala Ser Ala Met
            180                 185                 190

Gln Ile Phe Val His Thr Asp Thr Gly Lys Thr Ile Thr Leu Glu Val
            195                 200                 205

Glu Pro Ser Asp Thr Ile Glu Asn Val Lys Ala Lys Ile Gln Asp Lys
            210                 215                 220

Glu Gly Ile Pro Gln Asp Gln Gln Arg Leu Ile Trp Ala Gly Lys Gln
225                 230                 235                 240

Leu Glu Asp Gly Arg Thr Leu Ser Asp Tyr Asn Ile Gln Lys Lys Ser
                245                 250                 255

His Leu Val Leu Arg Leu Arg Ala Ala Gly Gly Met Gln Ile Phe Val
                260                 265                 270

Thr Thr Gln Thr Gly Lys Thr Ile Thr Leu Glu Val Glu Pro Ser Asp
            275                 280                 285

Thr Ile Glu Asn Val Lys Ala Lys Ile Gln Asp Lys Glu Gly Ile Pro
            290                 295                 300

Pro Asp Gln Gln Arg Leu Ile Trp Ala Gly Lys Gln Leu Glu Asp Gly
305                 310                 315                 320

Arg Thr Leu Ser Asp Tyr Asn Ile Asp Tyr Arg Phe Leu His Leu Val
                325                 330                 335

Leu Arg Leu Arg Ala Ala Ser Ala Pro Ala Ala Ser Pro Ser Ala Ala
                340                 345                 350

Ala Pro Ala Pro Ser Pro Ala Ser Pro Ala Pro Ala Ser Pro Ala Ser
            355                 360                 365

Ala Pro Ser Ala Pro Ala Ser Ala Pro Pro Ala Ala Ser Cys Ser Ala
            370                 375                 380

Pro Ala Ala Ser Pro Ser Pro Ala Ala Pro Ala Pro Ser Pro Ala Ser
385                 390                 395                 400

Pro Ala

<210> SEQ ID NO 42
<211> LENGTH: 402
<212> TYPE: PRT
<213> ORGANISM: Artificial Sequence
<220> FEATURE:
<223> OTHER INFORMATION: Artificially synthesized Fusion protein
      Affilin--181494 / APS domain with Asp / Affilin--181494 / APS
      domain with Asp and Cys

<400> SEQUENCE: 42

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Gln Lys Lys
    50                  55                  60

Ser His Leu Val Leu Arg Leu Arg Ala Ala Gly Gly Met Gln Ile Phe
65                  70                  75                  80

Val Thr Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Asp Tyr Arg Phe Leu His Leu
        130                 135                 140

Val Leu Arg Leu Arg Ala Ala Ser Ala Pro Ala Ala Ser Pro Asp Pro
145                 150                 155                 160

Ala Ala Pro Ala Pro Ser Asp Ala Ser Pro Ala Pro Ala Ser Asp Ala
                165                 170                 175

Ser Ala Pro Ser Ala Pro Asp Ser Ala Pro Ala Ala Ser Ala Met
                180                 185                 190

Gln Ile Phe Val His Thr Asp Thr Gly Lys Thr Ile Thr Leu Glu Val
            195                 200                 205

Glu Pro Ser Asp Thr Ile Glu Asn Val Lys Ala Lys Ile Gln Asp Lys
210                 215                 220

Glu Gly Ile Pro Gln Asp Gln Gln Arg Leu Ile Trp Ala Gly Lys Gln
225                 230                 235                 240

Leu Glu Asp Gly Arg Thr Leu Ser Asp Tyr Asn Ile Gln Lys Lys Ser
                245                 250                 255

His Leu Val Leu Arg Leu Arg Ala Ala Gly Gly Met Gln Ile Phe Val
            260                 265                 270

Thr Thr Gln Thr Gly Lys Thr Ile Thr Leu Glu Val Glu Pro Ser Asp
        275                 280                 285

Thr Ile Glu Asn Val Lys Ala Lys Ile Gln Asp Lys Glu Gly Ile Pro
    290                 295                 300

Pro Asp Gln Gln Arg Leu Ile Trp Ala Gly Lys Gln Leu Glu Asp Gly
305                 310                 315                 320

Arg Thr Leu Ser Asp Tyr Asn Ile Asp Tyr Arg Phe Leu His Leu Val
                325                 330                 335

Leu Arg Leu Arg Ala Ala Ser Ala Pro Ala Ala Asp Pro Ser Ala Ala
            340                 345                 350

Ala Asp Ala Pro Ser Pro Ala Asp Pro Ala Pro Ala Ser Asp Ala Ser
        355                 360                 365

Ala Pro Ser Asp Pro Ala Ser Ala Asp Pro Ala Ala Ser Cys Ser Ala
    370                 375                 380

Pro Ala Ala Ser Pro Ser Pro Ala Ala Pro Ala Pro Ser Pro Ala Ser
385                 390                 395                 400

Pro Ala

<210> SEQ ID NO 43
<211> LENGTH: 460
<212> TYPE: PRT
<213> ORGANISM: Artificial Sequence
<220> FEATURE:
<223> OTHER INFORMATION: Artificially synthesized Fusion protein
      Affilin--181494/ APS domain  / Affilin-181494 / APS domain with Cy

<400> SEQUENCE: 43

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Gln Asp Gln Gln Arg Leu Ile Trp Ala Gly Lys
        35                  40                  45

Gln Leu Glu Asp Gly Arg Thr Leu Ser Asp Tyr Asn Ile Gln Lys Lys
    50                  55                  60

```
Ser His Leu Val Leu Arg Leu Arg Ala Ala Gly Met Gln Ile Phe
 65                  70                  75                  80

Val Thr Thr Gln Thr Gly Lys Thr Ile Thr Leu Glu Val Glu Pro Ser
             85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Asp Tyr Arg Phe Leu His Leu
    130                 135                 140

Val Leu Arg Leu Arg Ala Ala Ser Ala Pro Ala Ala Ser Pro Ser Pro
145                 150                 155                 160

Ala Ala Pro Ala Pro Ser Pro Ala Ser Pro Ala Pro Ala Ser Pro Ala
                165                 170                 175

Ser Ala Pro Ser Ala Pro Ala Ser Ala Pro Ala Ala Ala Ser Ala Ser
                180                 185                 190

Ala Pro Ala Ala Ser Pro Ser Pro Ala Ala Pro Ala Pro Ser Pro Ala
            195                 200                 205

Ser Pro Ala Pro Ala Ser Pro Ala Ser Ala Pro Ser Ala Pro Ala Ser
    210                 215                 220

Ala Pro Ala Ala Ser Ala Met Gln Ile Phe Val His Thr Asp Thr Gly
225                 230                 235                 240

Lys Thr Ile Thr Leu Glu Val Glu Pro Ser Asp Thr Ile Glu Asn Val
                245                 250                 255

Lys Ala Lys Ile Gln Asp Lys Glu Gly Ile Pro Gln Asp Gln Gln Arg
            260                 265                 270

Leu Ile Trp Ala Gly Lys Gln Leu Glu Asp Gly Arg Thr Leu Ser Asp
        275                 280                 285

Tyr Asn Ile Gln Lys Lys Ser His Leu Val Leu Arg Leu Arg Ala Ala
    290                 295                 300

Gly Gly Met Gln Ile Phe Val Thr Thr Gln Thr Gly Lys Thr Ile Thr
305                 310                 315                 320

Leu Glu Val Glu Pro Ser Asp Thr Ile Glu Asn Val Lys Ala Lys Ile
                325                 330                 335

Gln Asp Lys Glu Gly Ile Pro Pro Asp Gln Gln Arg Leu Ile Trp Ala
            340                 345                 350

Gly Lys Gln Leu Glu Asp Gly Arg Thr Leu Ser Asp Tyr Asn Ile Asp
        355                 360                 365

Tyr Arg Phe Leu His Leu Val Leu Arg Leu Arg Ala Ala Ser Ala Pro
    370                 375                 380

Ala Ala Ser Pro Ser Ala Ala Pro Ala Pro Ser Pro Ala Ser Pro Ala
385                 390                 395                 400

Ala Pro Ala Ser Pro Ala Ser Ala Pro Ser Ala Pro Ala Ser Ala Pro
                405                 410                 415

Pro Ala Ala Ser Pro Ser Ala Pro Ala Ala Ser Pro Ser Ala Pro Ala
            420                 425                 430

Pro Ala Pro Ser Pro Ala Ser Pro Ala Ala Ala Ser Pro Ser Ala Pro
        435                 440                 445

Ala Ala Ser Pro Ser Pro Ala Pro Ala Pro Ser
    450                 455                 460

<210> SEQ ID NO 44
<211> LENGTH: 252
<212> TYPE: PRT
```

<213> ORGANISM: Artificial Sequence
<220> FEATURE:
<223> OTHER INFORMATION: Artificially synthesized CID 180339
      (UBI-40-Ubi-60)

<400> SEQUENCE: 44

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala Ser Ala Pro Ala
65                  70                  75                  80

Ala Ser Pro Ser Pro Ala Ala Pro Gln Pro Ser Pro Ala Ser Pro Ala
                85                  90                  95

Pro Ala Ser Pro Ala Ser Ala Pro Ser Ala Pro Ala Ser Ala Pro Ala
            100                 105                 110

Ala Ala Ser Ala Met Gln Ile Phe Val Lys Thr Leu Thr Gly Lys Thr
        115                 120                 125

Ile Thr Leu Glu Val Glu Pro Ser Asp Thr Ile Glu Asn Val Lys Ala
    130                 135                 140

Lys Ile Gln Asp Lys Glu Gly Ile Pro Pro Asp Gln Gln Arg Leu Ile
145                 150                 155                 160

Trp Ala Gly Lys Gln Leu Glu Asp Gly Arg Thr Leu Ser Asp Tyr Asn
                165                 170                 175

Ile Gln Lys Glu Ser Thr Leu His Leu Val Leu Arg Leu Arg Ala Ala
            180                 185                 190

Ser Ala Pro Ala Ala Ser Pro Ser Ala Ala Pro Ala Pro Ser Pro
        195                 200                 205

Ala Ser Pro Ala Pro Ala Ser Pro Ala Ser Ala Pro Ser Ala Pro Ala
    210                 215                 220

Ser Ala Pro Pro Ala Ala Ser Cys Ser Ala Pro Ala Ala Ser Pro Ser
225                 230                 235                 240

Pro Ala Ala Pro Ala Pro Ser Pro Ala Ser Pro Ala
                245                 250

<210> SEQ ID NO 45
<211> LENGTH: 252
<212> TYPE: PRT
<213> ORGANISM: Artificial Sequence
<220> FEATURE:
<223> OTHER INFORMATION: Artificially synthesized CID 180340
      (UBI-40APSD-UBI-60APSD/C)

<400> SEQUENCE: 45

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala Ser Ala Pro Ala

```
                65                   70                  75                  80
Ala Ser Pro Asp Pro Ala Ala Pro Gln Pro Ser Asp Ala Ser Pro Ala
                    85                  90                  95

Pro Ala Ser Asp Ala Ser Ala Pro Ser Ala Pro Asp Ser Ala Pro Ala
                100                 105                 110

Ala Ala Ser Ala Met Gln Ile Phe Val Lys Thr Leu Thr Gly Lys Thr
            115                 120                 125

Ile Thr Leu Glu Val Glu Pro Ser Asp Thr Ile Glu Asn Val Lys Ala
    130                 135                 140

Lys Ile Gln Asp Lys Glu Gly Ile Pro Pro Asp Gln Gln Arg Leu Ile
145                 150                 155                 160

Trp Ala Gly Lys Gln Leu Glu Asp Gly Arg Thr Leu Ser Asp Tyr Asn
                165                 170                 175

Ile Gln Lys Glu Ser Thr Leu His Leu Val Leu Arg Leu Arg Ala Ala
            180                 185                 190

Ser Ala Pro Ala Ala Asp Pro Ser Ala Ala Asp Ala Pro Ser Pro
    195                 200                 205

Ala Asp Pro Ala Pro Ala Ser Asp Ala Ser Ala Pro Ser Asp Pro Ala
    210                 215                 220

Ser Ala Asp Pro Ala Ala Ser Cys Ser Ala Pro Ala Ala Ser Pro Ser
225                 230                 235                 240

Pro Ala Ala Pro Ala Pro Ser Pro Ala Ser Pro Ala
                245                 250

<210> SEQ ID NO 46
<211> LENGTH: 310
<212> TYPE: PRT
<213> ORGANISM: Artificial Sequence
<220> FEATURE:
<223> OTHER INFORMATION: Artificially synthesized CID 180341
      (UBI-79APS-UBI-79APS/C)

<400> SEQUENCE: 46

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala Ser Ala Pro Ala
65                  70                  75                  80

Ala Ser Pro Ser Pro Ala Ala Pro Ala Pro Ser Pro Ala Ser Pro Ala
                85                  90                  95

Pro Ala Ser Pro Ala Ser Ala Pro Ser Ala Pro Ala Ser Ala Pro Ala
                100                 105                 110

Ala Ala Ser Ala Ser Ala Pro Ala Ser Pro Ser Pro Ala Ala Pro
            115                 120                 125

Ala Pro Ser Pro Ala Ser Pro Gln Pro Ala Ser Pro Ala Ser Ala Pro
    130                 135                 140

Ser Ala Pro Ala Ser Ala Pro Ala Ala Ser Ala Met Gln Ile Phe Val
145                 150                 155                 160

Lys Thr Leu Thr Gly Lys Thr Ile Thr Leu Glu Val Glu Pro Ser Asp
                165                 170                 175
```

```
Thr Ile Glu Asn Val Lys Ala Lys Ile Gln Asp Lys Glu Gly Ile Pro
            180                 185                 190

Pro Asp Gln Gln Arg Leu Ile Trp Ala Gly Lys Gln Leu Glu Asp Gly
        195                 200                 205

Arg Thr Leu Ser Asp Tyr Asn Ile Gln Lys Glu Ser Thr Leu His Leu
    210                 215                 220

Val Leu Arg Leu Arg Ala Ala Ser Ala Pro Ala Ala Ser Pro Ser Ala
225                 230                 235                 240

Ala Ala Pro Ala Pro Ser Pro Ala Ser Pro Ala Pro Ala Ser Pro Ala
                245                 250                 255

Ser Ala Pro Ser Ala Pro Ala Ser Ala Pro Pro Ala Ala Ser Pro Ser
            260                 265                 270

Ala Pro Ala Ala Ser Pro Ser Pro Ala Ala Pro Ala Pro Ser Pro Ala
        275                 280                 285

Ser Cys Ala Ala Ala Ser Pro Ser Ala Pro Ala Ala Ser Pro Ser Pro
    290                 295                 300

Ala Ala Pro Ala Pro Ser
305                 310

<210> SEQ ID NO 47
<211> LENGTH: 487
<212> TYPE: PRT
<213> ORGANISM: Artificial Sequence
<220> FEATURE:
<223> OTHER INFORMATION: Artificially synthesized CID 181790
      (79APS-UBI-79APS-UBI-79APS/C)

<400> SEQUENCE: 47

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Ser Ala Ser Ala Ala Ser Pro Ser Pro Ala Ala Pro Gln Pro
            100                 105                 110

Ser Pro Ala Ser Pro Ala Pro Ala Ser Pro Ala Ser Ala Pro Ser Ala
        115                 120                 125

Pro Ala Ser Ala Pro Ala Ala Ser Ala Ser Pro Ala Ala Ser
    130                 135                 140

Pro Ser Pro Ala Ala Pro Ala Pro Ser Pro Ala Ser Pro Ala Pro Ala
145                 150                 155                 160

Ser Pro Ala Ser Ala Pro Ser Ala Pro Ala Ser Ala Pro Ala Ala Ser
                165                 170                 175

Ala Met Gln Ile Phe Val Lys Thr Leu Thr Gly Lys Thr Ile Thr Leu
            180                 185                 190

Glu Val Glu Pro Ser Asp Thr Ile Glu Asn Val Lys Ala Lys Ile Gln
        195                 200                 205

Asp Lys Glu Gly Ile Pro Pro Asp Gln Gln Arg Leu Ile Trp Ala Gly
    210                 215                 220
```

Lys Gln Leu Glu Asp Gly Arg Thr Leu Ser Asp Tyr Asn Ile Gln Lys
225                 230                 235                 240

Glu Ser Thr Leu His Leu Val Leu Arg Leu Arg Ala Ala Ser Ala Pro
            245                 250                 255

Ala Ala Ser Pro Ser Ala Ala Pro Gln Pro Ser Pro Ala Ser Pro
        260                 265                 270

Ala Pro Ala Ser Pro Ala Ser Ala Pro Ser Ala Pro Ala Ser Ala Pro
        275                 280                 285

Pro Ala Ala Ser Pro Ser Ala Pro Ala Ala Ser Pro Ser Pro Ala Ala
        290                 295                 300

Pro Ala Pro Ser Pro Ala Ser Pro Ala Ala Ser Pro Ser Ala Pro
305                 310                 315                 320

Ala Ala Ser Pro Ser Pro Ala Ala Pro Ala Pro Ser Met Gln Ile Phe
            325                 330                 335

Val Lys Thr Leu Thr Gly Lys Thr Ile Thr Leu Glu Val Glu Pro Ser
            340                 345                 350

Asp Thr Ile Glu Asn Val Lys Ala Lys Ile Gln Asp Lys Glu Gly Ile
            355                 360                 365

Pro Pro Asp Gln Gln Arg Leu Ile Trp Ala Gly Lys Gln Leu Glu Asp
        370                 375                 380

Gly Arg Thr Leu Ser Asp Tyr Asn Ile Gln Lys Glu Ser Thr Leu His
385                 390                 395                 400

Leu Val Leu Arg Leu Arg Ala Ala Ser Ala Pro Ala Ala Ser Pro Ser
                405                 410                 415

Ala Ala Ala Pro Ala Pro Ser Pro Ser Pro Ala Pro Ala Ser Pro
            420                 425                 430

Ala Ser Ala Pro Ser Ala Pro Ser Ala Pro Pro Ala Ala Ser Pro
            435                 440                 445

Ser Ala Pro Ala Ala Ser Pro Ser Pro Ala Ala Pro Ala Pro Ser Pro
            450                 455                 460

Ala Ser Cys Ala Ala Ala Ser Pro Ser Ala Pro Ala Ala Ser Pro Ser
465                 470                 475                 480

Pro Ala Ala Pro Ala Pro Ser
                485

<210> SEQ ID NO 48
<211> LENGTH: 275
<212> TYPE: PRT
<213> ORGANISM: Artificial Sequence
<220> FEATURE:
<223> OTHER INFORMATION: Artificially synthesized 183422 ? N-terminal
      His-Tag/Sumo/77404 with S57C

<400> SEQUENCE: 48

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp

```
            85                  90                  95
Gln Thr Pro Glu Asp Leu Asp Met Glu Asp Asn Asp Ile Ile Glu Ala
            100                 105                 110

His Arg Glu Gln Ile Gly Gly Met Arg Ile Trp Val His Thr Leu Thr
            115                 120                 125

Gly Lys Thr Ile Thr Leu Glu Val Glu Pro Ser Asp Thr Ile Glu Asn
            130                 135             140

Val Lys Ala Lys Ile Gln Asp Lys Glu Gly Ile Pro Pro Asp Gln Gln
145                 150                 155                 160

Arg Leu Ile Trp Ala Gly Lys Gln Leu Glu Asp Gly Arg Thr Leu Ser
                165                 170                 175

Asp Tyr Asn Ile Asn Pro Lys Leu Ser Leu His Leu Val Leu Arg Leu
            180                 185                 190

Arg Ala Ala Gly Ile Gly Met Gln Ile Phe Val His Thr Gln Thr Gly
            195                 200                 205

Lys Thr Ile Thr Leu Glu Val Glu Pro Ser Asp Thr Ile Glu Asn Val
            210                 215                 220

Lys Ala Lys Ile Gln Asp Lys Glu Gly Ile Pro Pro Asp Gln Gln Arg
225                 230                 235                 240

Leu Ile Trp Ala Gly Lys Gln Leu Glu Asp Gly Arg Thr Leu Ser Asp
                245                 250                 255

Tyr Asn Ile Gly Trp Gln Ala Pro Leu His Leu Val Leu Arg Leu Arg
            260                 265                 270

Ala Ala Cys
        275

<210> SEQ ID NO 49
<211> LENGTH: 274
<212> TYPE: PRT
<213> ORGANISM: Artificial Sequence
<220> FEATURE:
<223> OTHER INFORMATION: Artificially synthesized 183423 ? N-terminal
      His-Tag/Sumo/77404 with S57C

<400> SEQUENCE: 49

Met Gly Ser Ser His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
            35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Met Arg Ile Trp Val His Thr Leu Thr
            115                 120                 125

Gly Lys Thr Ile Thr Leu Glu Val Glu Pro Ser Asp Thr Ile Glu Asn
            130                 135             140

Val Lys Ala Lys Ile Gln Asp Lys Glu Gly Ile Pro Pro Asp Gln Gln
145                 150                 155                 160
```

Arg Leu Ile Trp Ala Gly Lys Gln Leu Glu Asp Gly Arg Thr Leu Ser
            165                 170                 175

Asp Tyr Asn Ile Asn Pro Lys Leu Ser Leu His Leu Val Leu Arg Leu
        180                 185                 190

Arg Ala Ala Gly Ile Gly Met Gln Ile Phe Val His Thr Gln Thr Gly
            195                 200                 205

Lys Thr Ile Thr Leu Glu Val Glu Pro Ser Asp Thr Ile Glu Asn Val
210                 215                 220

Lys Ala Lys Ile Gln Asp Lys Glu Gly Ile Pro Asp Gln Gln Arg
225                 230                 235                 240

Leu Ile Trp Ala Gly Lys Gln Leu Glu Asp Gly Arg Thr Leu Cys Asp
            245                 250                 255

Tyr Asn Ile Gly Trp Gln Ala Pro Leu His Leu Val Leu Arg Leu Arg
            260                 265                 270

Ala Ala

<210> SEQ ID NO 50
<211> LENGTH: 273
<212> TYPE: PRT
<213> ORGANISM: Artificial Sequence
<220> FEATURE:
<223> OTHER INFORMATION: Artificially synthesized 184168 ? N-terminal
      His-Tag/Sumo/138800 with c-terminal Cys

<400> SEQUENCE: 50

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
            85                  90                  95

Gln Thr Pro Glu Asp Leu Asp Met Glu Asp Asn Asp Ile Ile Glu Ala
        100                 105                 110

His Arg Glu Gln Ile Gly Gly Met Gln Ile Phe Val His Thr Asp Thr
    115                 120                 125

Gly Lys Thr Ile Thr Leu Glu Val Glu Pro Ser Asp Thr Ile Glu Asn
130                 135                 140

Val Lys Ala Lys Ile Gln Asp Lys Glu Gly Ile Pro Gln Asp Gln Gln
145                 150                 155                 160

Arg Leu Ile Trp Ala Gly Lys Gln Leu Glu Asp Gly Arg Thr Leu Ser
            165                 170                 175

Asp Tyr Asn Ile Asp Pro Gln Leu Lys Leu His Leu Val Leu Arg Leu
        180                 185                 190

Arg Ala Ala Gly Gly Met Gln Ile Phe Val Thr Thr Gln Thr Gly Lys
    195                 200                 205

Thr Ile Thr Leu Glu Val Glu Pro Ser Asp Thr Ile Glu Asn Val Lys
210                 215                 220

Ala Lys Ile Gln Asp Lys Glu Gly Ile Pro Pro Asp Gln Gln Arg Leu
225                 230                 235                 240

Ile Trp Ala Gly Lys Gln Leu Glu Asp Gly Arg Thr Leu Ser Asp Tyr
            245                 250                 255

Asn Ile Asp Tyr Arg Phe Leu His Leu Val Leu Arg Leu Arg Ala Ala
            260                 265                 270

Cys

<210> SEQ ID NO 51
<211> LENGTH: 272
<212> TYPE: PRT
<213> ORGANISM: Artificial Sequence
<220> FEATURE:
<223> OTHER INFORMATION: Artificially synthesized 184169 - N-terminal
      His-Tag/Sumo/138800 with S57C

<400> SEQUENCE: 51

Met Gly Ser Ser His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
            35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Met Gln Ile Phe Val His Thr Asp Thr
            115                 120                 125

Gly Lys Thr Ile Thr Leu Glu Val Glu Pro Ser Asp Thr Ile Glu Asn
            130                 135                 140

Val Lys Ala Lys Ile Gln Asp Lys Glu Gly Ile Pro Gln Asp Gln Gln
145                 150                 155                 160

Arg Leu Ile Trp Ala Gly Lys Gln Leu Glu Asp Gly Arg Thr Leu Ser
                165                 170                 175

Asp Tyr Asn Ile Asp Pro Gln Leu Lys Leu His Leu Val Leu Arg Leu
            180                 185                 190

Arg Ala Ala Gly Gly Met Gln Ile Phe Val Thr Thr Gln Thr Gly Lys
            195                 200                 205

Thr Ile Thr Leu Glu Val Glu Pro Ser Asp Thr Ile Glu Asn Val Lys
            210                 215                 220

Ala Lys Ile Gln Asp Lys Glu Gly Ile Pro Pro Asp Gln Gln Arg Leu
225                 230                 235                 240

Ile Trp Ala Gly Lys Gln Leu Glu Asp Gly Arg Thr Leu Cys Asp Tyr
                245                 250                 255

Asn Ile Asp Tyr Arg Phe Leu His Leu Val Leu Arg Leu Arg Ala Ala
            260                 265                 270

<210> SEQ ID NO 52
<211> LENGTH: 10
<212> TYPE: PRT

```
<213> ORGANISM: Artificial Sequence
<220> FEATURE:
<223> OTHER INFORMATION: Artificially synthesized StrepTag extension for
      purification

<400> SEQUENCE: 52

Ser Ala Trp Ser His Pro Gln Phe Glu Lys
1               5                   10
```